United States Patent [19]
Pathirana et al.

[11] Patent Number: 5,808,139
[45] Date of Patent: Sep. 15, 1998

[54] NON-STEROID PROGESTERONE RECEPTOR AGONIST AND ANTAGONIST AND COMPOUNDS AND METHODS

[75] Inventors: I. Charles Pathirana; Christina S. Berger; Robert B. Stein, all of San Diego; William Fenical, Del Mar; Todd K. Jones, Solana Beach; Lawrence G. Hamann; Michael G. Johnson, both of San Diego; Luc Farmer, La Jolla, all of Calif.

[73] Assignees: Ligand Pharmaceuticals Incorporated, San Diego; The Regents of the University of California, Oakland, both of Calif.

[21] Appl. No.: 303,138

[22] Filed: Sep. 8, 1994

Related U.S. Application Data

[63] Continuation of Ser. No. 140,811, Oct. 21, 1993, abandoned, which is a continuation-in-part of Ser. No. 48,646, Apr. 16, 1993, abandoned, which is a continuation-in-part of Ser. No. 872,710, Apr. 21, 1992.

[51] Int. Cl.$^6$ .................................................. C07C 69/76
[52] U.S. Cl. ......................... 560/138; 546/192; 549/356; 514/542
[58] Field of Search .................................. 560/138, 140, 560/142, 147, 155; 546/192; 549/356; 562/433, 438, 426, 431, 432; 514/542, 546, 876; 435/7.1, 69.4, 172.1; 436/501, 119, 126, 87; 935/33

[56] References Cited

U.S. PATENT DOCUMENTS

| | | |
|---|---|---|
| 4,778,621 | 10/1988 | Isoyama et al. . |
| 4,780,420 | 10/1988 | Hochberg et al. . |
| 4,981,784 | 1/1991 | Evans et al. . |
| 5,017,610 | 5/1991 | Imaki et al. . |
| 5,071,773 | 12/1991 | Evans et al. . |
| 5,128,479 | 7/1992 | Janssen et al. . |
| 5,134,155 | 7/1992 | Connolly et al. . |
| 5,135,940 | 8/1992 | Belanger et al. . |

FOREIGN PATENT DOCUMENTS 0474301  3/1992  European Pat. Off. .

OTHER PUBLICATIONS

McConnell, O.J.; Phytochemistry, vol. 21; pp. 2139–2141, 1982.
Hogberg, Hans–Erik et al; JCS Perkin I, pp. 1696–1701, 1976.
Tanaka, A et al; Agric. Biol.. Chem.; vol. 54(1), pp. 121–123, 1990.
Antus, S. et al., Tetrahedron, vol. 42, No. 20, pp. 5637–5640 (1986).
Chakravarty, J. et al., Proc. Indian Acad. Sci., vol. 86A, No. 3, pp. 317–325 (Sep. 1977).
Chirko, A.I. et al., Chem. Abstr. No. 94773s, vol. 66, pp. 8859–8860 (1967).
Destabel, C. et al., J. Chem. Soc., Chem. Commun., pp. 596–598 (1992).
Gupta, K., J. Indian Chem. Soc., vol. 42, No. 5, pp. 415–423 (1969).
Laumen, K. et al., J. Chem. Soc., Chem. Commun., pp. 49–51 (1990).
Moreau, M. et al., Bulletin de la Sociéte Chimique de France, No. 4, pp. 1362–1367 (1969).
Nagano, H. et al., Bull. Chem. Soc. Jpn., 65:2421–2426 (1992).
Narasaka, K. et al., Chemistry Letters, The Chem. Soc. of Japan, pp. 1413–1416 (1991).
Narasaka, K. et al., Tetrahedron, vol. 48, No. 11, pp. 2059–2068 (1991).
Pal, S. et al., J. Chem. Soc., Chem. Commun., pp. 1591–1593 (1991).
Yardley, J.P. et al., Experientia, pp. 1124–1125 (11 Jan. 1978).
Aoki, S. et al., J. Am. Chem. Soc., 110:3296–98 (1988).
Banik, B.K., J. Chem. Res. (S), pp. 406–407 (1986).
Berry, N.M. et al., Synthesis, No. 6, pp. 476–480. (Jun., 1986)
Davis, B.R. et al., J. Am. Chem. Soc. Perkin I, pp. 2840–2844 (1978).
Kaminsky, D. et al., Tetrahedron Letters, No. 10, pp. 859–861 (1967).
Pal, S. et al., Synthesis, No. 11, pp. 1073–1075 (Nov. 1992).
Chemical Abstracts, vol. 118, No. 11 (1992), No. 101626u.
Chemical Abstracts, vol. 117, No. 19 (1988), No. 192104r.
Chemical Abstracts, vol. 107, No. 13 (1986), No. 115810j.
Chemical Abstracts, vol. 106, No. 7 (1986), No. 4964e.
Chemical Abstracts, vol. 73, No. 8 (1969), No. 36564h.
Evans, R.M., Science, 240:889–95 (May 13, 1988).
Hogberg, H. and Thomson, J. Chem. Soc. Perkin Trans. 1, pp. 1696–1701 (1976).
McConnell, O.J. et al., Phytochemistry, 21:2139–41 (1982).
Tanaka, A. et al., Agric. Biol. Chem., 54(1):121–123 (1990).
Wall, M.E., et al., J. of Natl. Prod., 52:1092–99 (Sep.–Oct. 1989).

Primary Examiner—Gary Geist
Assistant Examiner—Sreeni Padmanabhan
Attorney, Agent, or Firm—Lyon & Lyon LLP

[57] ABSTRACT

Non-steroidal compounds which are high affinity, high specificity ligands for progesterone receptors are disclosed. The compounds include synthetic derivatives of cyclocymopol and its diastereomers, spectroscopically and chromatographically pure (3R)-cyclocymopol monomethyl ether, which functions as a progesterone receptor antagonist, and spectroscopically and chromatographically pure (3S)-cyclocymopol monomethyl ether, which functions as a progesterone receptor agonist. Also disclosed are methods for employing the disclosed compounds for modulating processes mediated by progesterone receptors and for treating patients requiring progesterone receptor agonist or antagonist therapy.

27 Claims, 12 Drawing Sheets

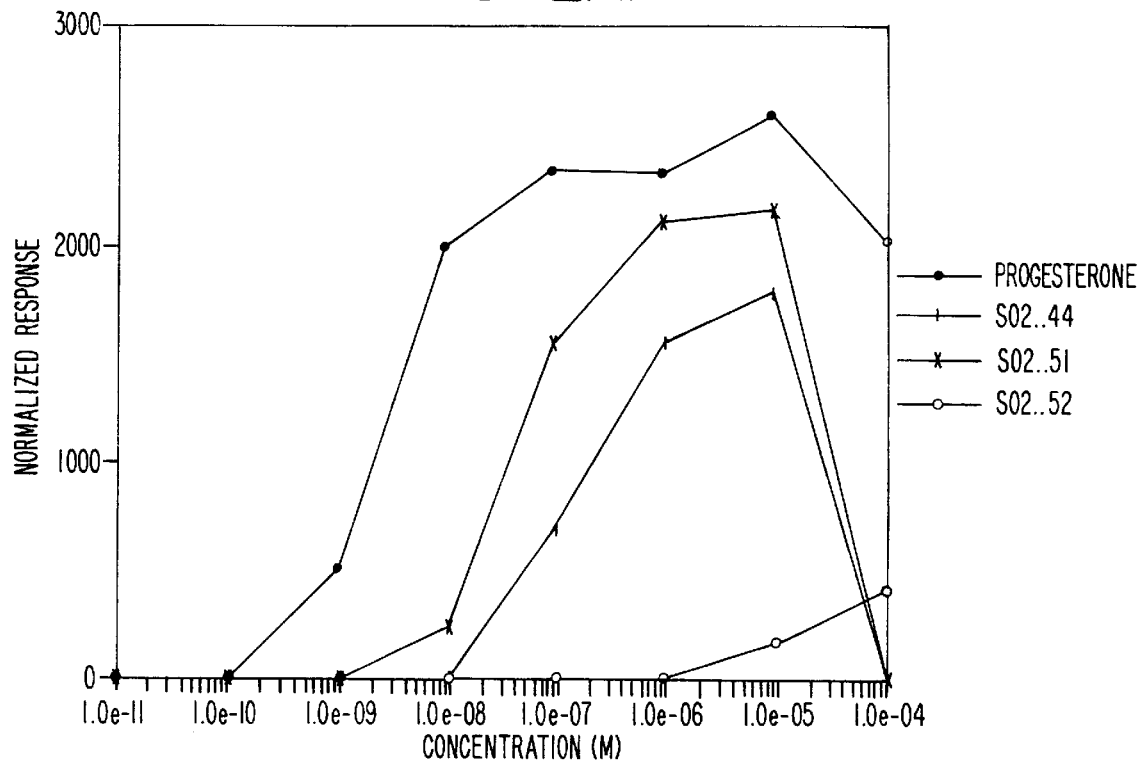
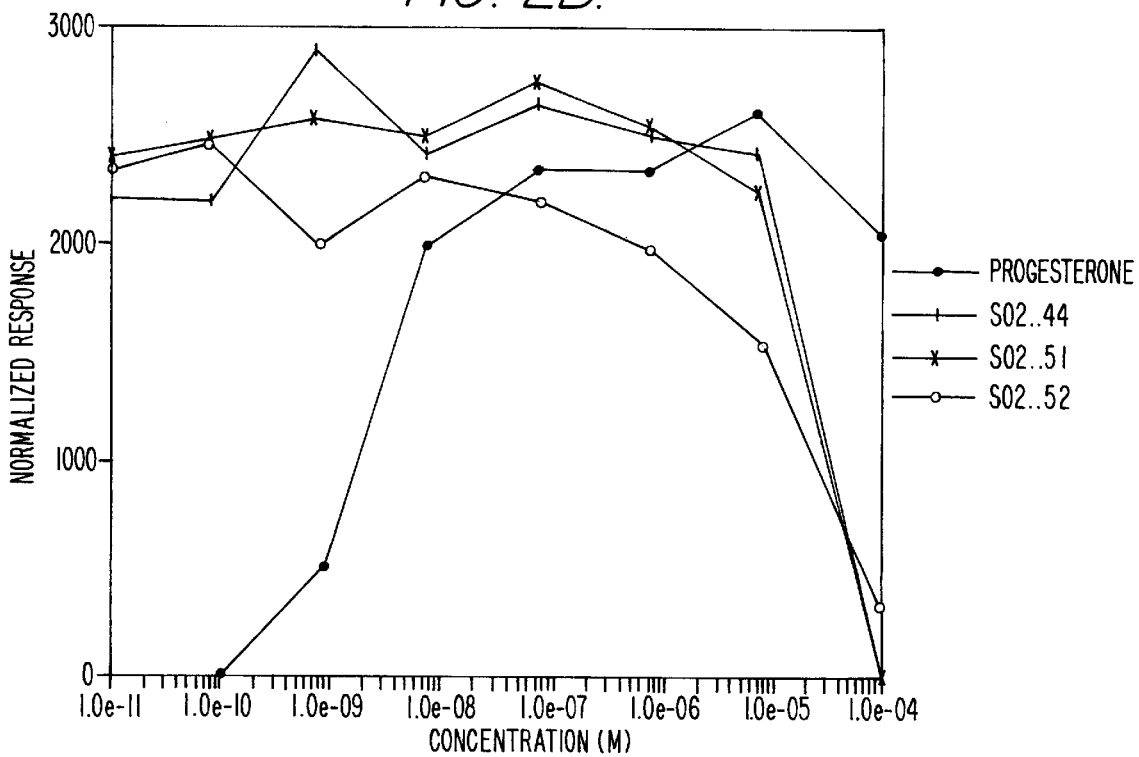

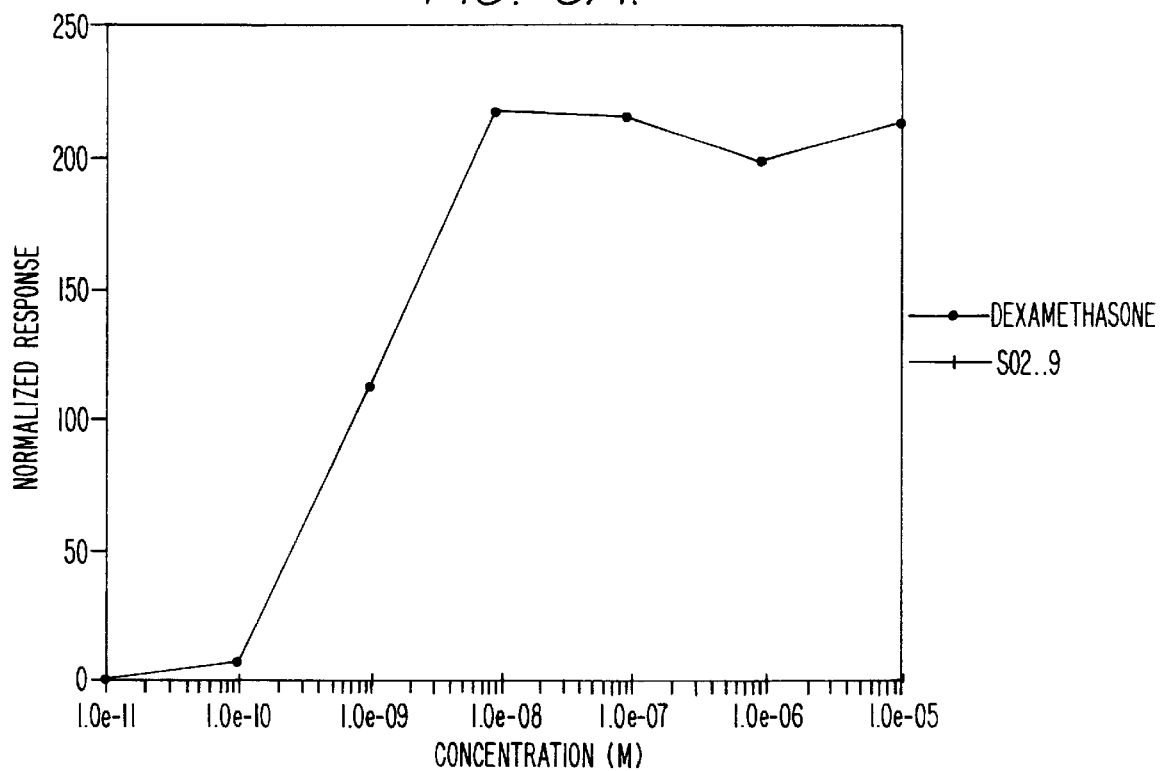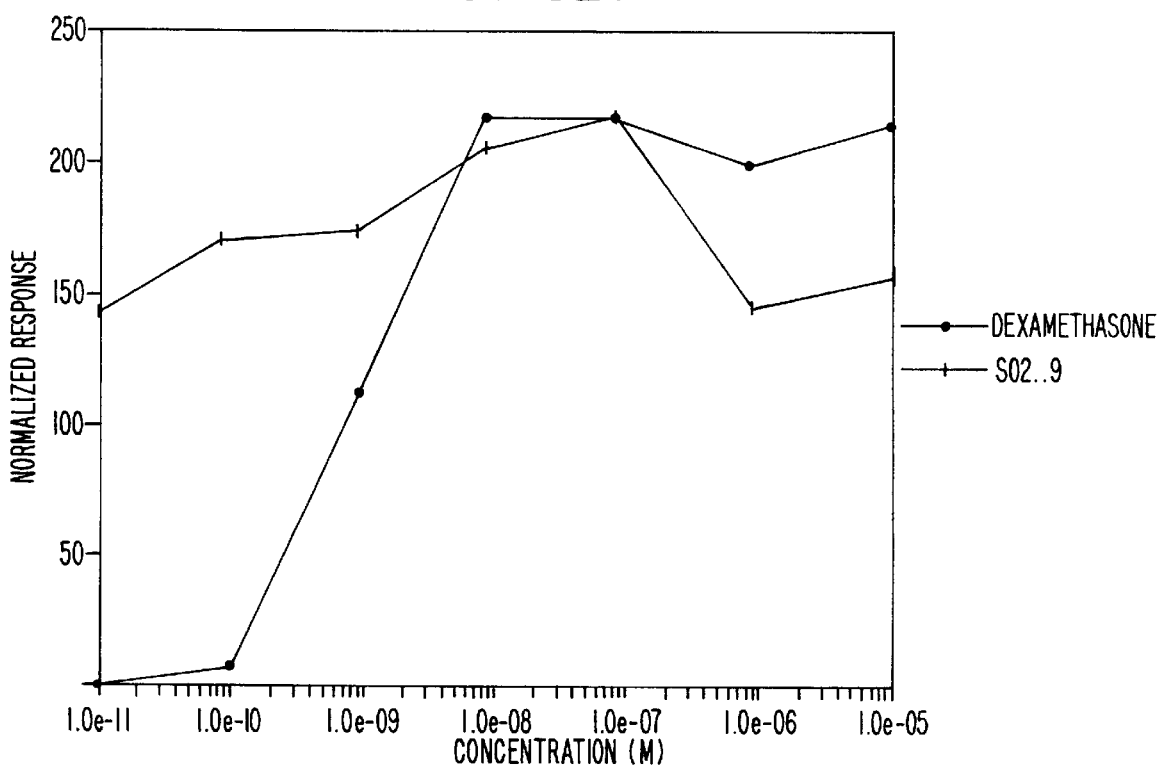

NON-STEROID PROGESTERONE RECEPTOR AGONIST AND ANTAGONIST AND COMPOUNDS AND METHODS

RELATED APPLICATIONS

This is a continuation of application Ser. No. 08/140,811 filed on Oct. 21, 1993 now abandoned which is a continuation-in-part of U.S. patent application Ser. No. 08/048,646 filed Apr. 16, 1993, now abandoned, which in turn is a continuation-in-part of U.S. patent application Ser. No. 07/872,710 filed Apr. 21, 1992, the entire disclosures of which are herein expressly incorporated by reference.

This invention was made with Government support under Grant No. NA 89 AA-D-SG138 awarded by the California Sea Grant Program of the National Oceanographic and Atmospheric Administration. The Government has certain rights in the invention.

FIELD OF THE INVENTION

This invention relates to intracellular receptors and ligands therefor. More specifically, this invention relates to compounds which are non-steroidal progesterone receptor antagonists or agonists, and methods for use of such compounds or ligands.

BACKGROUND OF THE INVENTION

A central problem in eukaryotic molecular biology continues to be the elucidation of molecules and mechanisms that mediate specific gene regulation in response to molecular inducers such as hormones. As part of the scientific attack on this problem, a great deal of work has been done in efforts to identify molecular inducers which are capable of mediating specific gene regulation.

Although much remains to be learned about the specifics of gene regulation, it is known that certain small molecule, non-peptide hormones and similarly acting vitamins and vitamin metabolites (collectively hereinafter called "hormones") modulate gene transcription by acting in concert with intracellular components, including intracellular receptors and discrete DNA promoter enhancer sequences known as hormone response elements (HREs).

These hormones, acting through, and as "ligands" for, their intracellular receptors, directly regulate hormone-responsive genes (and perhaps other important genes which are not directly hormone-responsive). Natural ligands for intracellular receptors are synthesized in the body or may be taken in as a component of food. It has also been shown that compounds other than the natural ligands can act upon intracellular receptors to regulate hormone-responsive genes. For example, some natural product derivatives and synthetic compounds also function as ligands for these receptors.

Intracellular receptors form a class of structurally-related genetic regulators scientists have named "ligand dependent transcription factors." Regulation of a gene by such factors requires both the intracellular receptor itself and a corresponding ligand which has the ability to selectively bind to the intracellular receptor in a way that affects gene activity. Until bound by a ligand, the intracellular receptor is unable to exert an effect on the gene. Hormone or other ligand molecules in the fluid surrounding a cell pass through the outer cell membrane by passive diffusion. Once inside the cell, the ligand binds to specific intracellular receptor proteins, creating a ligand/receptor complex. The binding of the ligand to its receptor induces a change in the shape of the intracellular receptor. This conformational change is believed to expose regions of the intracellular receptor that permit the intracellular receptor/ligand complex to bind to a specific subset of genes present in the cell's DNA in the cell nucleus.

The blueprint to build specific proteins is encoded in the DNA sequence of each gene. This blueprint is copied in a process referred to as "transcription," to give rise to the actual template for the production of specific proteins, messenger RNA or "mRNA". The MRNA then moves from the cell's nucleus into the cytoplasm and is translated, which results in the production of proteins encoded in the MRNA. Accordingly, a reduction in the transcription of mRNA reduces the production of the specific proteins.

Once the intracellular receptor/ligand complex binds to the specific site on the DNA, it alters the amount of the protein encoded by the gene that the cell is directed to produce, by altering the amount of mRNA transcribed by that gene. A ligand which binds an intracellular receptor and mimics the effect of the natural ligand is referred to as an "agonist" ligand. A ligand that inhibits the effect of the hormone is called an "antagonist." Intracellular receptors are referred to as "ligand-dependent transcription factors" because their activity is dependent upon the binding of their hormonal or other ligands, which are necessary to drive the intracellular receptor into its active conformation.

The intracellular receptors form a large family of proteins that are closely related in structure. They are important drug targets, and many drugs currently on the market are ligands for these receptors. Not surprisingly, the structural similarity of the receptors often results in cross-reactivity between a drug and receptors other than its target. It is apparent, therefore, that there is a need to find alternative ligands (agonists and antagonists) which are readily available for therapeutic administration, have added specificity for particular receptors, and have increased activity.

Ligands to the progesterone receptor are known to play an important role in gynecological medicine, cancer, and other health care problems of women. Its natural ligand, the female steroid progesterone, and synthetic analogues are, for example, used in birth control formulations. Antagonists to progesterone are useful in treating chronic disorders such as certain forms of hormone dependent cancer of the breast, ovaries, and endometrium (the lining of the uterus), and in treating uterine fibroids. Endometriosis, a leading cause of infertility in women, currently treated in early stage development by surgery, is also amenable to treatment with progesterone.

The identification of compounds which interact with progesterone receptors, and thereby affect transcription of genes which are responsive to progesterone, would be of significant value, e.g., for therapeutic applications such as treatment of hormonally-responsive gynecological and malignant disorders.

Further, the identification of compounds which have good specificity for the progesterone receptor, but which have less cross-reactivity for other intracellular receptors, would be of significant value since interaction of a ligand with other than the target intracellular receptors is known to result in significant undesirable pharmacological side effects. Accordingly, agonists and antagonists to the progesterone receptor which do not display cross-reactivity with other intracellular receptors will exhibit an improved therapeutic index.

A group of prenylated bromohydroquinones, called collectively cymopols, has been isolated and identified by several investigators using as a starting material the green marine alga *Cymopolia barbata* (L.) Lamouroux (Dasycladaceae). Among these, cymopol, $C_{16}H_{21}BrO_2$, is a crystalline phenol which has a bromogeranyl-hydroquinone or brominated monoterpene-quinol structure. As described by Högberg et al., J. C. S. Perkin I, 1696–1701 (1976), cymopol[2-bromo-5-(3,7-dimethylocta-2,6-dienyl) hydroquinone] and its monomethyl ether, $C_{17}H_{23}BrO_2$, have the following structures:

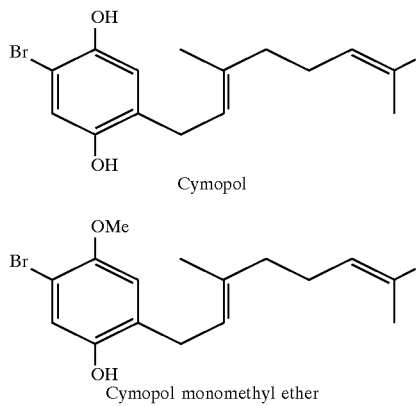

Cymopol

Cymopol monomethyl ether

Cyclocymopol[1-bromo-3-(4-bromo-2,5-dihydroxybenzyl)-2,2-dimethyl-4 methylene cyclohexane] and its monomethyl ether have also been obtained from *C. barbata*. See Högberg et al., supra. As described in McConnell et al., Phytochemistry, Vol. 21, No. 8, pp. 2139–41 (1982), *C. barbata* contains a mixture of optically active diastereomers of cyclocymopol, $C_{16}H_{20}Br_2O_2$, and cyclocymopol monomethyl ether, $C_{17}H_{22}Br_2O_2$, having the following structures:

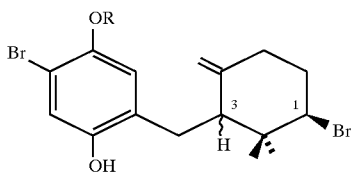

1a (R=H): 2a (R=Me): H (C-3)-pseudo-equatorial 1b (R=H): 2b (R=Me): H (C-3)-pseudo-axial (The above assumes the equatorial conformation for bromine at C-1).

Through silica gel chromatography of an ether-soluble extract of *C. barbata,* McConnell et al. were able to obtain a 1:1 mixture of α:β epimers of cyclocymopol. McConnell et al. also obtained a 3:1 mixture of α:β epimers of cyclocymopol monomethyl ether, which was enriched to a 4:1 mixture of the α:β epimers through purification techniques.

Wall et al., J. Nat. Prod., Vol. 52, No. 5, pp. 1092–99 (1989), described additional diastereomeric cymopol compounds (cymobarbatol and 4-isocymobarbatol) which were determined to be highly active antimutagens. Wall et al. reported obtaining pure cymobarbatol compounds, but were unable to obtain stable cyclocymopol fractions. Apparently, however, the forms of cyclocympol and cyclocymopol monomethyl ether obtained by Högberg et al., supra, were pure forms of formulae 1b and 2b above.

The publications and references referred to above and hereafter in this specification are incorporated herein by reference.

SUMMARY OF THE INVENTION

The present invention is directed to compounds, compositions, and methods for modulating processes medi- ated by progesterone receptors. More particularly, the invention relates to non-steroidal compounds which are high affinity, high specificity ligands for progesterone receptors. These compounds exhibit progesterone receptor agonist or progesterone receptor antagonist activity, and modulate processes mediated by progesterone receptors. Accordingly, the invention also relates to methods for modulating processes mediated by progesterone receptors employing the compounds disclosed. Examples of compounds used in and forming part of the invention include cyclocymopol derivatives and purified diastereomers thereof, synthetic cyclocymopol analogs, and semisynthetic derivatives of natural cyclocymopols. Pharmaceutical compositions containing the compounds disclosed are also within the scope of this invention. Also included are methods for identifying or purifying progesterone receptors by use of the compounds of this invention.

DEFINITIONS

In accordance with the present invention and as used herein, the following terms are defined with the following meanings, unless explicitly stated otherwise.

The term alkyl refers to straight-chain, branched-chain, cyclic structures, and combinations thereof.

The term "aryl" refers to aromatic groups which have at least one ring having a conjugated pi electron system and includes carbocyclic aryl, heterocyclic aryl and biaryl groups, all of which may be optionally substituted, being preferably phenyl or phenyl substituted by one to three substituents, such substituents being advantageously lower alkyl, hydroxy, lower alkoxy, lower acyloxy, halogen, cyano, trihalomethyl, lower alcylamino, or lower alkoxycarbonyl.

Carbocyclic aryl groups are groups wherein the ring atoms on the aromatic ring are carbon atoms. Carbocyclic aryl groups include monocyclic carbocyclic aryl groups and optionally substituted naphthyl groups.

Heterocyclic aryl groups are groups having from 1 to 3 heteroatoms as ring atoms in the aromatic ring with the remainder of the ring atoms being carbon atoms. Suitable heteroatoms include oxygen, sulfur, and nitrogen, and suitable heterocyclic aryl groups include furanyl, thienyl, pyridyl, pyrrolyl, N-lower alkyl pyrrolyl, pyrimidyl, pyrazinyl, imidazolyl, and the like, all optionally substituted.

The term "aralkyl" refers to an alkyl group substituted with an aryl group. Suitable aralkyl groups include benzyl and the like, and may be optionally substituted.

The term "lower" referred to herein in connection with organic radicals or compounds respectively defines such with up to and including 7, preferably up to and including 4 and advantageously one or two, carbon atoms. Such groups may be straight chain or branched.

BRIEF DESCRIPTION OF THE DRAWINGS

The present invention may be better understood and its advantages appreciated by those skilled in the art by referring to the accompanying drawings wherein:

FIG. 2 presents activation profiles for analysis of progesterone receptor activation by a cyclocymopol monomethyl ether diastereomeric mixture (compound SO-44), by a pure 3S diastereomeric acetate (compound SO-51), and by a pure 3R diastereomeric acetate (compound SO-52). For these compounds and a progesterone control, agonist dose response is shown in panel a, and antagonist dose response in panel b;

FIG. 6 presents activation profiles for analysis of glucocorticoid receptor activation by (3R)-cyclocymopol monomethyl ether (compound SO-09). For this compound and a dexamethasone control, agonist dose response is shown in panel a and antagonist dose response is shown in panel b;

DETAILED DESCRIPTION OF EMBODIMENTS OF THE INVENTION

Figure 1A:
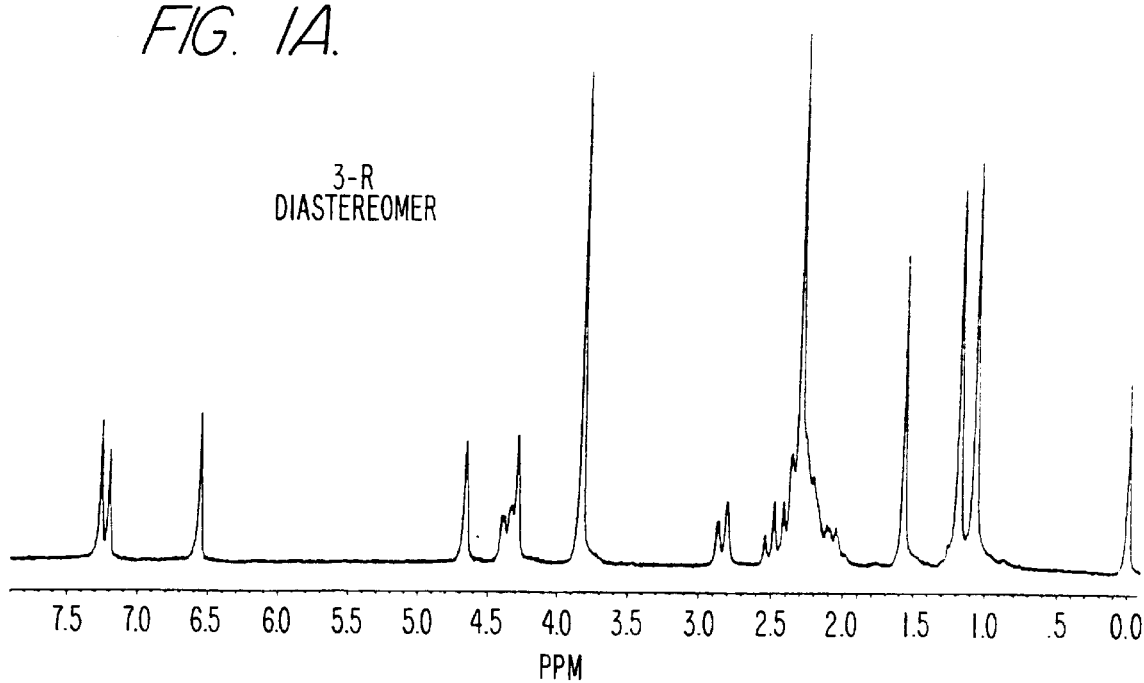
FIG. 1 presents the proton NMR spectrum for the individual pure 3R (panel a) and 3S (panel b) diastereomeric acetates of cyclocymopol monomethyl ether.

Cyclocymopols useful in this invention are defined as those having the formulae:

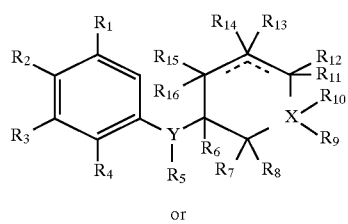

or

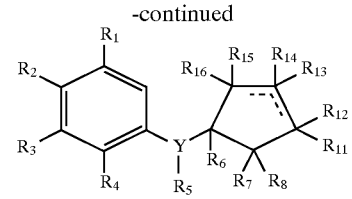

wherein:
the dotted lines in the structure depict optional double bonds;

X is carbon, oxygen, or nitrogen;

Y is oxygen, nitrogen, sulfur or a saturated or unsaturated $C_1$–$C_4$ alkyl, optionally substituted with oxygen, nitrogen or sulfur;

$R_1$ is $R_{17}$, —$OR_{17}$, —$N(R_{17})(R_{17'})$, —$SR_{17}$, fluorine, chlorine, bromine, or —$NO_2$;

$R_{17}$ and $(R_{17'})$, each independently, are hydrogen, a saturated or unsaturated $C_1$–$C_6$ alkyl, $C_3$–$C_7$ cycloalkyl, $C_5$–$C_7$ aryl, or $C_7$ aralkyl, said alkyl groups being branched or straight-chain;

$R_2$ is —$NO_2$, —$N(OH)R_{17}$, fluorine, chlorine, bromine, iodine, $R_{17}$, —$N(R_{17})(R_{17'})$, —$SR_{17}$, —$S(O)$—$R_{17}$, —$S(O)_2$—$R_{17}$, —$CH_2OH$, —$C(O)$—$H$, —$C(O)CH_3$, —$C(O)$—$OCH_3$, —$C$=$CH_2$, —$C$=$CH$—$C(O)$—$OCH_3$, or $R_{18}$;

$R_{18}$ and $(R_{18'})$, each independently are hydrogen, a saturated or unsaturated $C_1$–$C_6$ alkyl, $C_3$–$C_7$ cycloalkyl, $C_5$–$C_7$ aryl, or $C_7$ aralkyl, said alkyl groups being branched or straight-chain which optionally may contain hydroxyl, aldehyde, ketone, nitrile, or ester groups;

$R_3$ is $R_{17}$ or —$OR_{17}$, or $R_2$ and $R_3$ taken together can form a saturated or unsaturated heterocyclic 3–8 member ring substituted with one or more heteroatoms selected from the group consisting of oxygen, nitrogen, and sulfur, provided, however, that when $R_2$ and $R_3$ form such a saturated or unsaturated heterocyclic 3–8 member ring, then the bond between the carbon atoms carrying the $R_2$ and $R_3$ substituents can be either a single bond or a double bond;

$R_4$ is hydrogen, —$OR_{17}$, —$OC(O)R_{17}$, —$OC(O)OR_{17}$, —$OC(O)N(R_{17})(R_{17'})$, —$OS(O)_2R_{17}$, or —$OS(O)$—$R_{17}$;

$R_5$ is hydrogen or $OR_{17}$;

$R_6$ is $R_{17}$, or $OR_{17}$;

$R_7$ and $R_8$, each independently, are hydrogen, $R_{18}$, or $R_7$ and $R_8$ together are a carbocyclic 3–8 member ring;

$R_9$ and $R_{10}$, each independently, are chlorine, bromine, $R_{17}$, or $R_{18}$, or $R_9$ and $R_{10}$ combined are =O, except when X=0, then $R_9$ and $R_{10}$ are not present, and when X is N, then $R_{10}$ is not present, or $R_9$ and $R_{10}$ together are joined in a carbocyclic 3–8 member ring;

$R_{11}$ and $R_{12}$, each independently, are —$OR_{17}$, $R_{18}$, are =O, or are =$CH_2$. except when $R_{11}$ is attached to an $SP^2$ carbon atom in the ring, then $R_{12}$ is not present and $R_{11}$ is $R_{18}$;

or $R_{11}$ and $R_{13}$ together are joined in a carbocyclic 3–8 member ring or are —O— to form an epoxide, $R_{13}$ and $R_{14}$, each independently, are —$OR_{17}$ or $R_{18}$, except when $R_{13}$ is attached to an $sp^2$ carbon atom in the ring, then $R_{14}$ is not present and $R_{13}$ is —$OR_{17}$, or $R_{18}$;

$R_{15}$ and $R_{16}$, each independently, are $R_{18}$ or $OR_{17}$, or $R_{15}$ and $R_{16}$ together are joined in a carbocyclic 3–8 member ring, or $R_{15}$ and $R_{16}$ together are —$CH_2$—O— forming an epoxide, or $R_{15}$ and $R_{16}$ combined are =O or =$C(R_{18})(R_{18'})$, except when $R_{15}$ is hydroxyl, then $R_{16}$ is not hydroxyl, and when $R_{15}$ is attached to an $sp^2$ carbon atom in the ring, then $R_{16}$ is not present;

but excluding cyclocymopol and cyclocymopol monomethyl ether.

Representative compounds and derivatives according to the present invention include the following:

1-Methylidene-2-(2'-acetoxy-4'-bromo-5'-methoxyphenyl)methyl-3,3-dimethylcyclohexane;
(3S)-1-Debromocyclocymopol monomethyl ether,2'-acetate;
1-Methylidene-2-(2'-hydroxy-4'-bromo-5'-methoxyphenyl)methyl-3,3-dimethylcyclohexane;
(3S)-1-Debromocyclocymopol monomethyl ether,2'-methylcarbonate;
(3R,5R)-5-Hydroxycyclocymopol monomethyl ether;
2-(4'-Nitrophenyl)methylcyclohexanone;
(3S)-1-Debromocyclocymopol monomethyl ether;
1-Methylidene-6-(2'-acetoxy-4'-bromo-5'-methoxyphenyl)methyl-3,5,5-trimethylcyclohex-2-ene;
1-Methylidene-6-(4'-nitrophenyl)methyl-3,5,5-trimethylcyclohex-2-ene;
(3R)-1-Debromocyclocymopol monomethyl ether;
1-Methylidene-6-(2'-hydroxy-4'-bromo-5'-methoxyphenyl)methyl-5,5-dimethylcyclohex-2-ene;
1-Methylidene-6-(2'-acetoxy-4'-bromo-5'-methoxyphenyl)methyl-5,5-dimethylcyclohex-2-ene;
1-Methylidene-6-(3'-methyl-4'-nitrophenyl)methyl-5,5-dimethylcyclohex-2-ene;
trans-1-Methylidene-6-(2'-acetoxy-4'-bromo-5'-methoxyphenyl)methyl-4,5,5-trimethylcyclohex-2-ene;
1-Methylidene-2-(4'-bromophenyl)methyl-3,3-dimethylcyclohexane;
1-Methylidene-2-(2'-hydroxy-4'-bromo-5'-methoxyphenyl)methyl-3,3-dimethylcyclopentane;
1-Methylidene-2-(4'-nitrophenyl)methylcyclohexane;
(3R)-1-Debromocyclocymopol monomethyl ether,2'-methylcarbonate;
1-Methylidene-2-(2'-hydroxy-4'-bromo-5'-methoxyphenyl)methylcyclohexane;
(3R)-Cyclocymopol monomethyl ether,2'-methylcarbonate;
(3R)-1-Debromocyclocymopol monomethyl ether,2'-benzoate;
(3R)-4'-Iodocyclocymopol monomethyl ether;
cis-1-Methylidene-2-(2'-hydroxy-4'-bromo-5'-methoxyphenyl)methyl-3,3-dimethyl-5-(propanal-1,3-dioxolane)cyclohexane;
cis-1-Methylidene-2-(2'-hydroxy-4'-bromo-5'-methoxyphenyl)methyl-3,3-dimethyl-5-(3-hydroxypropyl)cyclohexane;
(5R,6S)-1-Methylidene-6-(2'-acetoxy-4'-bromo-5'-methoxyphenyl)methyl-5-methyl-cyclohex-2-ene;
(3R)-5-Methyl-5,6-dehydro-1-debromocyclocymopol monomethyl ether, acetate;
1-Hydroxy-1-(4'-nitrophenyl)methyl-2-methylidene-4,6,6-trimethylcyclohex-3-ene;
cis-1-Methylidene-2-(2'-hydroxy-4'-bromo-5'-methoxyphenyl)methyl-3,3,5-trimethyl-cyclohexane;
1-Methylidene-6-(4'-nitrophenyl)thio-3,5,5-trimethylcyclohex-2-ene;
8-(2'-Acetoxy-4'-bromo-5'-methoxyphenyl)methyl-5,7,7-trimethylspiro[2.5]oct-4-ene;
1-Methylidene-4-(2'-hydroxy-4'-bromo-5'-methoxyphenyl)methyl-3,5,5-trimethylcyclohex-2-ene;
1-Methylidene-6-(benzofurazan-5'-yl)methyl-3,5,5-trimethylcyclohex-2-ene;
1-Methylidene-6-[trans-(2'-Hydroxy-4'-bromo-5'-methoxyphenyl)-1-propenyl]-3,5,5-trimethylcyclohex-2-ene;
trans-1-Methylidene-2-(2'-hydroxy-4'-bromo-5'-methoxyphenyl)methyl-3,3,5-trimethyl-5-(hydroxymethyl)cyclohexane;
trans-1-Methylidene-4-allyl-6-(2'-hydroxy-4'-bromo-5'-methoxyphenyl)methyl-5,5-dimethylcyclohex-2-ene;
trans-1-Methylidene-4-(2'-hydroxy)ethyl-6-(2"-hydroxy-4"-bromo-5"-methoxyphenyl)methyl-3,5,5-trimethylcyclohex-2-ene;
1-Methylidene-6-(2'-hydroxy-4'-bromo-5'-methoxyphenyl)methyl-3,5,5-trimethylcyclohex-2-ene;
trans-1-Methylidene-6-(2'-hydroxy-4'-bromo-5'-methoxyphenyl)methyl-4,5,5-trimethylcyclohex-2-ene;
trans-1-Methylidene-2-(2'-hydroxy-4'-bromo-5'-methoxyphenyl)methyl-3,3,4-trimethylcyclohexane;
6-(4'-Nitrophenyl)methyl-5,5-dimethylcyclohex-2-en-1-one; and
(3R)-4'-Formylcyclocymopol monomethyl ether.

Compounds comprising the class of cyclocymopol compounds and derivatives disclosed herein can be obtained by routine chemical synthesis by those skilled in the art, e.g., by modification of the cyclocymopol compounds disclosed or by a total synthesis approach.

The cyclocymopol compounds of this invention bind selectively to the progesterone receptor. We have found that the non-synthetic cyclocymopol compounds have agonist or antagonist activity depending on their stereoisomeric form. For example, the 3α or 3R diastereomer of cyclocymopol monomethyl ether has progesterone receptor antagonist activity, and the 3β or 3 S diastereomer of cyclocymopol monomethyl ether has progesterone receptor agonist activity. In contrast, other cyclocymopol analogs or derivatives have been found to predominently exhibit progesterone receptor antagonist activity regardless of their stereoisomeric form.

In the current invention, individual diastereomers of cyclocymopol monomethyl ether have been isolated from each other and purified in accordance with the following example.

EXAMPLE 1

The marine alga *Cymopolia barbata* (L.) Lamouroux (Dasycladaceae) was collected and frozen. Frozen sample was lyophilized and extracted with 1:1 MeOH/$CH_2Cl_2$ three times, and the extract was concentrated in vacuo to obtain an aqueous suspension of organic components. The concentrate was re-extracted with $CH_2Cl_2$ until no color came into the organic phase, and the $CH_2Cl_2$ extract was then concentrated to obtain the crude extract as a dark, green oil. The crude extract was purified by column chromatography on Sephadex LH20 with 1:1 MeOH/$CH_2Cl_2$, or vacuum flash chromatography on silica using a gradient of ethyl acetate in hexane, and the fractions were examined by thin layer chromatography (TLC). The fractions that contained cymopols were pooled together and separated by reversed phase high performance liquid chromatography (HPLC) using 80% MeOH/$H_2O$ to yield a mixture of cyclocymopol monomethyl ether diastereomers which were identified by nuclear magnetic resonance (NMR) spectroscopy as a mixture of the following as shown below:

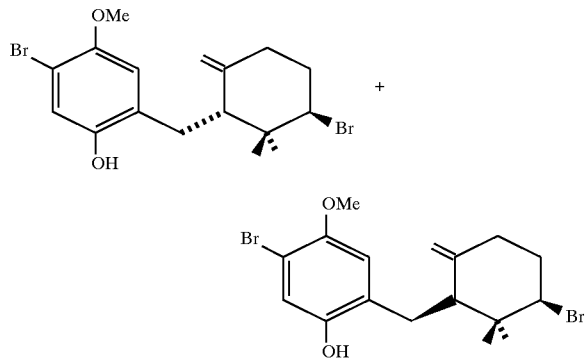

Cyclocymopol monomethyl ether diastereomers

Proton NMR spectrum of the cyclocymopol monomethyl ether mixture indicated the presence of the two diastereomers in the ratio 4:1. The two compounds could not be separated by reversed phase HPLC (ODS Column, 20% $H_2O$/MeOH solvent) where both migrated with the same retention.

The two compounds behaved similarly on normal phase HPLC (silica column, 5% EtOAc/hexane solvent), and an attempt to collect fractions inside the HPLC peak also failed to yield any separation. This indicated that the diastereomers of the mixture had very similar chromatographic behavior, even though diastereomers normally have different chromatographic characteristics.

In order to separate the diastereomers, the cyclocymopol monomethyl ether diastereomer mixture was reacted with acetic anhydride ($Ac_2O$) and pyridine at room temperature for about 10 hours. The resulting mixture of diastereomeric acetates was completely separated by normal phase HPLC (silica column, 5% EtOAc/hexane) to yield the individual chromatographically-pure diastereomers, as follows:

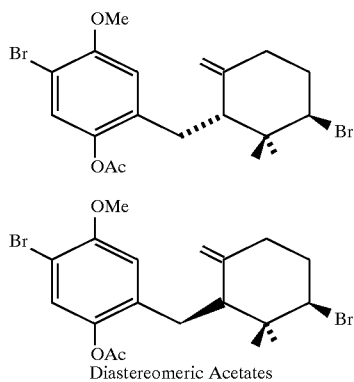

Diastereomeric Acetates

Figure 1B:
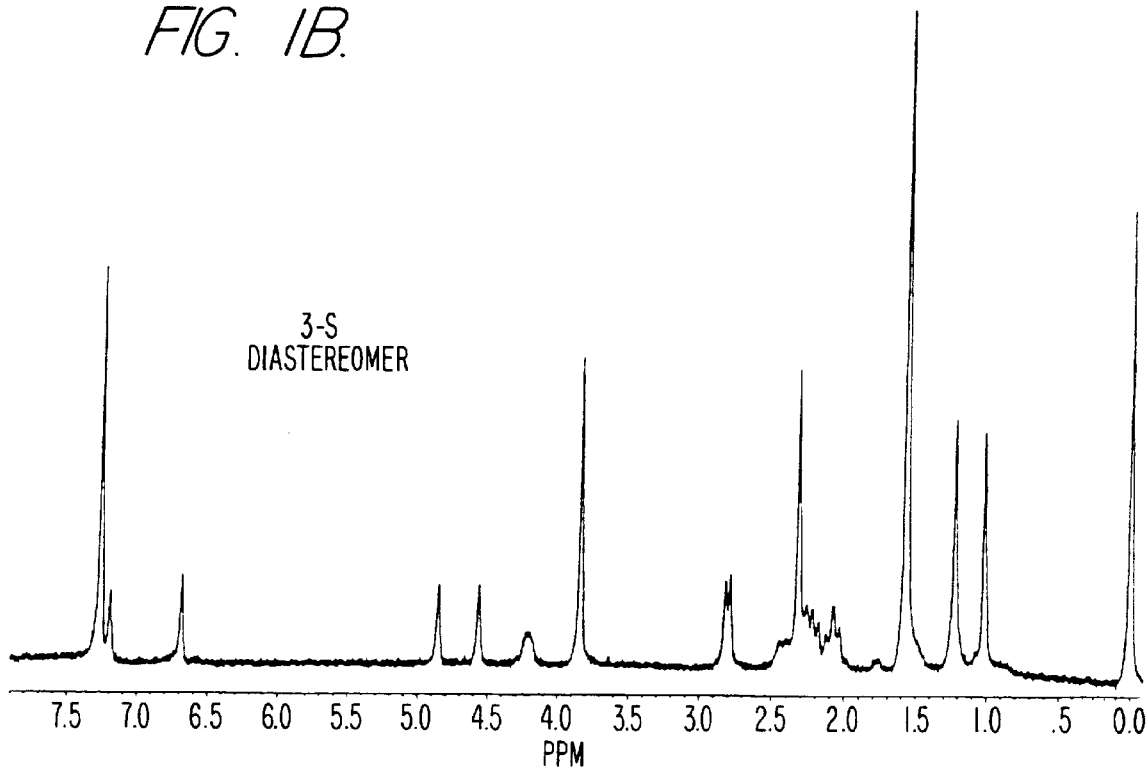

Proton NMR analysis confirmed that two separate spectroscopically-pure diastereomeric acetates were obtained, as shown in FIG. 1. The spectrum for the 3R diastereometric acetate is shown in panel a, and the spectrum for the 3S diastereometric acetate is shown in panel b of FIG. 1. The individual pure diastereomers were separately reacted with $K_2CO_3$ in MeOH to convert them back to the parent form, and the resultant products were purified by reversed phase HPLC using 80% MeOH/$H_2O$ to obtain the individual purified diastereomers of cyclocymopol monomethyl ether, as follows:

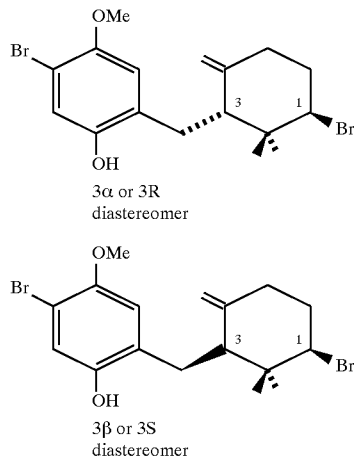

3α or 3R
diastereomer

3β or 3S
diastereomer

Proton NMR analysis of the resulting individual cyclocymopol monomethyl ether diastereomers also showed them to be spectroscopically pure. The 3R or 3α diastereomer was determined to have been the major component of the cyclocymopol monomethyl ether diastereomer mixture obtained from .C barbata.

Progesterone Receptor Activity

Utilizing the "cis-trans" or "co-transfection" assay described by Evans et al., Science, 240:889–95 (May 13, 1988), the two cyclocymopol monomethyl ether diastereomers were tested and found to have activity specifically for the intracellular receptor for progesterone. This assay is described in further detail in U.S. Pat. Nos. 4,981,784 and 5,071,773, which are incorporated herein by reference. The co-transfection assay provides a method for identifying functional ligands (either agonists which mimic, or antagonists which inhibit, the effect of hormones) for ligand-responsive receptor proteins.

The co-transfection assay provides a mechanism to evaluate ability of a compound to function as an agonist or antagonist of the activity modulated by an intracellular receptor. The co-transfection assay mimics an in vivo system in the laboratory. In the co-transfection assay, a cloned gene for an intracellular receptor is introduced by transfection (a procedure to induce cells to take up foreign genes) into a background cell substantially devoid of endogenous intracellular receptors. This introduced gene directs the recipient cells to make the intracellular receptor protein. A second gene is also introduced (co-transfected) into the same cells in conjunction with the intracellular receptor gene. This second gene functions as a reporter for the transcription-modulating activity of the target intracellular receptor. The reporter acts as a surrogate for the products normally expressed by a gene under control of the target receptor and its natural hormone.

A preferred reporter gene is one which expresses the firefly enzyme luciferase. The co-transfection assay can detect small molecule agonists or antagonists of target intracellular receptors. Exposing the cells to an agonist ligand increases reporter activity in the transfected cells that can be conveniently measured, reflecting ligand-dependent, intracellular receptor-mediated increases in reporter transcription. To detect antagonists, the co-transfection assay is carried out in the presence of a constant concentration of an agonist known to induce a defined reporter signal. Increasing concentrations of a test antagonist will decrease the reporter signal. The co-transfection assay is therefore useful to detect both agonists and antagonists of specific intracellular receptors. It determines not only whether a compound interacts with a particular intracellular receptor, but also whether this interaction mimics (agonizes) or blocks (antagonizes) the effects of the natural regulatory molecules on target gene expression.

Co-transfected cells are exposed to a medium to which is added the potential ligand that is being evaluated. If the candidate ligand diffuses into the cell and binds to the receptor and the resulting complex functions as an agonist, it binds to the co-transfected reporter gene and initiates transcription. When that gene is one that expresses, for example, luciferase, luciferase is produced which catalyzes a light-emitting reaction with its substrate luciferin. Thus, after cell lysis and the introduction of luciferin, the amount of light produced relative to the concentration of candidate ligand used in the assay provides a measure of the potency and efficacy of the compound tested. Antagonist activity is evaluated by adding the candidate ligand and a known agonist to the co-transfected cells. Suppression of agonist-induced luciferase production by the candidate compound, and hence the amount of light produced, indicates the candidate ligand is an antagonist.

The progesterone receptor activity of the cyclocymopol monomethyl ether disastereomer compounds were demonstrated according to the following illustrative example.

EXAMPLE 2

Cultured monkey kidney cells (CV-1's) were transfected with the human receptor cDNA for the progesterone receptor. The receptor cDNA was introduced in a mammalian expression vector under the control of the Rous Sarcoma virus LTR. These vectors provide for the efficient production of the progesterone receptor in these cells, which do not normally express this receptor gene. A reporter vector was also transfected, containing a firefly luciferase gene under the control of the hormone-responsive promoter. Addition of control hormone (progesterone) or agonist analogues (cyclocymopol compounds) enhanced transcription of the luciferase gene, resulting in an accumulation of the reporter protein luciferase in the cells, whereas antagonists inhibited luciferase production. The level of luciferase activity was then measured in cell extracts. Light emission is directly proportional to the effectiveness of the hormone-receptor complex in activating gene expression.

The cyclocymopol compounds were tested at eight concentrations ($10^{-4}$ to $10^{-11}$M) for the generation of a full dose response curve, and were compared to the progesterone control hormone response. A total of three replicates per concentration point were tested for each compound, and the $EC_{50}$ was calculated for each positive response. Both agonist and antagonist activity for each test compound was determined in parallel. In the antagonist assay, $10^{-8}$M progesterone was added to the media immediately prior to the addition of the cyclocymopol test compounds at the eight concentrations.

Figure 3A:
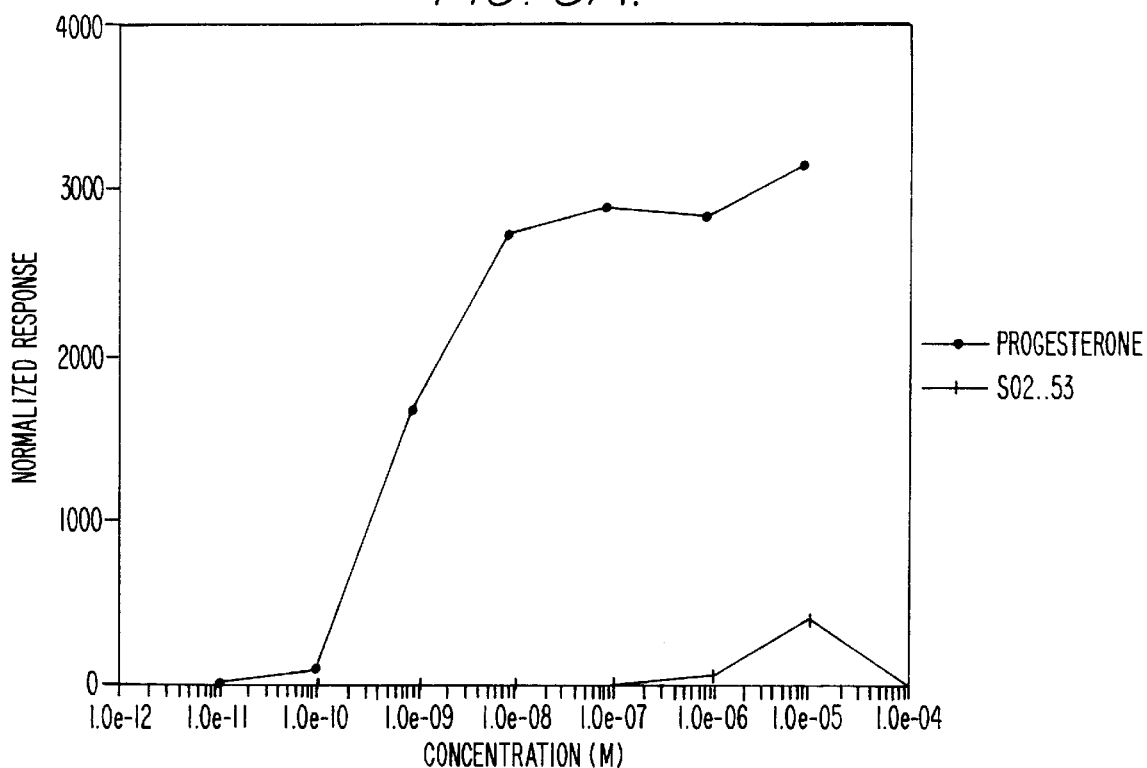
FIG. 3 presents activation profiles for analysis of progesterone receptor activation by (3R)-cyclocymopol monomethyl ether (compound SO53). For this compound and a progesterone control, agonist dose response is shown in panel a, and antagonist dose response is shown in panel b.
Figure 3B:
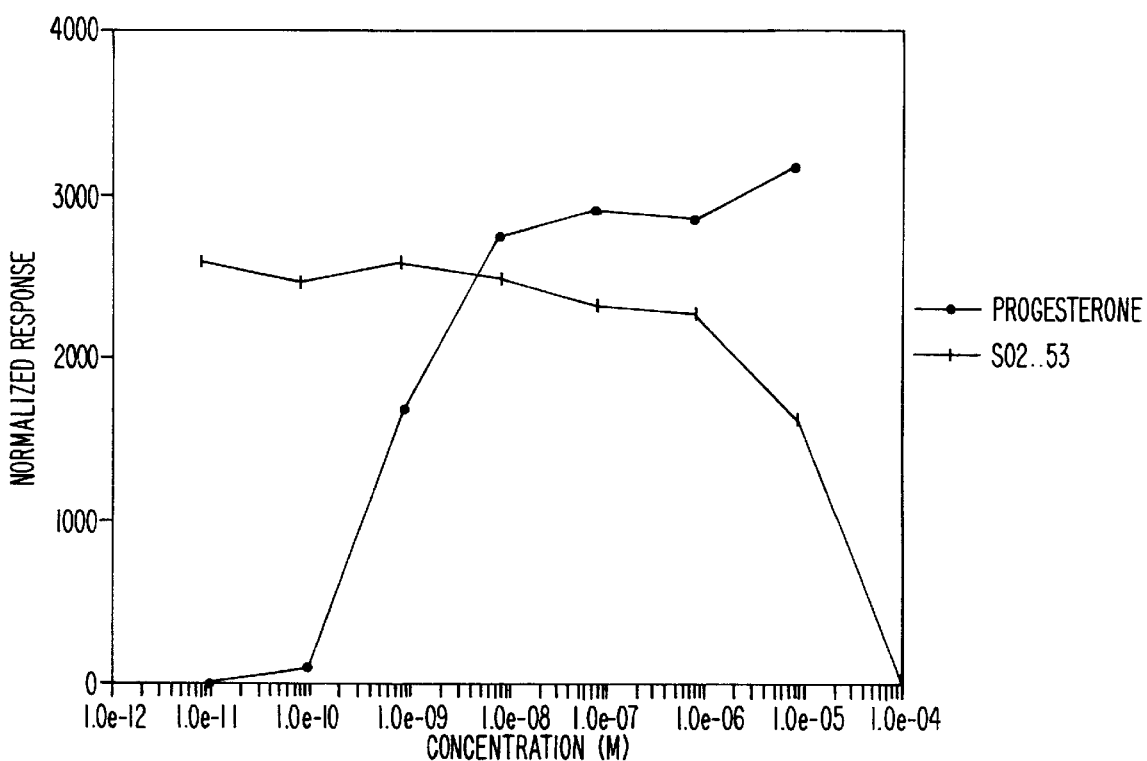
Figure 4A:
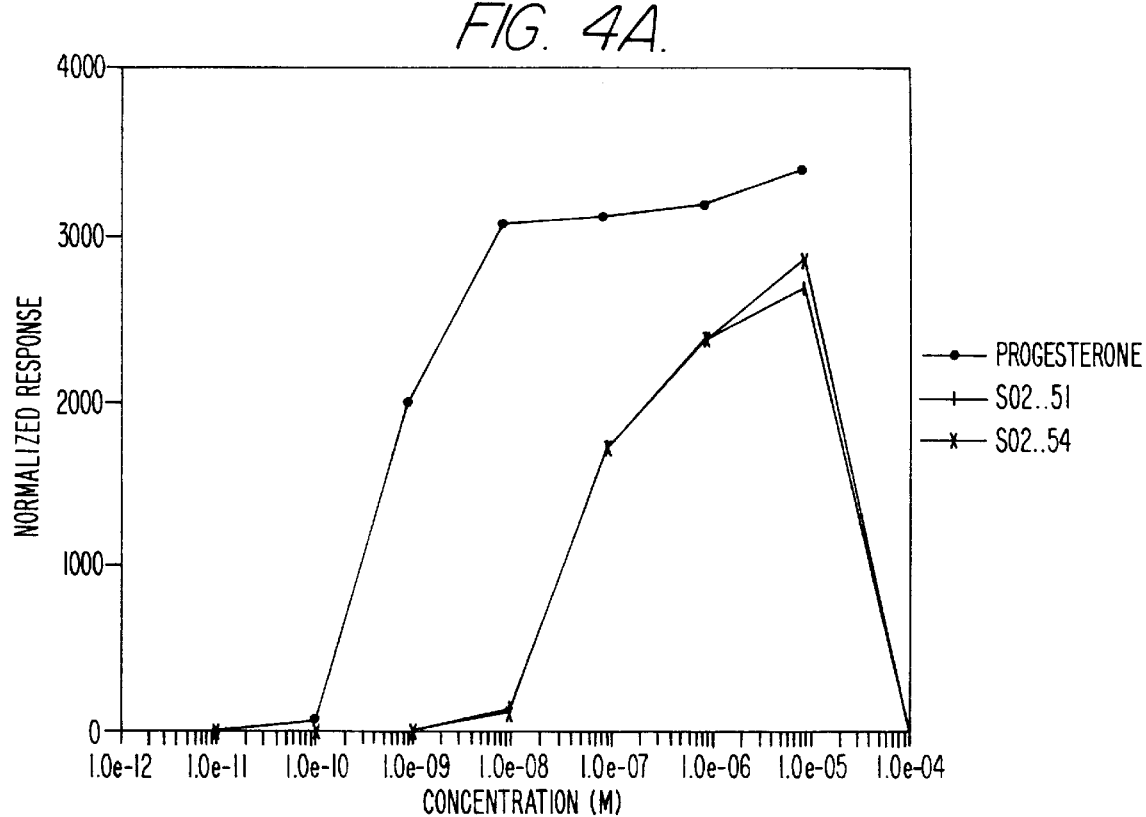
FIG. 4 presents activation profiles for analysis of progesterone receptor activation by (3S)-cyclocymopol monomethyl ether (compound SO-54) and its acetate (compound SO51). For these compounds and a progesterone control, agonist dose response is shown in panel a, and antagonist dose response is shown in panel b.
Figure 4B:
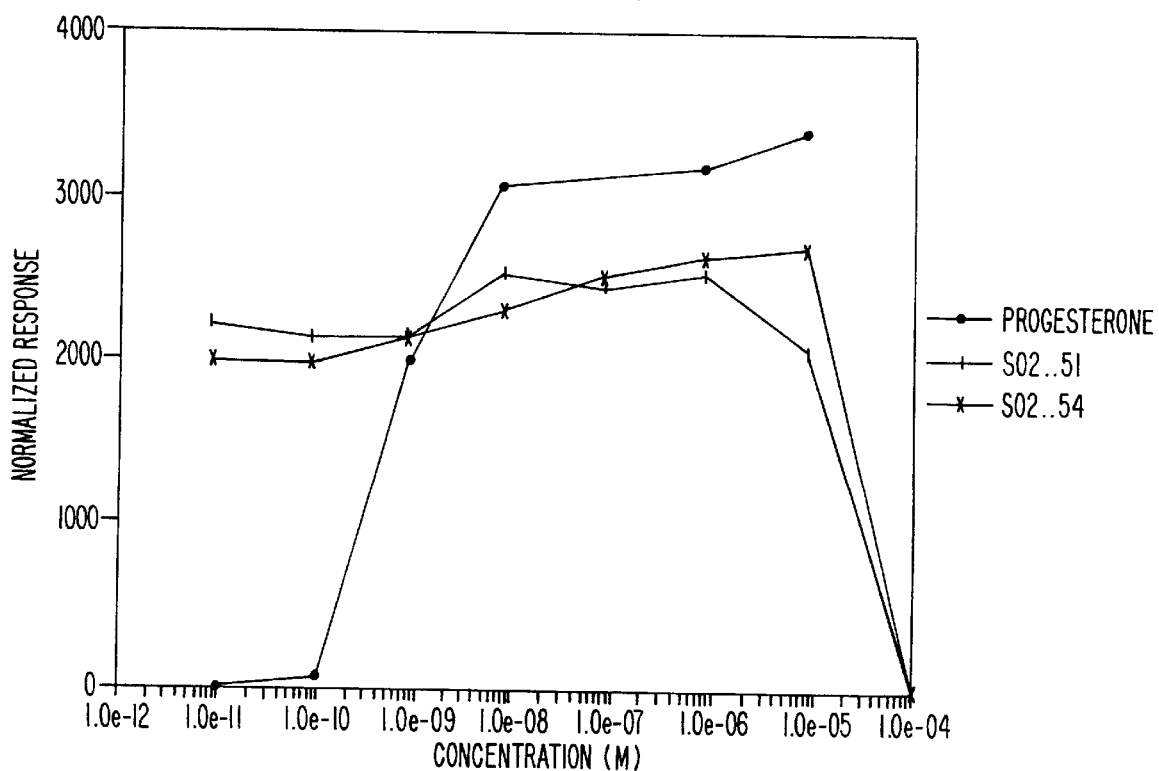
Figure 5A:
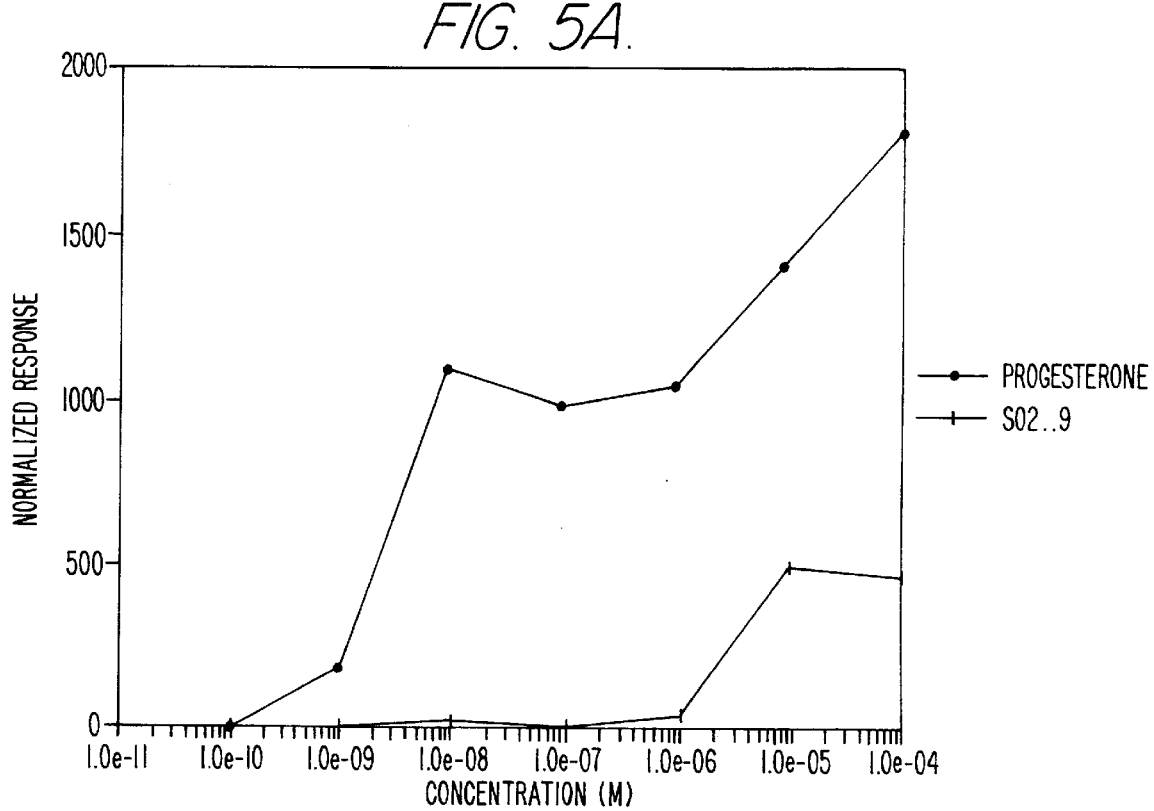
FIG. 5 presents activation profiles for analysis of progesterone receptor activation by (3R)-cyclocymopol monomethyl ether (compound SO-9). For this compound and a progesterone control, against dose response is shown in panel a and antagonist dose response is shown in panel b.
Figure 5B:
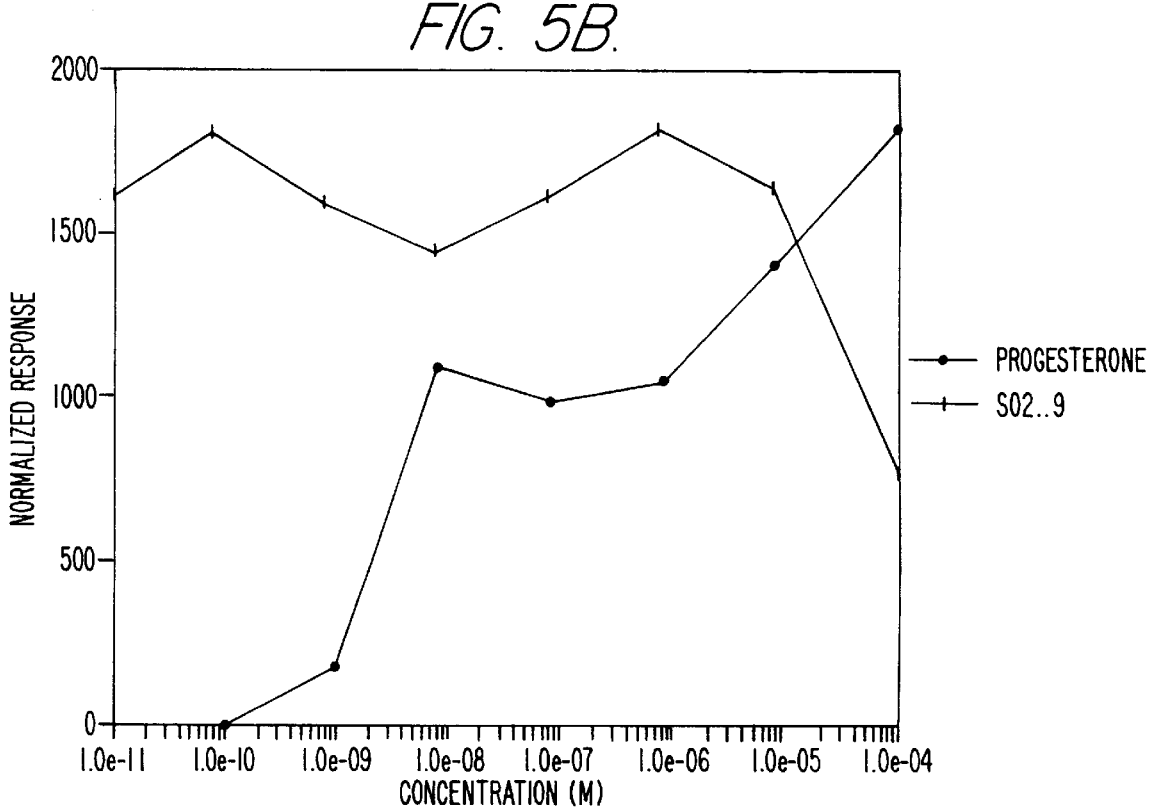

The assays showed a 3R (3α) and 3S (3β) diastereomer mixture of cyclocymopol monomethyl ether (designated compound SO-44) to have progesterone receptor antagonist activity, as shown in FIG. 2. (For FIG. 2, and for FIGS. 3 through 6, agonist dose response is shown in panel a, and antagonist dose response in panel b). As also shown in FIG. 2, the corresponding purified 3R diastereomeric acetate (designated SO-52) exhibited progesterone receptor antagonist activity, and a purified 3S diastereomeric acetate (designated SO-51) exhibited progesterone receptor agonist activity. These assays also showed that a 3R diastereomer of cyclocymopol monomethyl ether (designated SO-53) exhibited progesterone antagonist activity, as shown in FIG. 3. In contrast, the 3S diastereomer of cyclocymopol monomethyl ether (SO-54), and its acetate (SO-51), display progesterone receptor agonist activity, as shown in FIG. 4.

Compound SO-9 and the identical compound from a separate preparation, compound SO-53, exhibit progesterone receptor antagonist activity (see FIG. 5), and were tested for cross reactivity with the other known intracellular receptor classes, e.g., glucocorticoid, mineralocorticoid, androgen, estrogen, and retinoic acid. Compound SO-9 was also tested with orphan receptors (which are receptors whose natural ligand is unknown). The compound was found not to cross-react with any of the other receptors, which demonstrates that activity was limited to the progesterone receptor. FIG. 6 is illustrative, and shows that compound SO-9 demonstrated neither agonist nor antagonist activity with the glucocorticoid receptor, dexamethasone.

The 3R and 3S diastereomeric acetates of cyclocymopol monomethyl ether were also individually tested for cross reactivity with the other known intracellular receptor classes. This testing showed the 3R diastereomer to have slight agonist activity with the glucocorticoid receptor. No antagonist activity was detected with either compound.

To investigate the interaction of the cyclocymopol analogs with the human progesterone receptor, and to further demonstrate that they display ligand activity with the progesterone receptor, the analogs were tested for their ability to displace $^3$H-labeled progesterone from cell extracts containing the human progesterone receptor. These tests were conducted according to the following illustrative example.

EXAMPLE 3

A plasmid which expresses progesterone receptor was transfected into CV-1 cells by the method of calcium phosphate precipitation. After six hours, the cells were washed and incubated at 37° C. with 95% $O_2$ 5% $CO_2$ for 40 hours prior to harvest.

After incubation, cells were harvested and washed in phosphate buffered saline. Whole cell receptor extract was prepared by homogenizing the harvested cells in Tris-HCl buffer, pH=7.4, containing 30% glycerol, 1 mM EDTA, 12 mM monothioglycerol, 1 mM PMSF, and 0.5M potassium chloride. The homogenate was incubated at 4° C. for 60 min with resuspension every 10 min. The suspension was centrifuged (105,000×g, 60 min) and the supernatant was collected and flash frozen in liquid nitrogen and stored frozen at −70° C.

Aliquots of the whole cell extract containing transfected progesterone receptor was incubated at 4° C. for 24 hours with a constant concentration (5 nM) of tritiated progesterone and increasing concentrations (0–2.5×$10^{-5}$M) of either unlabeled cold progesterone or test compound. The concentration of bound tritiated progesterone was determined in each sample by the dextran-coated charcoal adsorption technique, as follows.

To a 500 l final volume incubation mixture, 400 l of 7.5% (w/v) dextran-coated charcoal suspension in gelatin phosphate buffer was added. The mixture was vortexed and incubated at 4° C. for 10 min and then centrifuged at 3000 rpm for 10 min. The amount of bound tritiated hormone was determined by liquid scintillation spectrophotometry of an aliquot of the supernatant.

Figure 7A:
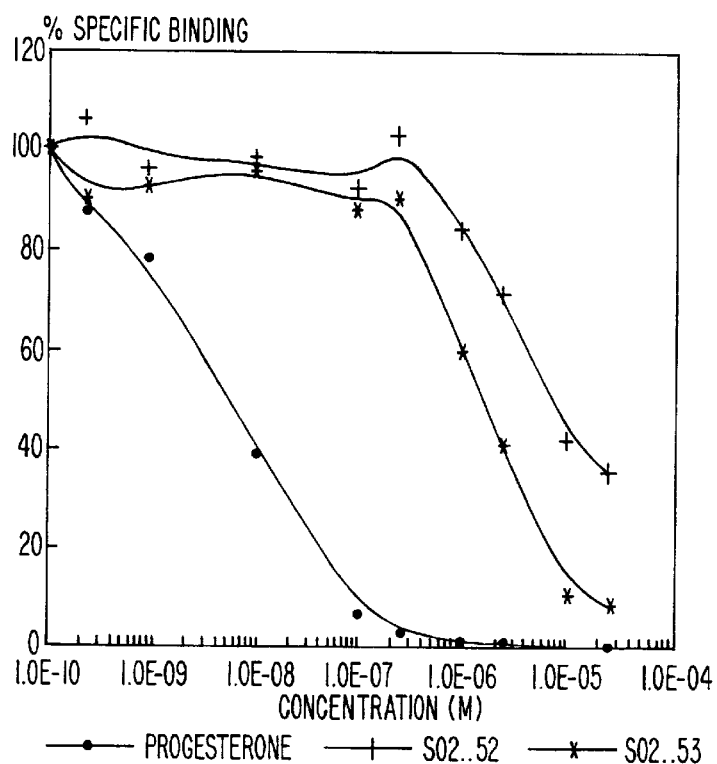
FIG. 7 presents profiles of displacement of $^3$H-labeled progesterone by cyclocymopol monomethyl ether diastereomers (panels a and b), and of the $^3$H-labeled progesterone agonist R5020 by RU486 and by a (3R)-cyclocymopol monomethyl ether compound (SO-9)
Figure 7B:
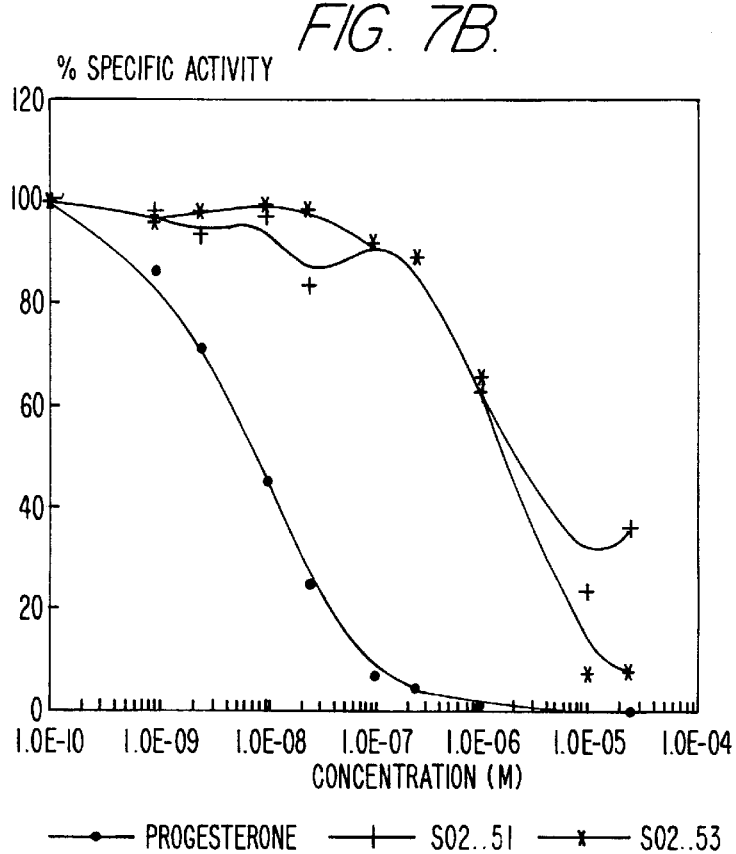
Figure 7C:
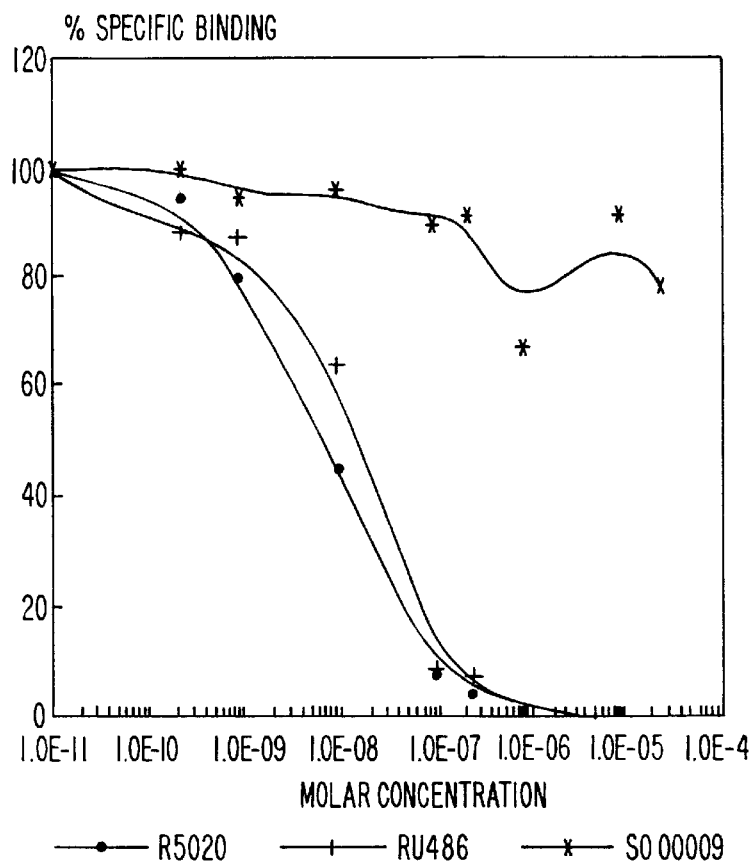

As shown in FIG. 7a, the purified 3R diastereomer of cyclocymopol monomethyl ether (compound SO-53) and its corresponding acetate (compound SO-52) displaced $^3$H-progesterone from its ligand binding site in a concentration-dependent manner. Similar binding isotherms were obtained with the purified 3S diastereomeric acetate of cyclocymopol monomethyl ether (compound SO-5 1), as shown in FIG. 7b. These compounds were between 2 and 3 orders of magnitude less potent than the endogenous hormone, progesterone. Similar binding studies were also carried out using the radiolabeled progesterone-agonist $^3$H-R5020, compound SO-9 (which is identical to compound SO-53), and the progesterone antagonist, RU486. As shown in FIG. 7c, RU486 was a competitive antagonist of R5020, whereas compound SO-9 did not compete for this binding site.

Figure 8A:
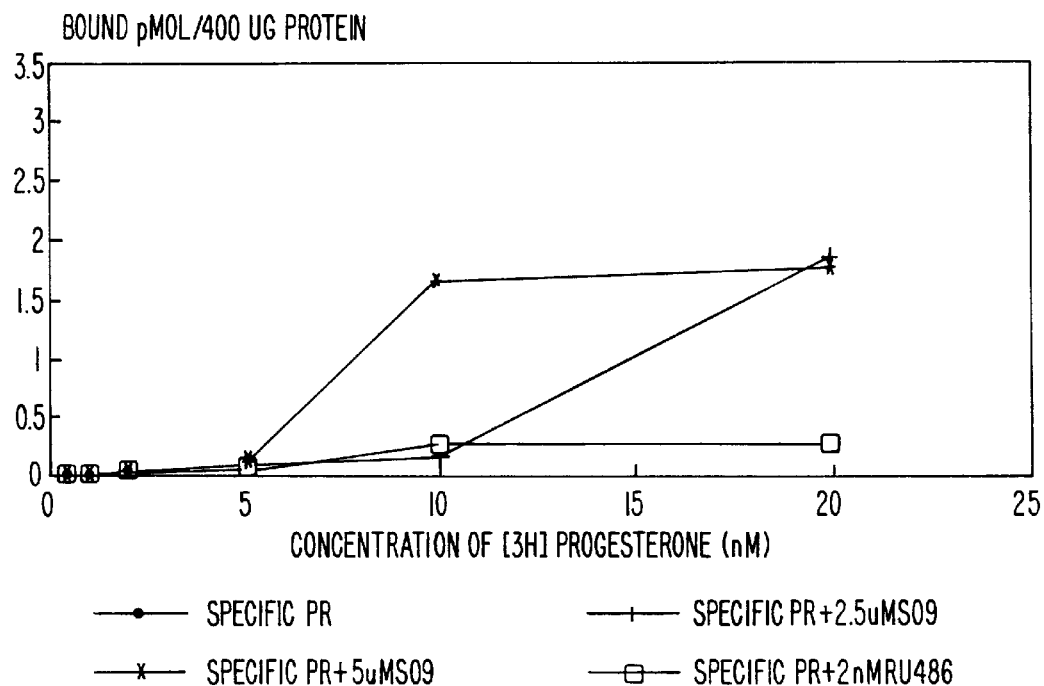
FIG. 8 presents profiles for analysis of progestrone binding for RU486 and (3R)-cyclocymopol monomethyl ether (compound SO-9)
Figure 8B:
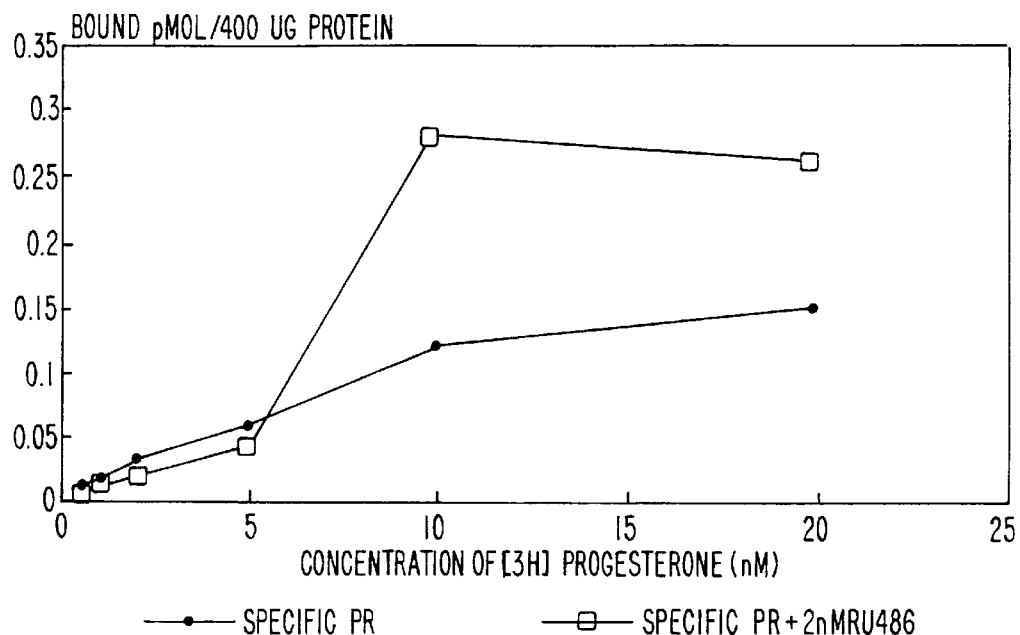

Progesterone receptor antagonists, such as RU486, can increase the specific binding of progesterone to its ligand binding site. This enigma was also observed upon performing binding studies with $^3$H-progesterone in the presence of compound SO-9. As shown in FIG. 8, this compound significantly increased the apparent Bmax of $^3$H-progesterone.

Figure 9:
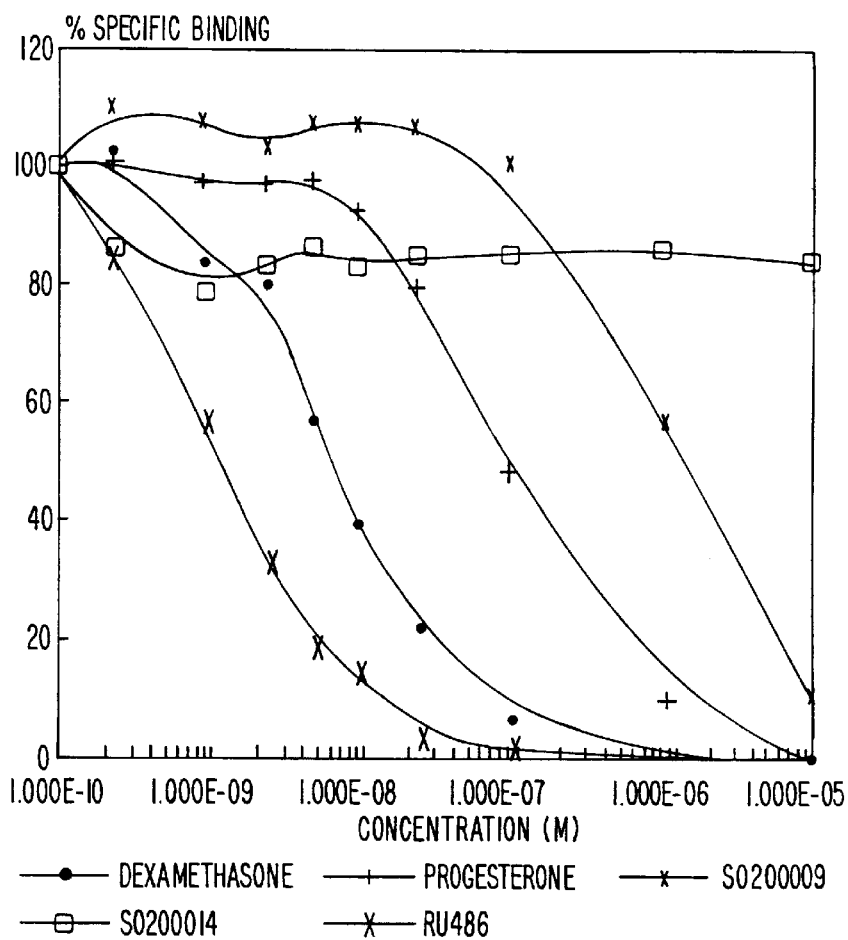
FIG. 9 presents profiles of the displacement of $^3$H-labeled dexamethasone from glucocorticoid receptor for several compounds.

Specificity of binding of progesterone agonists and antagonists has been studied by comparing the ability of various ligands to displace $^3$H-glucocorticoid from the human glucocorticoid receptor. The data in FIG. 9a illustrate that each of the ligands studied has affinity for the glucocorticoid receptor. The affinity of RU486 for the glucocorticoid receptor exceeds that of dexamethasone, and is 300-fold greater than that of compound SO-09. In fact, the affinity of RU486 for the glucocorticoid receptor is comparable to its affinity for the progesterone receptor.

The functional activities of the cyclocymopol analogues in the human breast cell line, T47D, were also investigated. T47D cells have proven to be a particularly useful model to investigate the molecular actions of sex steroids because they contain endogenous functional receptors for, and respond to, progestins, and their respective antagonists. Moreover, these cells contain exceptionally high titers of progesterone receptors and are exquisitely sensitive to the actions of progestins in a manner quite similar to their actions in normal and neoplastic mammary epithelial cells. In T47D cells, progestins induce de novo synthesis of a plasma-associated alkaline phosphatase, which has been reported to be similar, if not identical, to the alkaline phosphatase present in the normal breast and human milk. These tests were conducted according to the following illustrative example.

EXAMPLE 4

T47D cells were cultured in RPMI 1640 medium fortified with 10% fetal bovine serum, 2 mM glutamine, 0.2 ug/ml bovine insulin and, 0.05 mg/ml gentamicin. Cells were plated in 100-mm plates in medium; 48 hours later they were changed to medium containing 2% charcoal-treated serum with or without test compounds in a final ethanol concentration of 0.1%. For routine induction of alkaline phosphatase, cells were treated for three days with two media changes and harvested as described below.

Cells were collected with a rubber policeman into phosphate-buffered saline, pelleted, and lysed with TPSG buffer (0.2% Triton X-100 containing 10 mM sodium phosphate pH-7.4, 0.1M sucrose, and 10% glycerol) at 0° C. for 30 min with vigorous vortex mixing every 5 min. Nuclei were sedimented at 2500 rpm, and the supernatant was saved as cytosol. The protein content of the cytosol was assayed by the method of Bradford. Alkaline phosphatase activity was determined by incubating one volume of cell extract with three volumes of 1 mg/ml p-nitrophenol phosphate prepared in DEAM (1M diethanolamine, pH=9, containing 2 mM magnesium chloride) at room temperature for 20 min. At the end of the incubation time, the reaction was stopped with an equal volume of 1N NaOH. Ten standards of p-nitrophenol were prepared in DEAM buffer and absorbance was read at 405 nm. Alkaline phosphatase activity is expressed as pmol p-nitrophenol formed/min/mg protein.

Figure 10A:
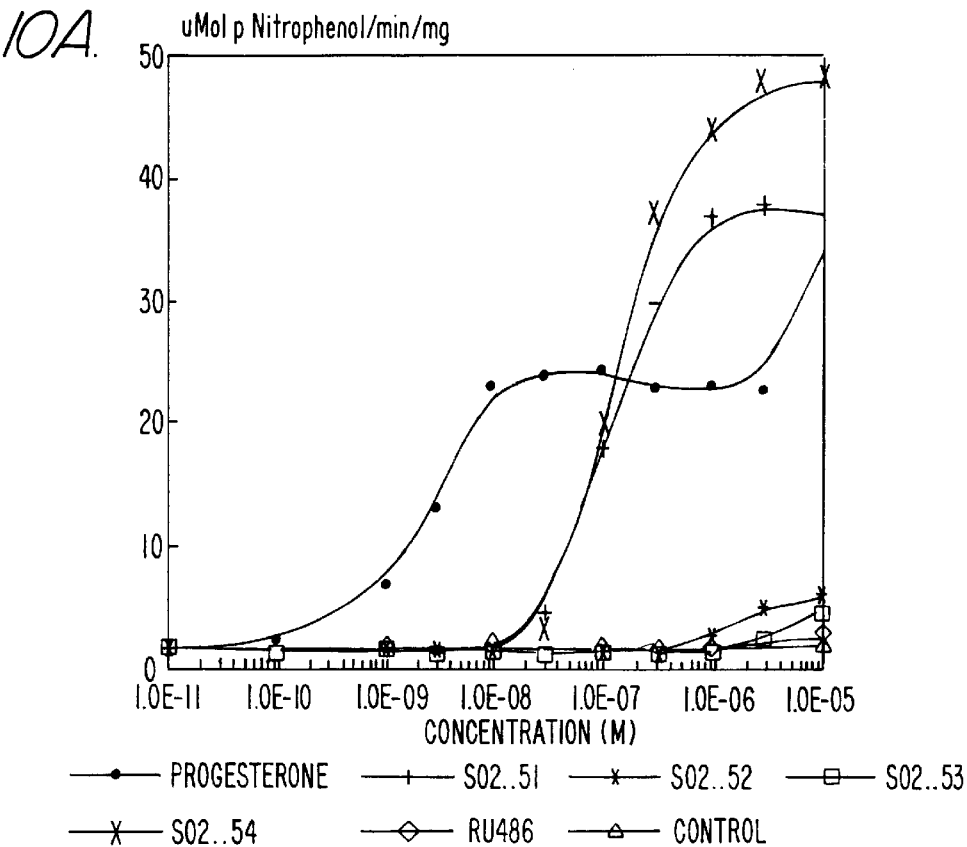
FIG. 10 presents profiles showing the functional activities of cyclocymopol analogues in T47D cells. Panel a shows ligand dependent induction of alkaline phosphatase in T47D cells by RU486 and cyclocymopol monomethyl ether diastereomers. Inhibition by (3R)-cyclocymopol monomethyl ether (SO-53) of progesterone-stimulated induction of alkaline phosphatase is shown in panel b, and of R5020 stimulated induction in panel c.

As shown in FIG. 10a, (3S)-cyclocymopol monomethyl ether (compound SO-54), and its corresponding acetate (compound SO-51), are functional agonists in this system, whereas (3R)-cyclocymopol monomethyl ether (compound SO-53), and its corresponding acetate (compound SO-52), appear to be very weak agonists. The 3S form compounds exhibit increased efficacy at higher concentrations, an effect which has been found to be reproducible.

Figure 10B:
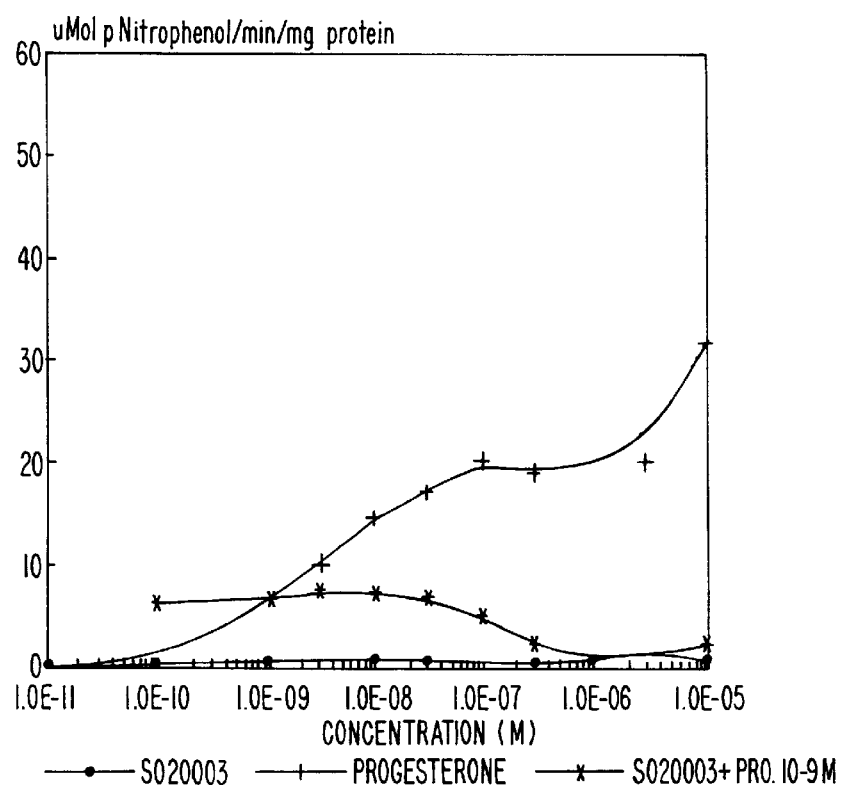
Figure 10C:
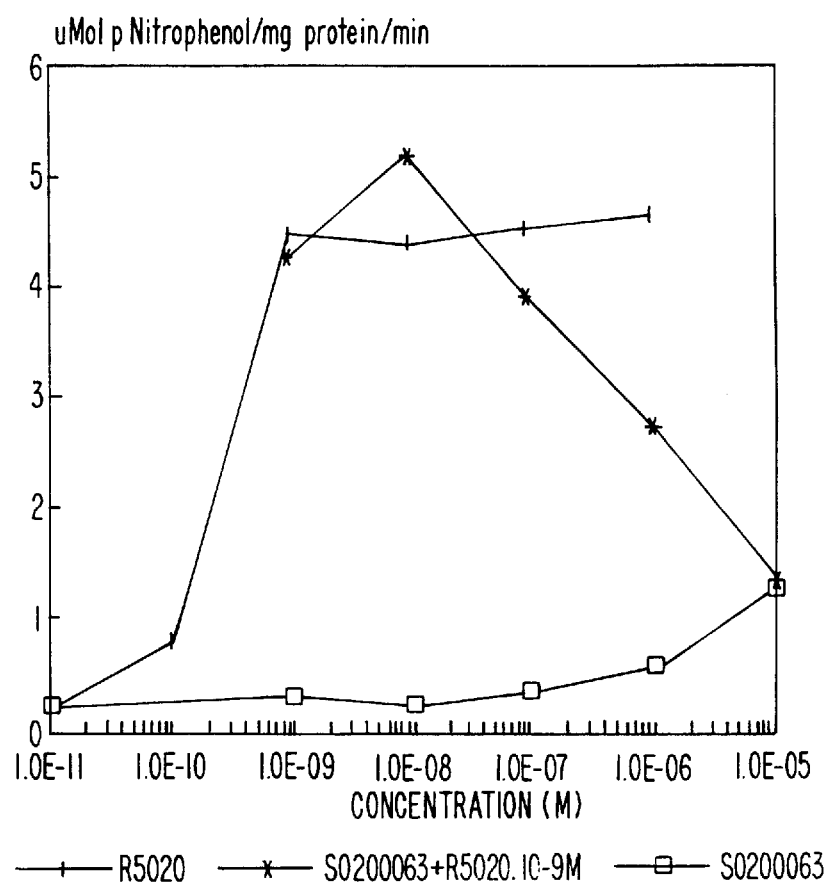

To determine if (3R)-cyclocymopol monomethyl ether could function as a progesterone receptor antagonist, the effects of increasing concentrations of this compound on R5020-induced alkaline phosphatase activity were quantified in T47D cells. As shown in FIGS. 10b and 10c, (3R)-cyclocymopol monomethyl ether (compound SO-53) is an effective antagonist of the progesterone mimic. Similarly, when alkaline phosphatase activity was stimulated by 1.0 nM progesterone, (3R)-cyclocymopol monomethyl ether (compound SO-53) attenuated this induction in a concentration-dependent manner.

Figure 11A:
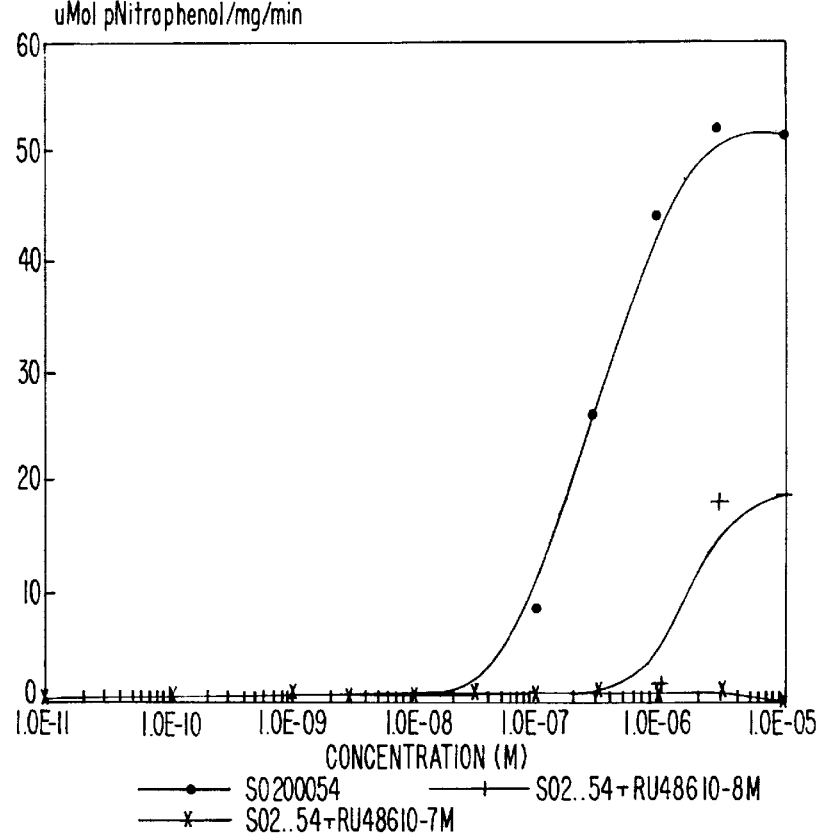
FIG. 11 presents profiles showing the inhibition by RU486 of induction of alkaline phosphatase in T47D cells by (3S)-cyclocymopol monomethyl ether (SO-54) in panel a and by its acetate (SO-5 1) in panel b.
Figure 11B:
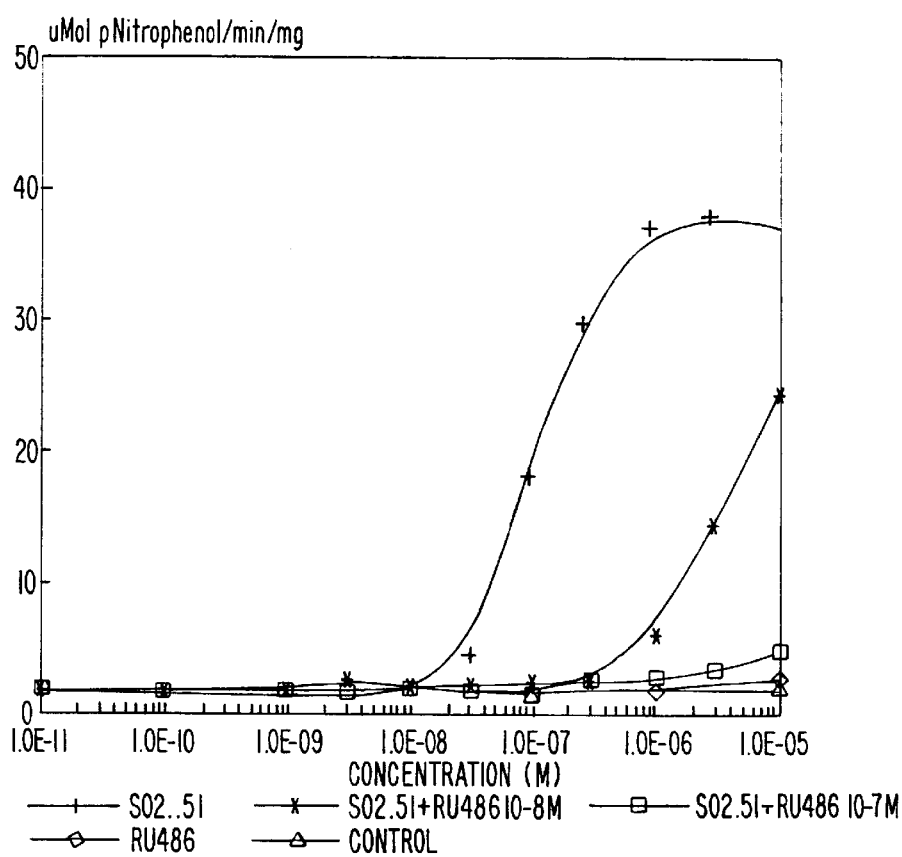

In comparison, the progesterone agonist, (3S)-cyclocymopol monomethyl ether (compound SO-54), and its acetate (SO-51), increased the activity of intracellular alkaline phosphatase in a concentration-dependent manner, and this was blocked by the progesterone antagonist, RU486, as shown in FIG. 11. In this system, (3R)-cyclocymopol monomethyl ether (compound SO-53) functioned as a progesterone receptor antagonist and attenuated the effects of progesterone in a concentration-dependant manner.

Synthetic and semisynthetic cyclocymopol analogs have been prepared which also have activity for the intracellular receptor for progesterone. Representative analogs of the present invention are prepared according to the following illustrative synthetic schemes and illustrative examples.

EXAMPLE 5

Synthesis of First Aromatic Subunit
2-Acetoxy-5-methoxybenzaldehyde (1)

To a flame-dried 50 mL round-bottomed flask containing 10.00 g (65.7 mmol) 2-hydroxy-5-methoxybenzaldehyde in 10 mL dry pyridine at 0° C. under nitrogen atmosphere was added 7 mL acetic anhydride. The reaction mixture was then allowed to warm to room temperature and continually stirred until TLC analysis indicated complete consumption of starting material (50 min). Ethyl acetate (150 mL) was added, and the mixture was then transferred to a separatory funnel and successively washed with 1N HCl (3×50 mL), saturated aqueous NaHCO$_3$ (1×50 mL), and brine (1×50 mL), dried over Na$_2$SO$_4$, and concentrated under reduced pressure to give 12.41 g (97%) of the acetylated phenol as a white solid. The product thus obtained was homogenous by TLC (Rf 0.41, 2:1 hexane/ethyl acetate), and was carried on to the next step without further purification.

2-Acetoxy-4-bromo-5-methoxybenzaldehyde (2)

To a 500 mL round-bottomed flask containing a solution of 20.0 g (168.1 mmol, 3.26 equiv) potassium bromide and 3.21 mL (10.0 g, 62.6 mmol, 1.21 equiv) bromine in 200 mL water at room temperature was added 10.00 g (51.5 mmol, 1.0 equiv) 2-acetoxy-5-methoxybenzaldehyde (1) as a finely divided white powder, portionwise over a period of 35 min. After 18 h stirring at room temperature, the reaction mixture was filtered under vacuum using a Büchner funnel to give 10.59 g (89%) of the aryl bromide as a pale yellow solid (Rf 0.45, 2:1 hexanes/ethyl acetate). The product thus obtained was of greater than 98% purity by $^1$H NMR, and homogenous by TLC, and was carried on to the next step without further purification. A portion of the crude product was recrystallized from 5:1 ether/hexanes to give white needles. $^1$H NMR (400 MHz, CDCl$_3$) δ 2.37 (s, 3H, COCH$_3$), 3.93 (s, 3H, OCH$_3$), 7.36 and 7.46 (2s, 2×1H, Ar—H), 10.08 ppm (s, 1H, CHO).

2-Hydroxy-4-bromo-5-methoxybenzaldehyde (3)

To a 200 mL round-bottomed flask containing 6.90 g (25.3 mmol) 2 acetoxy-4-bromo-5-methoxybenzaldehyde (2) in 100 mL of 1% aqueous methanol at room temperature was added 5 g K$_2$CO$_3$, and the mixture was allowed to stir at room temperature for 1 h, at which time TLC analysis indicated complete consumption of starting material and the presence of a slightly more polar compound as the only detectable product. The reaction mixture was then neutralized to pH 5 with the addition of 1N HCl, and the solvent was subsequently removed under diminished pressure. The residue was then dissolved in ethyl acetate (200 mL), washed successively with 1N HCl (1×50 mL), saturated aqueous NaHCO$_3$ (1×50 mL), and brine (1×50 mL), dried over Na$_2$SO$_4$, and concentrated under diminished pressure to give 4.97 g (85%) of the bromophenol as a brownish-red oily solid. A portion of this crude material was recrystallized from 2:1 hexanes/ethyl acetate to give white needles. $^1$H NMR (400 MHz, CDCl$_3$) δ 3.89 (s, 3H, OCH$_3$), 6.97 and 7.27 (2s, 2×1H, Ar—H), 9.83 (s, 1H, OH), 10.71 ppm (s, 1H, CHO). The remainder of the material was carried on to the next step without further purification.

2-(tert-Butyl)dimethylsilyloxy-4-bromo-5-methoxybenzaldehyde (4)

To a flame-dried 100 mL round-bottomed flask containing 2.76 g (11.95 mmol) 2-hydroxy-4-bromo-5-methoxybenzaldehyde (3) in 50 mL anhydrous dichloromethane under nitrogen atmosphere at room temperature was added 2.03 g (29.88 mmol, 2.50 equiv) imidazole, 2.25 g (14.94 mmol, 1.25 equiv) (tert-Butyl)dimethylchlorosilane, and DMAP (100 mg, catalytic). The mixture was allowed to stir at room temperature for 75 min, at which time TLC analysis indicated complete consumption of starting material, and the formation of a less polar product (Rf 0.75, 2:1 hexanes/ethyl acetate). The reaction mixture was then poured into a separatory funnel containing 50 mL dichloromethane and 50 mL saturated aqueous NH$_4$Cl, the layers were separated, and the organic phase was washed with 50 mL brine, dried over Na$_2$SO$_4$, and concentrated under diminished pressure to give 4.13 g (quantitative) of the silylated bromophenol as an off-white solid, a portion of which was recrystallized from 3:1 hexanes/ether to give an amorphous white solid. $^1$H NMR (400 MHz, CDCl$_3$) δ 0.27 [s, 6H, Si(CH$_3$)$_2$], 1.02 [s, 9H, SiC(CH$_3$)$_3$], 3.89 (s, 3H, OCH$_3$), 7.14 (s, 1H, 6-H),728 (s, 1H, 3-H), 10.35 ppm (s, 1H, CHO); $^{13}$C NMR (100.61 MHz, CDCl$_3$) δ −4.4, 18.3, 25.7, 56.6, 108.9, 120.1, 125.6, 126.5, 151.0, 152.9, 189.1 ppm.

2-(tert-Butyl)dimethylsilyloxy-4-bromo-5-methoxybenzyl alcohol (5)

To a flame-dried 200 mL round-bottomed flask containing 4.10 g (13.14 mmol) 2-(tert-butyl)dimethylsilyloxy-4-bromo-5-methoxybenzaldehyde (4) in 100 mL anhydrous methanol at 0° C. was added 0.50 g (13.15 mmol, 1.0 mol equiv) NaBH$_4$ over a period of 3 min. After 20 min at 0° C., TLC analysis indicated complete consumption of starting material, and the formation of a more polar product (Rf 0.42, 2:1 hexanes/ethyl acetate). Water (75 mL) was added, and the methanol was removed by rotary evaporation. The resultant aqueous residue was extracted with ethyl acetate (2×100 mL), and the combined organic layers were dried over Na$_2$SO$_4$, and concentrated under diminished pressure. Purification by flash column chromatography (silica gel, hexanes/ethyl acetate, 5:1) afforded 4.10 g (98%) of the benzylic alcohol as a white solid. $^1$H NMR (400 MHz, CDCl$_3$) δ 0.23 [s, 6H, Si(CH$_3$)$_2$], 1.00 [s, 9H, SiC(CH$_3$)$_3$], 386 (s, 3H, OCH$_3$), 4.61 (s, 2H, CH$_2$OH), 692 (s,1H), 6.97 ppm (s, 1H, 3-H).

2-(tert-Butyl)dimethylsilyloxy-4-bromo-5-methoxybenzyl bromide (6)

To a flame-dried 100 mL round-bottomed flask containing triphenylphosphine (1.27 g, 4.84 mmol, 1.05 equiv) in 25 mL anhydrous DMF at 0° C. under nitrogen atmosphere was added bromine (0.24 mL, 4.84 mL, 1.05 equiv, plus enough extra to cause a persistent reddish tint to the solution, 1 drop) through an additional funnel. To this reaction mixture was added 2-(tert-butyl)dimethylsilyloxy-4-bromo-5-methoxybenzyl alcohol (5) through the addition funnel at a steady rate over 30 min, as a solution in 10 mL DMF. The reaction mixture was allowed to stir at 0° C. for 60 min, at which time TLC analysis indicated complete consumption of starting material, and the formation of a less polar product (Rf 0.81, 2:1 hexanes/ethyl acetate). Hexane (100 mL) was then added, and the contents of the flask were transferred to a separatory funnel containing 50 mL of saturated aqueous NH$_4$Cl, rinsing with an additional 50 mL hexane and 10 mL water. The layers were separated, and the organic phase was washed with 20 mL 10% Na$_2$S$_2$O$_3$, dried over Na$_2$SO$_4$, and concentrated under diminished pressure. Purification by trituration at 0° C. (2×30 mL ea. hexane) to remove residual triphenylphosphine oxide, followed by flash column chromatography (silica gel, hexane/ethyl acetate, gradient elution) afforded 1.51 g (80%) of the benzylic bromide as a colorless, viscous oil. $^1$H NMR (400 MHz, CDCl$_3$) δ 0.28 [s, 6H, Si(CH$_3$)$_2$], 1.05 [s, 9H, SiC(CH$_3$)$_3$], 387 (s, 3H, OCH$_3$), 4.48 (s, 2H CH$_2$Br), 6.79 and 7.01 ppm (2s, 2×1H, Ar—H).

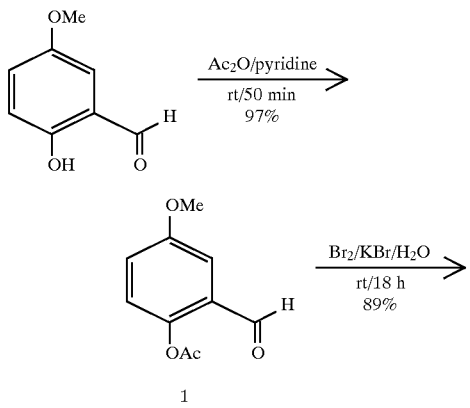

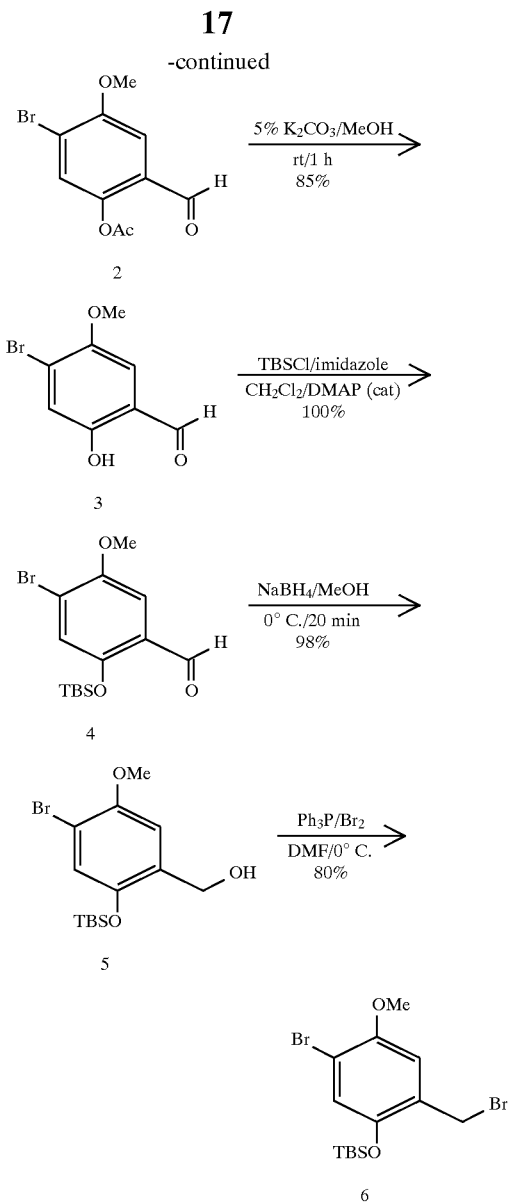

EXAMPLE 6

Synthesis of First Aliphatic Subunit
3-Ethoxy-5,5-dimethylcyclohex-2-en-1-one (7)

To a flame-dried 1 L round-bottomed flask containing 15.0 g (107 mmol) 5,5-dimethylcyclohexane-1,3-dione and 120 mL absolute ethanol in 300 mL anhydrous benzene under nitrogen atmosphere was added 750 mg p-toluenesulphonic acid monohydrate (catalytic). The flask was fitted with a Dean Stark trap for removal of water, and a reflux condenser, and the mixture was heated to reflux for 9 h. Upon cooling to room temperature, the solvent was removed by rotary evaporation, and the residue was dissolved in 300 mL ethyl acetate. The organic solution was then washed successively with 10% aqueous NaOH (2×100 mL), water (1×100 mL), and brine (1×100 mL), dried over $Na_2SO_4$, and concentrated under diminished pressure to give 16.5 g (92%) of the keto-enol ether as a pale yellow oil (Rf 0.24, 2:1 hexanes/ethyl acetate) of greater than 98% purity by $^1H$ NMR. $^1H$ NMR (400 MHz, $CDCl_3$) δ 1.08 (s, 6H, germinal-$CH_3$'s), 1.38 (dd, 3H, $OCH_2CH_3$), 2.21 and 2.28 [2s, 2×2H, 6-H, 4-H), 3.90 (q, 2H, $OCH_2CH_3$), 5.32 ppm (s, 1H, 2-H).

5,5-Dimethylcyclohex-2-en-1-one (8)

To a flame-dried 100 mL round-bottomed flask containing lithium aluminum hydride (0.95 g, 24.4 mmol, 0.5 mol equiv) in 35 mL anhydrous ether under nitrogen atmosphere at 0° C. was added 8.20 g (48.7 mmol) 3-ethoxy-5,5-dimethylcyclohex-2-en-1-one (7) portionwise through a syringe as a solution in 10 ml anhydrous ether. The reaction mixture was allowed to warm to room temperature, and after 4 h, TLC analysis indicated complete consumption of starting material. The reaction mixture was then cooled to 0° C. before the cautious addition of 50 mL water, and the contents of the flask were then poured into a 500 mL Erlenmeyer flask containing 150 mL ice-cold 10% $H_2SO_4$. The mixture was then extracted with ether (2×200 mL), and the combined organics were washed successively with water (100 mL), and saturated aqueous $NaHCO_3$ (100 mL), dried over $Na_2SO_4$, and concentrated under diminished pressure to give 6.05 g (quantitative) of the dimethylenone (Rf 0.55, 2:1 hexane/ethyl acetate). $^1H$ NMR (400 MHz, $CDCl_3$) δ 1.05 (s, 6H, geminal-$CH_3$'s), 2.23 (dd, 2H, $CHCH_2$), 2.28 (s, 2H, $COCH_2$), 6.03 (ddd, 1H, 2-H), 6.87 ppm (ddd, 1H, 3-H).

3-Ethoxy-6,5,5-trimethylcyclohex-2-en-1-one (9)

To a flame-dried 300 mL round-bottomed flask containing diisopropylamine (1.83 mL, 13.06 mmol, 1.1 equiv) in 50 mL anhydrous THF at −78° C. under nitrogen atmosphere was added n-butyllithium (5.70 mL of a 2.2M solution in hexane, 12.50 mmol, 1.05 equiv). After 20 min at −78° C., 3-ethoxy-5,5-dimethylcyclohex-2-en-1-one (7) was added as a solution in 3 mL THF, and the reaction mixture was allowed to stir at that temperature for 15 min before gradual warming to 0° C., and subsequent addition of iodomethane (3.5 mL, 59.5 mmol, 5 equiv). The reaction mixture was then allowed to warm to room temperature, and after 3 h, was quenched which saturated aqueous $NH_4Cl$. The contents of the flask were then extracted with 100 mL ethyl acetate, and the organic phase was washed successively with water (50 mL) and brine (50 mL), dried over $Na_2SO_4$, and concentrated under diminished pressure. Purification by flash column chromatography (silica gel, hexane/ethyl acetate, gradient elution) afforded 1.94 g (90%) of the methylated keto-enol ether (Rf 0.40, 2:1 hexanes/ethyl acetate) as a colorless oil. $^1H$ NMR (400 MHz, $CDCl_3$) δ 0.93 and 1.08 (2s, 2×3H, geminal-$CH_3$'s), 1.07 (d, 3H, $CHCH_3$), 1.36 (t, 3H, $OCH_2CH_3$), 2.14 (dd, 1H), 2.29 (dd,2H), 3.88 (dq, 2H, $OCH_2CH_3$), 5.30 ppm (s, 1H, 2-H), 4,5,5-Trimethylcyclohex-2-en-1-one (10)

This compound was prepared from 3-ethoxy-6,5,5-trimethylcyclohex-2-en-1-one (9) (1.60 g, 8.80 mmol) in the manner previously described for enone 8, yielding 1.03 g (85%) of the methylated enone as a colorless oil. $^1H$ NMR (400 MHz, $CDCl_3$) δ 0.90 and 1.07 (2s, 2×3H, geminal-$CH_3$'s), 1.10 (d, 3H, $CHCH_3$), 5.96 (dd, 1H, 2-H), 6.16 ppm (dd, 1H, 3-H).

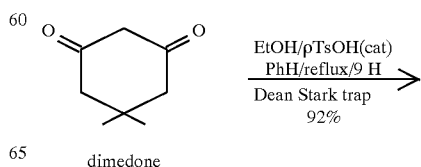

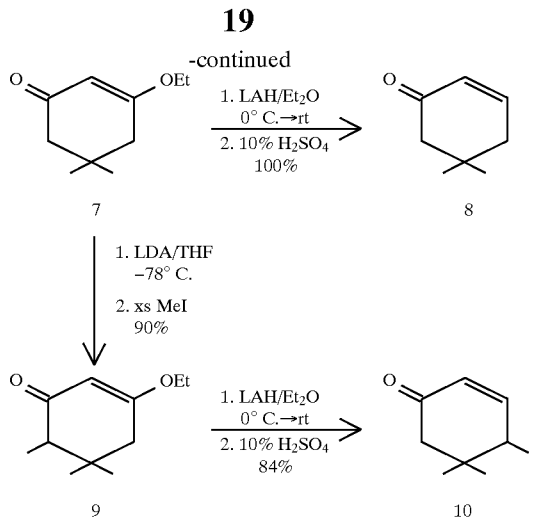

Synthesis of Cyclocymopol Analogs

EXAMPLE 7

6-[2'-(tert-Butyl)dimethylsilyloxy-4'-bromo-5'methoxyphenyl]methyl-5,5-dimethylcyclohex-2-en-1-one (11)

To a flame-dried 50 mL round-bottomed flask containing diisopropylamine (0.188 mL, 1.34 mmol, 1.1 equiv) in 10 mL anhydrous THF at −78° C. under nitrogen atmosphere was added n-butyllithium (0.58 mL of a 2.2M solution in hexane, 1.28 mmol, 1.05 equiv). After 20 min at −78° C., 5,5-dimethylcyclohex-2-en-one (8) (0.151 g, 1.22 mmol) was added as a solution in 1 mL of THF, and the reaction mixture was allowed to stir at that temperature for 15 min, at which time the cooling bath was removed. When the temperature of the reaction mixture (monitored using a thermocouple probe) reached −5° C., 2-(tert-butyl)dimethylsilyloxy-4-bromo-5-methoxybenzyl bromide (6) (1.00 g, 2.44 mmol, 2.0 equiv) was added all at once as a solution in 2 mL THF. The reaction mixture was then allowed to warm to room temperature, and after 3 h, TLC analysis indicated complete consumption of the enone starting material, and the formation of a product of intermediate polarity with respect to the two starting components (Rf 0.59, 2:1 hexanes/ethyl acetate), and the reaction was quenched by the addition of 5 mL saturated aqueous NH$_4$Cl. The contents of the flask were transferred to a separatory funnel, and extracted with 60 mL ethyl acetate, and the resultant organic phase was washed with 30 mL brine, dried over Na$_2$SO$_4$, and concentrated under diminished pressure. Purification by flash column chromatography (silica gel, hexane/ethyl acetate, gradient elution) afforded 0.459 g (83%) of the benzylated enone as a colorless, viscous oil, which solidified on standing. $^1$H NMR (400 MHz, CDCl$_3$) δ 0.21 and 0.23 [2s, 2×3H, Si(CH$_3$)$_2$], 1.00 [s, 9H, SiC(CH$_3$)$_3$], 1.02 and 1.03 (2s, 2×3H, geminal-CH$_3$'s), 2.25 2.32 (ddd of ABq 2H, 4-H), 2.51 (dd, 1H, 6-H), 2.78 and 2.88 (d of ABq, 2H, benzylic-CH$_2$), 3.80 (s, 3H, OCH$_3$), 5.96 (ddd, 1H, 2-H), 6.68 (s, 1H, 6'-H), 6.77 (ddd, 1H, 3-H), 6.94 ppm (s, 1H, 3'-H).

2-[2'-(tert-Butyldimethylsilyloxy-4'-bromo-5'-methoxyphenyl]methyl-3,3-dimethylcyclohexanone (12)

To a flame-dried 100 mL round-bottomed flask containing 6-[2'-(tert-butyl)dimethylsilyloxy-4'-bromo-5'-methoxyphenyl]methyl-5,5-dimethylcyclohex-2-en-1-one (11) (0.154 g, 0.454 mmol) in 22 mL ethyl acetate (which had been pre-dried over K$_2$CO$_3$) at room temperature was added 20 mg 5% palladium on carbon, and after flushing/evacuating the vessel 3 times with nitrogen, a hydrogen atmosphere was introduced and maintained by use of a balloon. After 24 h, the flask was again flushed several times with nitrogen, and the contents of the flask were filtered, rinsing with an additional 100 mL ethyl acetate. Rotary evaporation of the solvent afforded 0.156 g (quantitative) of the saturated benzylic ketone as a colorless, viscous oil (Rf 0.67, 2:1 hexane/ethyl acetate). $^1$H NMR (400 MHz, CDCl$_3$) δ 0.22 and 0.25 [2s, 2×3H, Si(CH$_3$)$_2$], 0.87 and 1.12 (2s, 2×3H, geminal-CH$_3$'s), 1.01 [s, 9H, SiC(CH$_3$)$_3$], 3.71 (s,3H, OCH$_3$), 6.79 (s, 1H, 6'-H), 6.91 ppm (s, 1H, 3'-H).

1-Methylidene-2-(2'-hydroxy-4'-bromo-5'-methoxy-phenyl)methyl-3,3-dimethylcyclohexane (racemic 1-desbromocyclocoymopol monomethyl ether) (13)

To a flame-dried 50 mL round-bottomed flask containing 2-[2'-(tert-butyl)dimethylsilyloxy-4'-bromo-5'-methoxyphenyl]methyl-3,3-dimethylcyclohexanone (12) (0.130 g, 0.28 mmol) in 5 mL anhydrous THF at −78° C. under nitrogen atmosphere was added (trimethyl)silymethyllithium (0.420 mL of a 1.0M solution in pentane, 0.42 mmol, 1.50 equiv). An immediate change from colorless to a yellow reaction solution was observed, and TLC analysis at that time indicated complete consumption of starting material, and the formation of a less polar product (Rf 0.79, 2:1 hexanes/ethyl acetate), and the reaction was subsequently quenched with 4 mL saturated aqueous NH$_4$Cl. Ethyl acetate (30 mL) extraction of the reaction mixture, drying over Na$_2$SO$_4$, and concentration under diminished pressure gave 0.152 g (quantitative) of a crude product, which appeared to be a single diastereomer of the ketone addition product by $^1$H NMR analysis. A portion of this crude intermediate (0.015 g, 0.028 mmol) was placed in a 10 mL nalgene vial containing 2 mL THF, 0.2 mL of a pre-made HF/pyridine complex was added, and the mixture was allowed to stir at room temperature for 32 h, at which time TLC analysis indicated complete consumption of starting material, and formation of a more polar product, having passed through a most polar intermediate (confirmed as the desilylated phenol by $^1$H NMR). The contents of the reaction vessel were transferred to a separatory funnel containing 20 mL ethyl acetate and 10 mL 1.0M NaHSO$_4$. The layers were separated, and the resultant organic phase was washed with 10 mL brine, dried over Na$_2$SO$_4$, and concentrated under diminished pressure. Purification by flash column chromatography (silica gel, hexane/ethyl acetate, gradient elution) afforded 8.7 mg (92%) of the phenolic olefin as a colorless oil. $^1$H NMR (400 MHz, CDCl$_3$) δ 0.97 and 1.00 (2s, 2×3H, geminal-CH$_3$'s), 2.65 and 2.80 (d of ABq, 2H, J$_{AB}$=14.1 Hz, J$_A$=10.9 Hz, J$_B$=3.5 Hz, benzylic-CH$_2$), 3.80 (s, 3H, OCH$_3$), 4.36 (d, 1H, J=1.0 Hz) and 4.64 (s, 1H) [methylidene-CH$_2$], 6.59 (s, 1H, 6'-H), 6.94 ppm (s, 1H, 3'-H); $^{13}$C NMR (100.61 MHz, CDCl$_3$) δ 23.5, 26.7, 28.1, 28.4, 32.4, 35.2, 36.1, 54.3, 57.0, 108.3, 110.3, 115.0, 120.1, 128.8, 148.0, 148.5, 150.0 ppm. [This compound is herein also referred to as Compound "C", or 120019]

EXAMPLE 8

1-Methylidene-2-(2'-acetoxy-4'-bromo-5'-methoxyphenyl)methyl-3,3-dimethylcyclohexane (racemic 1-desbromocyclocyamopol monomethyl ether, acetate) (84)

To a flame-dried 10 mL round-bottomed flask containing 1methylidene-2(2'-hydroxy-4'-bromo-5'-methoxyphenyl)methyl-3,3-dimethylcyclohexane (13) (4.4 mg, 0.013 mmol) in 1 mL of dry dichloromethane with 0.1 mL pyridine at room temperature was added 0.05 mL acetic anhydride and a catalytic amount of DMAP, and the mixture was allowed to stir 20 min. The reaction mixture was then quenched by the addition of pH 7 buffer (4 mL), and the resultant biphasic mixture was extracted with ethyl acetate (2×10 mL). The combined organic layers were dried over Na₂SO₄ and concentrated under diminished pressure. Purification by flash column chromatography (silica gel, hexanes/ethyl acetate, gradient elution) afforded 4.0 mg (88%) of the desired phenolic acetate as a white crystalline solid. ¹H NMR (400 MHz, CDCl₃) δ 0.96 and 0.97 (2s, 2×3H, geminal-CH₃'s), 2.05 (ddd, 1H, J=12.2, 8.5, 4.0 Hz, 3-H), 2.30 (s, 3H, acetate-CH₃), 2.50 and 2.73 (d of ABq, 2H, $J_{AB}$=13.9 Hz, $J_A$=11.5 Hz, $J_B$=3.4 Hz, benzylic-CH₂), 3.83 (s, 3H, OCH₃), 4.28 and 4.63 (2s, 2×1H, methylidene-CH₂) 6.58 (s, 1H, 6'-H), 7.18 ppm (s, 1H, 3'-H). [This compound is herein also referred to as Compound "A", or 120035]

EXAMPLE 9

1-Methylidene-2-(2'-hydroxy-4'-bromo-5'-methoxyphenyl) methyl-3,3-dimethylcyclo-pentane (96)

This compound was prepared from 4,4-dimethylcyclopent-2-en-1-one (94) and benzylic bromide (6) in 5 steps in the manner previously described for the synthesis of olefin (13), with the following procedural changes in the last two steps, from intermediate (95). To a flame-dried 25 mL round-bottomed flask containing a magnetic stir bar was added 340 mg (0.90 mmol) of cerium trichloride heptahydrate, and the flask was heated to 140° C. under vacuum for 2 h, after which time the solid was cooled to room temperature, and 3 mL of anhydrous THF was added. After stirring for 2 h at room temperature, the slurry was cooled to −78° C. and (trimethyl)silylmethyllithium (0.78 mL of a 1.0M solution in pentane, 0.78 mmol) was added. After 30 min, 2-[(2'-tert-butyl)dimethylsilyloxy-4'-bromo-5'-methoxyphenyl]methyl-3,3-dimethylcyclopentanone (95) (15.0 mg, 0.034 mmol) in 1 mL of anhydrous THF was added, and the mixture was allowed to stir at −78° C. for 4 h, before quenching with saturated aqueous NH₄Cl. The reaction mixture was extracted with ether, and the organic phase was dried over Na₂SO₄, and concentrated under diminished pressure. Purification by flash column chromatography (silica gel, hexanes/ethyl acetate 9:1) gave 15 mg (83%) of the tertiary alcohol intermediate as a colorless oil. Compound (96) was prepared from this alcohol intermediate (7.3 mg, 0.014 mmol) in the manner previously described for the preparation of olefin (13), affording 3.0 mg (66%) of the desired product as a colorless oil. ¹H NMR (400 MHz, CDCl₃) δ 0.92 and 0.96 (2s, 2×3H, geminal-CH₃'s), 1.53 (m, 2H, 4-H), 2.39 (m, 3H, 2-H and 5-H), 2.57 and 2.67 (d of ABq, 2H, benzylic-CH₂), 3.81 (s, 3H, OCH₃), 4.50 (s, 1H, OH), 4.66 and 4.84 (2s, 2×1H, methylidene-CH₂), 6.74 (s, 1H, 6'-H), 6.99 ppm (s, 1H, 3'-H). [This compound is herein also referred to as Compound "P", or 120192]

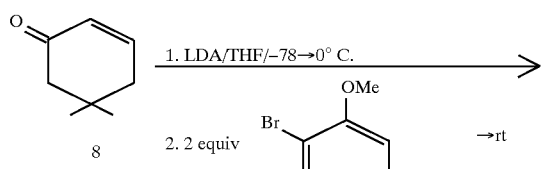

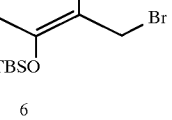

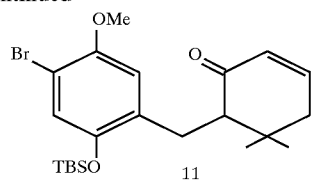

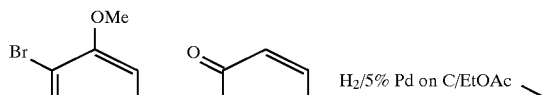

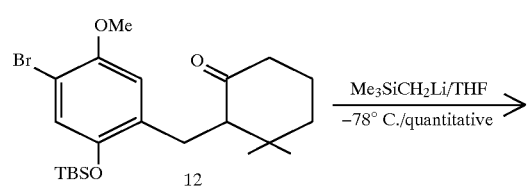

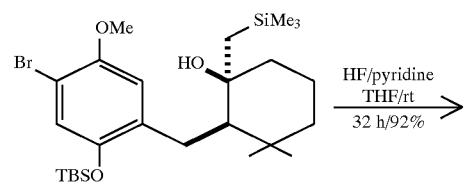

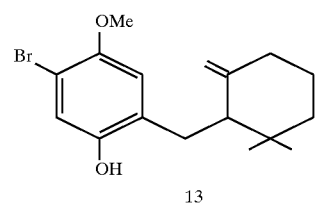

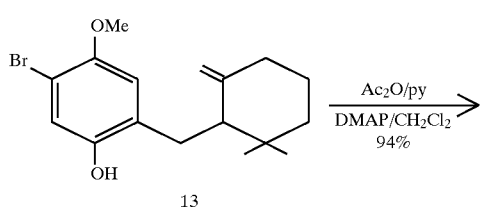

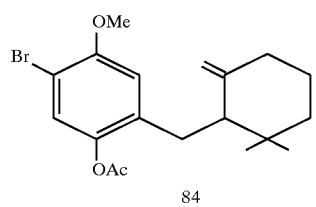

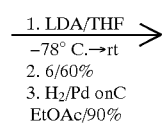

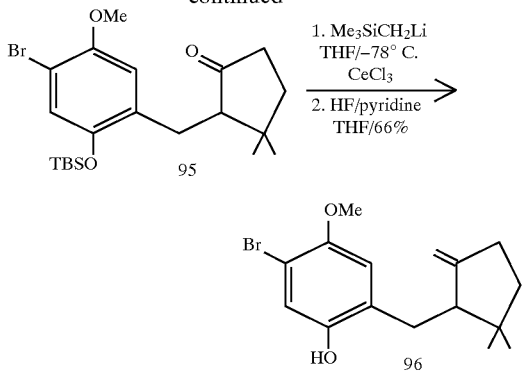

EXAMPLE 10

1-Methylidene-6-(2'-acetoxy-4'-bromo-5'-methoxyphenyl)methyl-5,5-dimethylcyclohex-2-ene (14)

This compound was prepared from 6-[2'-(tert-butyl)dimethylsilyloxy-4'-bromo-5'-methoxyphenyl]methyl-5,5-dimethylcyclohex-2-en-1-one (11) (0.075 g, 0.166 mmol) in the manner previously described for olefin (13), with the following procedural changes necessitated by the incompatibility of structural features particular to this substrate and the typical synthetic methodology. Upon formation of the initial (trimethyl)silylmethyllithium addition adduct to enone (11), the phenolic protecting group was exchanged prior to effecting elimination, using the following protocol adhered to for all cyclocymopol analogs possessing a 1,3-diene moiety as an extension of the methylidene olefin. The crude addition product (0.090 g, 0.166 mmol) was dissolved in 5 mL anhydrous THF containing 0.20 mL acetic anhydride (large excess), and cooled to 0° C. under nitrogen atmosphere. Tetra-n-butylammonium fluoride (0.20 mL of a 1.0M solution in THF, 0.20 mmol, 1.20 equiv) was added, and the mixture was allowed to warm to room temperature. The contents of the flask were then poured into a separatory funnel containing 30 mL ethyl acetate and 10 mL 1.0M $NaHSO_4$, the layers were separated, and the organic phase was washed with 10 mL brine, dried over $Na_2SO_4$, and concentrated under diminished pressure. The crude material thus obtained was immediately carried on to the next step by transferring to a 10 mL nalgene vial containing 2–3 mL THF, and 0.3 mL premade HF/pyridine complex was added. After stirring overnight at room temperature, the reaction mixture was worked up in the usual manner, and purification by flash column chromatography (silica gel, hexane/ethyl acetate, gradient elution) afforded 38.3 mg (64%) of the desired acetoxy-diene as a colorless, oily solid. $^1H$ NMR (400 MHz, $CDCl_3$) δ 0.73 and 1.11 (2s, 2×3H, geminal-$CH_3$'s), 2.27 (s, 3H, acetate-$CH_3$), 3.83 (s, 3H, $OCH_3$), 4.13 and 4.68 (2s, 2×1H, C=$CH_2$), 5.70 and 6.04 (2dd, 2×1H, 2-H, 3-H), 6.52 and 7.19 ppm (2s, 2×1H, Ar—H). [This compound is also referred to as Compound "L" or 120032]

EXAMPLE 11

1-Methylidene-6-(2'-hydroxy-4'-bromo-5'-methoxyphenyl)methyl-5,5-dimethylcyclohex-2-ene (15)

In a 10 mL test tube was combined 1-methylidene-6-(2'-acetoxy-4'-bromo-5'-methoxyphenyl)methyl-5,5-dimethylcyclohex-2-ene (14) (10.0 mg, 0.026 mmol) and 2.0 mL of 5% methanolic $K_2CO_3$. After 10 min at room temperature, the methanol was removed by rotary evaporation, and the resultant residue was dissolved in 20 mL ethyl acetate. The organic solution was then washed with saturated aqueous $NH_4Cl$, dried over $Na_2SO_4$, and concentrated under diminished pressure. Purification by flash column chromatography (silica gel deactivated with triethylamine, hexane/ethyl acetate, gradient elution) afforded 7.1 mg (81%) of the phenolic diene as a colorless, oily solid. $^1H$ NMR (400 MHz, $CDCl_3$) δ 0.73 and 1.16 (2s, 2×3H, geminal-$CH_3$'s), 3.82 (s, 3H, $OCH_3$), 4.23 and 4.72 (2s, 2×1H, C=$CH_2$), 5.78 and 6.08 (2dd, 2×1H,2-H, 3-H), 6.51 and 6.99 ppm (2s, 2×1H, Ar—H). [This compound is also referred to as Compound "K" or 120033]

EXAMPLE 12

6-[2'-(tert-Butyl)dimethylsilyloxy-4'-bromo-5'-methoxyphenyl]methyl-3,5,5-trimethyl-cyclohex-2-en-1-one (16)

This compound was prepared from isophorone (0.168 g, 1.22 mmol) in the manner previously described for enone (11), affording 0.342 g (60%) of the alkylation product (Rf 0.40, 2:1 hexane/ethyl acetate) as a colorless, oily solid. $^1H$ NMR (400 MHz, $CDCl_3$) δ 0.20 and 0.22 [2s, 2×3H, Si($CH_3$)$_2$], 0.99 [s, 9H, SiC($CH_3$)$_3$], 1.00 and 1.02 (2s, 2×3H, geminal-$CH_3$'s), 1.91 (s,3H, olefinic-$CH_3$), 2.18 (ABq, 2H), 2.42 (dd, 1H), 2.82 (dd, 2H), 3.70 (s, 3H, $OCH_3$), 5.82 (sl d, 1H, 2-H), 6.71 and 6.92 ppm (2s, 2×1H, Ar—H).

1-Methylidene-6-(2'-acetoxy-4'-bromo-5'-methoxyphenyl)methyl-3,5,5-trimethylcyclohex-2-ene (17)

This compound was prepared from 6-[2'-(tert-butyl)dimethylsilyloxy-4'-bromo-5'-methoxyphenyl]methyl-3,5,5-trimethylcyclohex-2-en-1one (16) (42.0 mg, 0.090 mmol) in the manner previously described for acetoxy diene 14, affording 18.4 mg (52%) of the acetoxy-diene as a colorless oil. $^1H$ NMR (400 MHz, $CDCl_3$) δ 0.87 and 1.11 (2s, 2×3H, geminal-$CH_3$,S), 1.78 (s, 3H, olefinic-$CH_3$), 2.26 (s, 3H, acetate-$CH_3$), 3.83 (s, 3H, $OCH_3$), 4.03 and 4.58 (2s, 2×1H, C=$CH_2$), 5.82 (s, 1H, 2-H), 6.52 and 7.19 ppm (2s, 2×1H, Ar—H). [This compound is also referred to as Compound "H" or 120028]

EXAMPLE 13

1-Methylidene-6-(2'-hydroxy-4'-bromo-5'-methoxyphenyl)methyl-3,5,5-trimethylcyclohex-2-ene (18)

This compound was prepared from 1-methylidene-6-(2'-acetoxy-4'-bromo-5'-methoxyphenyl)methyl-3,5,5-trimethylcyclohex-2-ene (17) (6.8 mg, 0.017 mmol) in the manner previously described for phenolic diene 15, affording 5.8 mg (96%) of the phenolic diene as a colorless, oily solid. $^1H$ NMR (400 MHz, $CDCl_3$) δ 0.74 and 1.15 (2s, 2×3H, geminal-$CH_3$'s), 1.79 (s, 3H, olefinic-$CH_3$), 2.26 (s, 3H, acetate-$CH_3$), 3.81 (s, 3H, $OCH_3$), 4.16 and 4.62 (2s, 2×1H, C=$CH_2$), 5.87 (s, 1H, 2-H), 6.52 and 6.99 ppm (2s, 2×1H, Ar—H). [This compound is also referred to as Compound "II" or 120048]

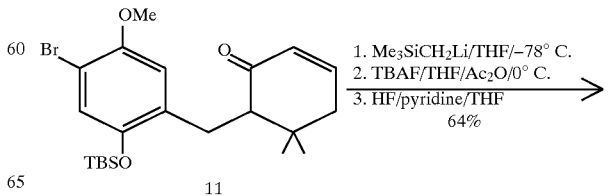

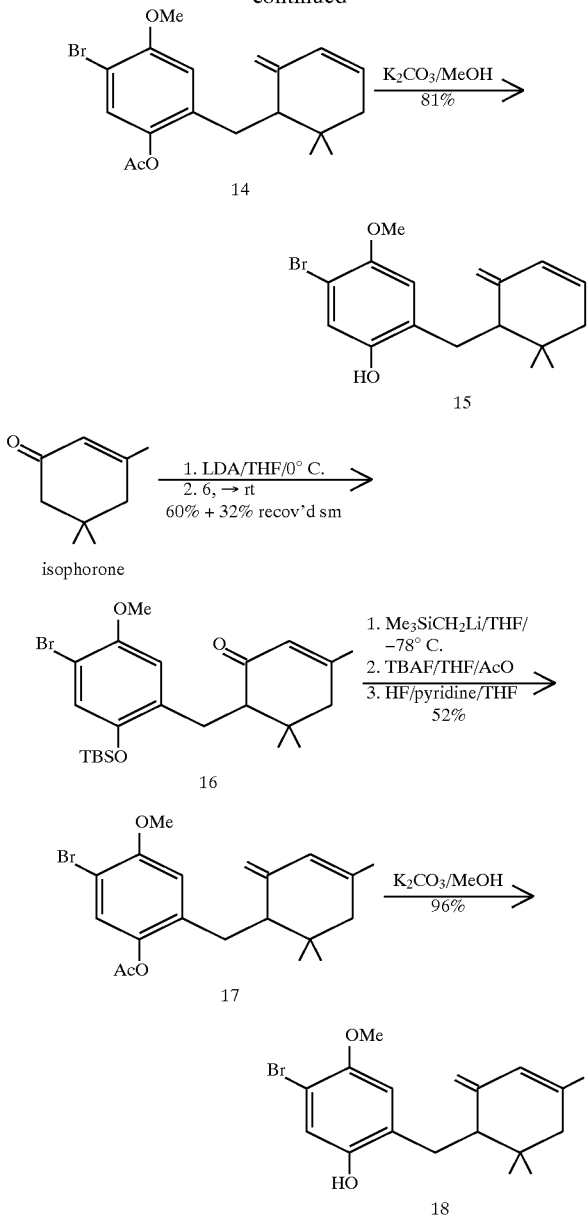

EXAMPLE 14
trans-6-[2'-(tert-Butyl)dimethylsilyloxy-4'-bromo-5'-methoxyphenyl]methyl-4,5,5-trimethylcyclohex-2-en-1-one (19)

This compound was prepared from 4,5,5-trimethylcyclohex-2-en-1-one (10) (169 mg, 1.22 mmol) in the manner previously described for benzylated enone 11, affording 0.337 g (59%) of the less polar trans diastereomer as a colorless, oily solid, along with 22 mg (4%) of the more polar cis diastereomer as a colorless, oily solid, separable by flash column chromatography. The relative stereochemistry of each respective diastereomer was confirmed by nOe NMR experiments. $^1$H NMR (400 MHz, CDCl$_3$) δ 0.21 and 0.23 [2s, 2×3H, Si(CH$_3$)$_2$], 0.98 [s, 9H, SiC(CH$_3$)$_3$], 0.90 and 1.10 (2s, 2×3H, geminal-CH$_3$'s), 1.11 (d, 3H, CHCH$_3$), 2.45 (dd, 1H), 2.53 (ddd, 1H), 2.72 and 2.97 (d of ABq, 2H, benzylic-H's), 3.81 (s, 3H, OCH$_3$), 5.87 (dd, 1H, 2-H), 6.55 (dd, 1H, 3-H), 6.64 (s, 1H, Ar—H), 6.93 ppm (s, 1H, Ar—H).

trans-2-[2'-(tert-Butyl)dimethylsilyloxy-4'-bromo-5'-methoxyphenyl]methyl-3,3,4-trimethylcyclohexanone (20)

This compound was prepared from trans-6-[2'-(tert-butyl)dimethylsilyloxy-4'-bromo-5'-methoxyphenyl]methyl-4,5,5-trimethylcyclohex-2-en-1-one (19) (150 mg, 0.321 mmol) in the manner previously described for benzylated ketone 12, affording 0.149 g (99%) of the trans ketone as a colorless, oily solid. $^1$H NMR (400 MHz, CDCl$_3$) δ 0.22 and 0.23 [2s, 2×3H, Si(CH$_3$)$_2$], 0.92 and 0.99 (2s, 2×3H, geminal-CH$_3$'s), 1.00 [s, 9H, SiC(CH$_3$)$_3$], 1.01 (d, 3H, CHCH$_3$), 2.77 and 2.95 (d of ABq, 2H, benzylic-H's), 3.82 (s, 3H, OCH$_3$), 6.73 (s, 1H, Ar—H), 6.92 ppm (s, 1H, Ar—H).

trans-1-Methylidene-6-(2'-acetoxy-4'-bromo-5'-methoxyphenyl)methyl-4,5,5-trimethylcyclohex-2-ene (21)

This compound was prepared from trans-6-[2'-(tert-butyl)dimethylsilyloxy-4'-bromo-5'-methoxyphenyl]methyl-4,5,5-trimethylcyclohex-2-en-1-one (19) (70.0 mg, 0.15 mmol) in the manner previously described for acetoxy-diene 14, affording 46.8 mg (79%) of the acetoxy-diene as a colorless oil. $^1$H NMR (400 MHz, CDCl$_3$) δ 0.76 and 1.14 (2s, 2×3H, geminal-CH$_3$'s), 1.00 (d, 3H, CHCH$_3$), 2.30 (s, 3H, acetate-CH$_3$), 3.85 (s, 3H, OCH$_3$), 4.12 and 4.67 (2s, 2×1H, C=CH$_2$), 5.46 (d, 1H, 2-H), 6.01 (dd, 1H, 3-H), 6.53 and 7.21 ppm (2s, 2>1H, Ar—H). [This compound is also referred to as Compound "N" or 120049]

EXAMPLE 15
trans-1-Methylidene-6-(2'-hydroxy-4'-bromo-5'-methoxyphenyl)methyl-4,5,5-trimethylcyclohex-2-ene (22)

This compound was prepared from trans-1-methylidene-6-(2'-acetoxy-4'-bromo-5'-methoxyphenyl)methyl-4,5,5-trimethylcyclohex-2-ene (21) (5.5 mg, 0.014 mmol) in the manner previously described for phenolic diene 15, affording 4.1 mg (84%) of the phenolic diene as a colorless, oily solid. $^1$H NMR (400 MHz, CDCl$_3$) δ 0.74 and 1.18 (2s, 2×3H, geminal-CH$_3$'s), 1.00 (d, 3H, CHCH$_3$), 3.80 (s, 3H, OCH$_3$), 4.22 and 4.70 (2s, 2×1H, C=CH2), 5.52 (d, 1H, 2-H), 6.04 (dd, 1H, 3-H), 6.50 and 6.99 ppm (2s, 2×1H, Ar—H). [This compound is also referred to as Compound "KK" or 120050]

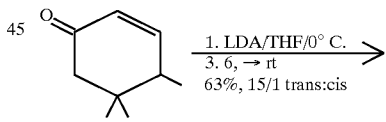

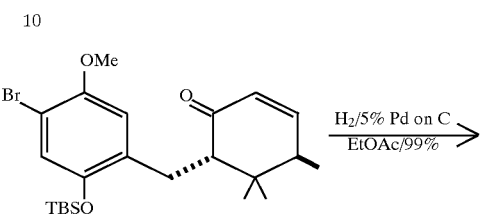

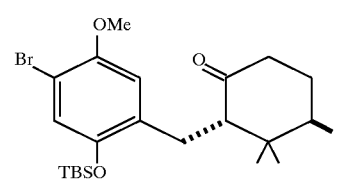

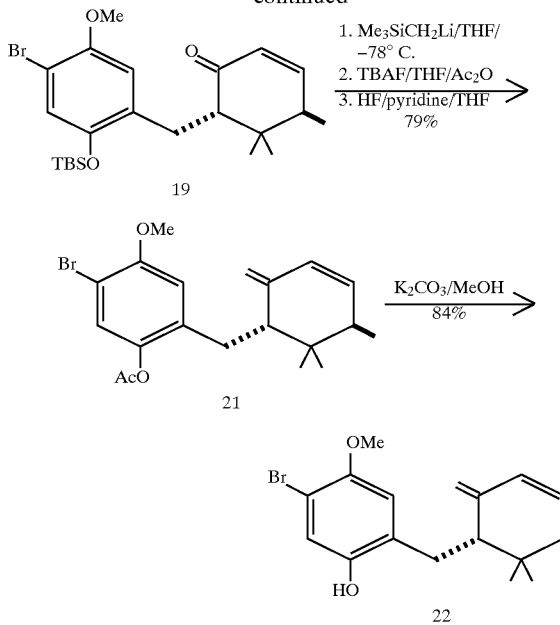

EXAMPLE 16
trans-1-Methylidene-2-(2'-hydroxy-4'-bromo-5'-methoxyphenyl)methyl-3,3,4-trimethylcyclohexane (23)

This compound was prepared from trans-2-[2'-(tert-butyl)dimethylsilyloxy-4'-bromo-5'-methoxyphenyl]methyl-3,3,4-trimethylcyclohexanone (20) (47.0 mg, 0.089 mmol) in the manner previously described for phenolic olefin 13 to afford 22.6 mg (72%) of the trans phenolic olefin as a colorless, oily solid. $^1$H NMR (400 MHz, CDCl$_3$) δ 0.79 and 1.08 (2s, 2×3H, geminal-CH$_3$'s), 0.85 (d, 3H, CHCH$_3$), 3.80 (s, 3H, OCH$_3$), 4.36 and 4.58 (2s, 2×1H, C=CH$_2$), 6.50 and 6.99 ppm (2s, 2×1H, Ar—H). [This compound is also referred to as Compound "LL" or 120034]

EXAMPLE 17
1-Methylidene-2-(4'-bromophenyl)methyl-3,3-dimethylcyclohexane (88)

This compound was prepared from 5,5-dimethylcyclohex-2-en-1-one (8) and p-bromobenzyl bromide in three steps in the manner described for the synthesis of olefin (13). $^1$H NMR (400 MHz, CDCl$_3$) δ 0.94 and 0.97 (2s, 2×3H, geminal-CH$_3$'s), 2.62 and 2.82 (d of ABq, 2H, benzylic-CH$_2$), 4.25 and 4.61 (2s, 2×1H, methylidene-CH$_2$), 6.98 (d, 2H, Ar—H), 7.34 ppm (d, 2H, Ar—H). [This compound is also referred to as Compound "O" or 120130]

EXAMPLE 18
2-(4'-Nitrophenyl)methylcyclohexan-1-one (85)

To a solution of diisopropylamine (342 mL, 2.45 mmol, 1.2 equiv) in 5 mL of anhydrous THF at 0° C. was added n-butyllithium (1.63 mL of a 1.6M solution in hexane), and the mixture was stirred at this temperature for 15 minutes before cooling to −78° C. Cyclohexanone (221 mL, 2.04 mmol, 1.0 equiv) in 2 mL of anhydrous THF was then added dropwise, stirred at −78° C. for 1 h followed by p-nitrobenzyl bromide (880 mg, 4.08 mmol, 2.00 equiv) in 2 mL of THF, added dropwise to the resulting enolate. The reaction mixture was stirred at room temperature for 17 h, and then quenched with aqueous saturated NH$_4$Cl, and extracted with ether. The organic phase was dried over Na$_2$SO$_4$ and concentrated under diminished pressure to a solid residue that was purified by flash chromatography (silica gel, hexanes/ethyl acetate, 85:15), which afforded 300 mg (64%) of the desired ketone as a yellow solid. $^1$H NMR (400 MHz, CDCl$_3$) δ 1.41 (m, 1H), 1.66 (m, 2H), 1.88 (m, 1H), 2.08 (m, 2H), 2.33 (m, 1H), 2.45 (m, 1H), 2.57 (m, 1H, 2-H), 2.59 and 3.29 (d of ABq, 2H, benzylic-CH$_2$), 7.34 (d, 2H, Ar—H), 8.12 ppm (d, 2H, Ar—H). [This compound is also referred to as Compound "F" or 120138]

EXAMPLE 19
1-Methylidene-2-(4'-nitrophenyl)methylcyclohexane (86)

This compound was prepared from cyclohexanone and p-nitrobenzyl bromide in two steps in the manner described for the synthesis of olefin (49). 1H NMR (400 MHz, CDCl$_3$) δ 2.09 (ddd, 1H, 6-H), 2.36 (m, 2H, 2,6-H), 2.67 and 3.06 (d of ABq, 2H, benzylic-CH$_2$), 4.55 and 4.70 (2s, 2×1H, methylidene-CH$_2$), 7.31 (d, 2H, 2',6'-H), 8.14 ppm (d, 2H, 3',5'-H). [This compound is also referred to as Compound "Q" or 120194]

EXAMPLE 20
6-(4'-Nitrophenyl)methyl-5,5-dimethylcyclohex-2-en-1-one (24)

This compound was prepared from 5,5-dimethylcyclohex-2-en-1-one (8) (0.600 g, 4.83 mmol) and p-nitrobenzyl bromide (1.581 g, 7.32 mmol) in the manner described for the synthesis of enone 11, affording 627 mg (50%) of the nitro-enone as a pale yellow oil. $^1$H NMR (400 MHz, CDCl$_3$) δ 1.02 and 1.18 (2s, 2×3H, geminal-CH$_3$'s), 2.83 and 3.10 (d of ABq, 2H, benzylic-H's), 6.00 (ddd, 1H, 2-H), 6.81 (ddd, 1H, 3-H), 7.38 and 8.10 ppm (2d, 2×2H, Ar—H). [This compound is also referred to as Compound "MM" or 120025]

EXAMPLE 21
1-Methylidene-6-(3'-methyl-4'-nitrophenyl)methyl-5,5-dimethylcyclohex-2-ene (25)

This compound was prepared from 6-(4'-nitrophenyl)methyl-5,5-dimethylcyclohex-2-en-1-one (24) (133 mg, 0.514 mmol) in the manner previously described for the synthesis of olefin 13, with the following procedural changes. Three equivalents of (trimethyl)silylmethyllithium were used, and the subsequent elimination step required 48 h to go to completion, affording 120 mg (86%) of the nitro-diene as a colorless oil. $^1$H NMR (400 MHz, CDCl$_3$) δ 0.92 and 1.12 (2s, 2×3H, geminal-CH$_3$'s), 2.58 (s, 3H, Ar—CH$_3$), 4.05 and 4.64 (2s, 2×1H, methylidene-CH$_2$), 5.70 (ddd, 1H, 3-H), 6.03 (dd, 1H, 2-H), 6.98 (s, 1H, Ar—H), 6.99 and 7.88 ppm (2d, 2×1H, Ar—H). [This compound is also referred to as Compound "M" or 120120]

EXAMPLE 22
1-Methylidene-2-(2'-hydroxy-4'-bromo-5'-methoxyphenyl)methylcyclohexane (26)

This compound was prepared in three steps from cyclohexanone and 2-(tert-butyl)dimethylsilyloxy-4-bromo-5-methoxybenzyl bromide (6) as previously described for the synthesis of olefin 13, to give the desired olefin in three steps in 13.5% overall yield as a colorless oil. $^1$H NMR (400 MHz, CDCl$_3$) δ 2.54 and 2.92 (d of ABq, 2H, benzylic-H's), 3.84 (s, 3H, OCH$_3$), 4.46 (s, 1H, OH), 4.62 and 4.71 (2s, 2×1H, methylidene-CH$_2$), 6.65 and 6.98 ppm (2s, 2×1H, Ar—H). [This compound is also referred to as Compound "S" or 120089]

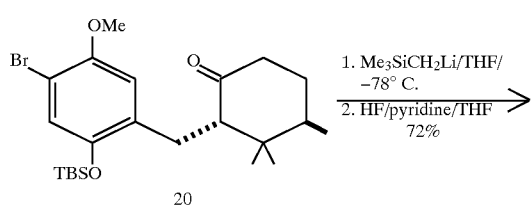
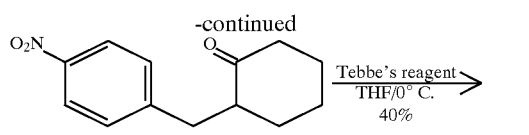
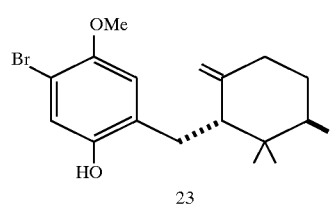
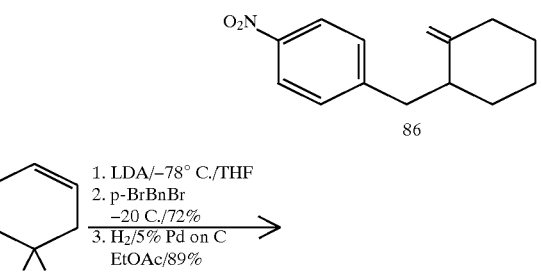
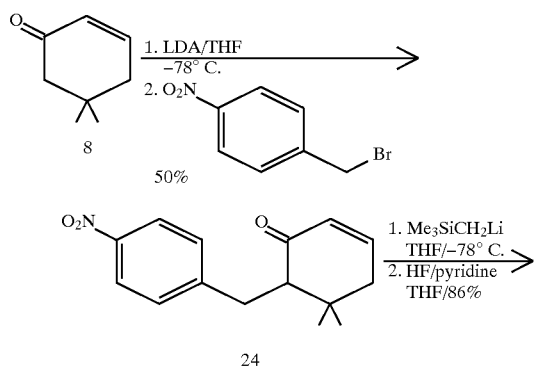
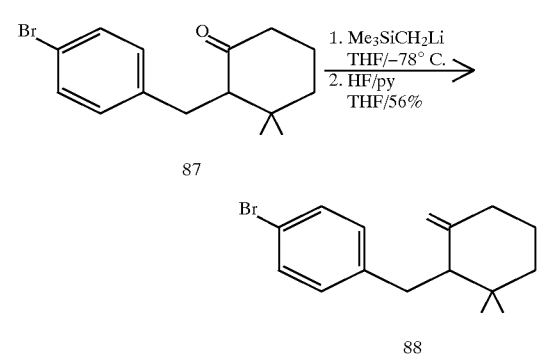
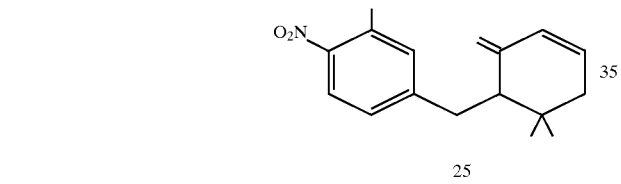
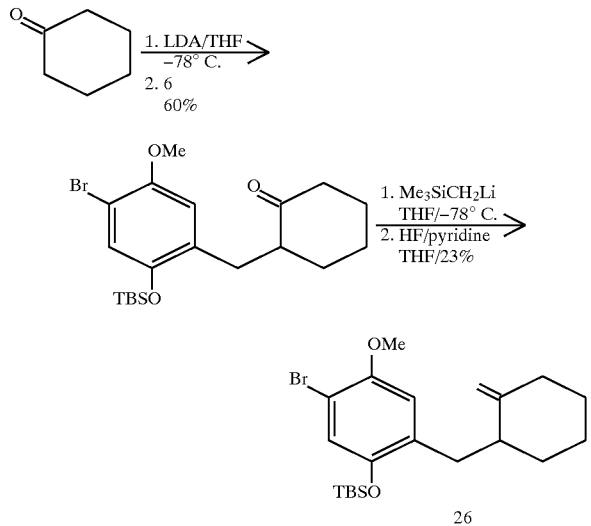
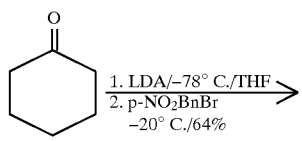

Semisynthetic Derivatives of Natural Cyclocymopols

EXAMPLE 23

(3R)-Cyclocymopol monomethyl ether, methyl carbonate (89)

To a flame-dried 10 mL round-bottomed flask containing (3R)-Cyclocymopol monomethyl ether (7.0 mg, 0.017 mmol) in 1 mL dry dichloromethane at room temperature was added DMAP (30.5 mg, 0.25 mmol, 15 equiv), followed by methyl chloroformate (15.0 mL, 0.20 mmol, 12 equiv).

After 2 h at room temperature, 2 mL of water and 10 mL of hexanes were added, and the mixture was washed with 1.0M NaHSO$_4$ and pH 7 phosphate buffer (6 mL of 1:1). The organic layer was dried over Na$_2$SO$_4$ and concentrated under diminished pressure, affording 7.0 mg (95%) of the desired phenolic carbonate as a colorless crystalline film. $^1$H NMR (400 MHz, CDCl$_3$) δ 1.08 and 1.18 (2s, 2×3H, geminal-CH$_3$'s), 3.80 (s, 3H, Ar—OCH$_3$), 3.91 (s, 3H, C=OOCH$_3$), 4.29 and 4.59 (2s, 2×1H, methylidene-CH$_2$), 4.44 (dd, 1H, 1-H), 6.69 (s, 1H, 6'-H), 729 ppm (s, 1H, 3'-H). [This compound is also referred to as Compound "T" or 120011]

EXAMPLE 24

(3R)-1-Debromocyclocymopol monomethyl ether (27)

To a flame-dried 10 mL round-bottomed flask containing (3R)-2'-(tert-butyl)dimethylsilyloxycyclocymopol monomethyl ether (19.5 mg, 0.036 mmol) in 1 mL anhydrous benzene with 1–2 mg AIBN at room temperature was added n-Bu$_3$SnH (39 μL, 0.144 mmol, 4.0 equiv). After 90 min, TLC analysis indicated virtually complete consumption of starting material, and formation of a slightly less polar product. Carbon tetrachloride (200 μL) was added, and after 1 h at room temperature followed by 1.5 h at 0° C., 2 mL THF and 200 μL 1.0M tetrabutylammonium fluoride solution in THF were added. After 10 min at 0° C., pH 7 buffer was added, and the reaction mixture was extracted with hexane. The resultant organic solution was dried over $Na_2SO_4$, and concentrated under diminished pressure. Purification by flash column chromatography (silica gel, 10% ethyl acetate in hexane) afforded 7.5 mg (61%) of the debromophenol as a colorless oil. The 400 MHz $^1$H NMR spectrum and TLC elution properties of this compound were identical to those reported for the racemic analog 13. [This compound is also referred to as Compound "J" or 120037]

EXAMPLE 25

(3R)-1-Debromocyclocymopol monomethyl ether, benzoate (90)

To a flame-dried 10 mL round-bottomed flask containing (3R)-1-debromocyclocymopol monomethyl ether (3.5 mg, 0.010 mmol) in 1 mL of dry dichloromethane with 0.1 mL pyridine at room temperature was added 0.05 mL benzoyl chloride and a catalytic amount of DMAP, and the mixture was allowed to stir 20 min. The reaction mixture was then quenched by the addition of pH 7 buffer (5 mL), and the resultant biphasic mixture was extracted with ethyl acetate (2×10 mL). The combined organic layers were dried over $Na_2SO_4$ and concentrated under diminished pressure. Purification by flash column chromatography (silica gel, hexaneslethyl acetate, gradient elution) afforded 3.0 mg (60%) of the desired benzoate ester as a colorless oil (Rf 0.47, 2:1 hexanes/ethyl acetate). $^1$H NMR (400 MHz, CDCl$_3$) δ 0.98 and 0.99 (2s, 2×3H, geminal-CH$_3$'s), 2.09 (ddd, 1H, J=12.2, 8.5, 4.0 Hz, 3-H), 2.60 and 2.78 (d of ABq, 2H, $J_{AB}$=13.9 Hz, $J_A$=11.5 Hz, $J_B$=3.4 Hz, benzylic-CH$_2$), 3.82 (s, 3H, OCH$_3$), 4.29 and 4.62 (2s, 2×1H, methylidene-CH$_2$) 6.65 (s, 1H, 6'-H), 7.28 (s, 1H, 3'-H), 7.51 (m, 3H, Ar—H), 8.10 ppm (d, 2H, J=8.0 Hz, Ar—H). [This compound is also referred to as Compound "U" or 120198]

EXAMPLE 26

(3R)-1-Debromocyclocymopol monomethyl ether, methyl carbonate (91)

This compound was prepared from (3R)-1-debromocyclocymopol monomethyl ether (27) in the manner previously described for the synthesis of carbonate 89. The TLC elution properties and $^1$H NMR spectral data for this compound are identical to those reported for compound (93). [This compound is also referred to as Compound "R" or 120057]

EXAMPLE 27

(3S)-1-Debromocyclocymopol monomethyl ether (28)

This compound was prepared from (3S)-2'-(tert-butyl) dimethylsilyloxycyclocymopol monomethyl ether (25.0 mg, 0.047 mmol) in the manner described for the synthesis of the cyclocymopol derivative 27, affording 5.5 mg (35%) of the debromophenol as a colorless oil, along with the remainder of the mass balance as deprotected starting material. The 400 MHz $^1$H NMR spectrum and TLC elution properties of this compound were identical to those reported for the racemic analog 13. [This compound is also referred to as Compound "G" or 120058]

EXAMPLES 28–29

(3S)-1-Debromocyclocymopol monomethyl ether, acetate (92)

This compound was prepared from (3S)-1-debromocyclocymopol monomethyl ether (28) in the manner previously described for the synthesis of acetate (84). The TLC elution properties and $^1$H NMR spectral data for this compound are identical to those reported for the racemic analog (84). [This compound is also referred to as Compound "B" or 120093]

(3S)-1-Debromocyclocymopol monomethyl ether, methyl carbonate (93)

This compound was prepared from (3S)-1-debromocyclocymopol monomethyl ether (28) in the manner previously described for the synthesis of carbonate (89). $^1$H NMR (400 MHz, CDCl$_3$) δ 0.96 and 0.97 (2s, 2×3H, geminal-CH$_3$'s), 2.05 (ddd, 1H, J=12.1, 8.5, 4.0 Hz, 3-H), 2.56 and 2.78 (d of ABq, 2H, $J_{AB}$=13.9 Hz, $J_A$=11.5 Hz, JB =3.4 Hz, benzylic-CH$_2$), 3.83 (s, 3H, OCH$_3$), 4.27 and 4.62 (2s, 2×1H, methylidene-CH$_2$) 6.62 (s, 1H, 6'-H), 7.28 ppm (s, 1H, 3'-H). [This compound is also referred to as Compound "D" or 120094]

EXAMPLE 30

(3R)-4'-Formylcyclocymopol monomethyl ether (29)

To a flame-dried 10 mL round-bottomed flask containing (3R)-2'-tert-butyl)dimethylsilyloxycyclocymopol monomethyl ether (53.4 mg, 0.10 mmol) in 2 mL anhydrous THF at −78° C. was added n-butyllithium (70 μL of a 2.15M solution in hexane, 0.15 mmol, 1.50 equiv) all in one portion. After 10 min at −78° C., N-methyl-N-(2-pyridyl) formamide (28.5 mg, 25 μL, 0.21 mmol, 2.1 equiv) was added as a solution in 1 mL THF, and the reaction mixture was allowed to stir for 30 min before quenching with 1 mL 1:4 acetic acid/methanol.

The reaction mixture was then partitioned between hexane and 1.0M NaHSO$_4$, washed with pH 7 buffer, and the resultant organic phase was dried over $Na_2SO_4$ and concentrated under diminished pressure. Purification by radial chromatography (silica gel, 1 mm chromatotron plate, 10–15% ethyl acetate in hexane) gave 28.1 mg (58%) of the protected phenolic aldehyde as a white solid.

A portion of this silylated phenol (3.5 mg) was deprotected using 25 μL of 1.0M tetrabutylammonium fluoride in 1 mL THF at 0° C. The reaction was quenched with pH 7 buffer, and partitioned between hexanes and water. The resultant organic phase was dried over $Na_2SO_4$ and concentrated under diminished pressure. Purification by radial chromatography (silica gel, 1 mm chromatotron plate, 15% ethyl acetate in hexanes) gave 2.1 mg (79%) of the desired aldehyde as a white solid. $^1$H NMR (400 MHz, CDCl$_3$) δ 1.10 and 1.26 (2s, 2×3H, geminal-CH$_3$'s), 2.70 and 3.01 (d of ABq, 2H, benzylic-H's), 3.84 (s, 3H, OCH$_3$), 4.39 and 4.62 (2s, 2×1 H, methylidene-CH$_2$), 4.44 (dd, 1H, BrCH), 6.60 and 7.27 (2s, 2×1H, Ar—H), 10.33 ppm (s, 1H, CHO). [This compound is also referred to as Compound "NN" or 120063]

EXAMPLE 31

(3R)-4'-Iodocyclocymopol monomethyl ether (30)

This compound was prepared from (3R)-2'-(tert-butyl) dimethylsilyloxycyclocymopol monomethyl ether (15.2 mg, 0.029 mmol) and iodine (300 μL of a 0.25M solution in benzene, 0.075 mmol, 2.6 equiv) in the manner previously described for cyclocymopol derivative 29, affording 9.2 mg (70%) of the iodocyclocymopol derivative as a colorless oily solid. $^1$H NMR (400 MHz, CDCl$_3$) δ 1.08 and 1.22 (2s, 2×3H, geminal-CH$_3$'s), 2.52 and 2.91 (d of ABq, 2H, benzylic-H's), 3.78 (s, 3H, OCH$_3$), 4.30 and 4.62 (2s, 2×1H, methylidene-CH$_2$), 4.42 (dd, 1H, ICH), 4.49 (s, 1H, OH), 6.45 and 7.10 ppm (2s, 2×1H, Ar—H). [This compound is also referred to as Compound "V" or 120111]

EXAMPLE 32
(3R,5R)-5-Hydroxycyclocymopol monomethyl ether (31)

To a flame-dried 25 mL round-bottomed flask containing (3R)-2'-(tert-butyl)dimethylsilyloxycyclocymopol monomethyl ether (13.8 mg, 0.026 mmol) in 3.5 mL anhydrous dichloromethane at room temperature was added selenium dioxide (1.5 mg, 0.013 mmol, 0.50 equiv) and anhydrous t-butyl hydroperoxide (17.3 µL of a 3.0M solution in 2,2,4-trimethylpentane, 0.052 mmol, 2.00 equiv), and the mixture was allowed to stir at room temperature for 40 h, at which time the solvent was removed by rotary evaporation. Purification by flash column chromatography (silica gel, hexanes/ethyl acetate, gradient elution) afforded 13 mg of material which was dissolved in 1 mL THF, cooled to 0° C., and treated with tetrabutylammonium fluoride (0.03 mL of a 1.0M solution in THF, 0.030 mmol, 1.15 equiv). After 10 min, the reaction was quenched by the addition of pH 7 buffer (5 mL), and extracted with hexanes (2×25 mL). The combined organic extracts were dried over $Na_2SO_4$, and concentrated under diminished pressure. Purification by flash column chromatography (silica gel, hexanes/ethyl acetate, gradient elution) afforded 8.8 mg (78%) of the hydroxycyclocymopol as a white sold. $^1$H NMR (400 MHz, $CDCl_3$) δ 1.04 and 1.23 (2s, 2×3H, geminal-$CH_3$'s), 3.83 (s, 3H, $OCH_3$), 4.42 (dd, 1H, CHBr), 4.43 and 4.96 (2s, 2×2H, methylidene-$CH_2$), 4.73 (dd, 1H, CHOH), 6.54 and 7.00 ppm (2s, 2×1H, Ar—H). [This compound is also referred to as Compound "E" or 120195]

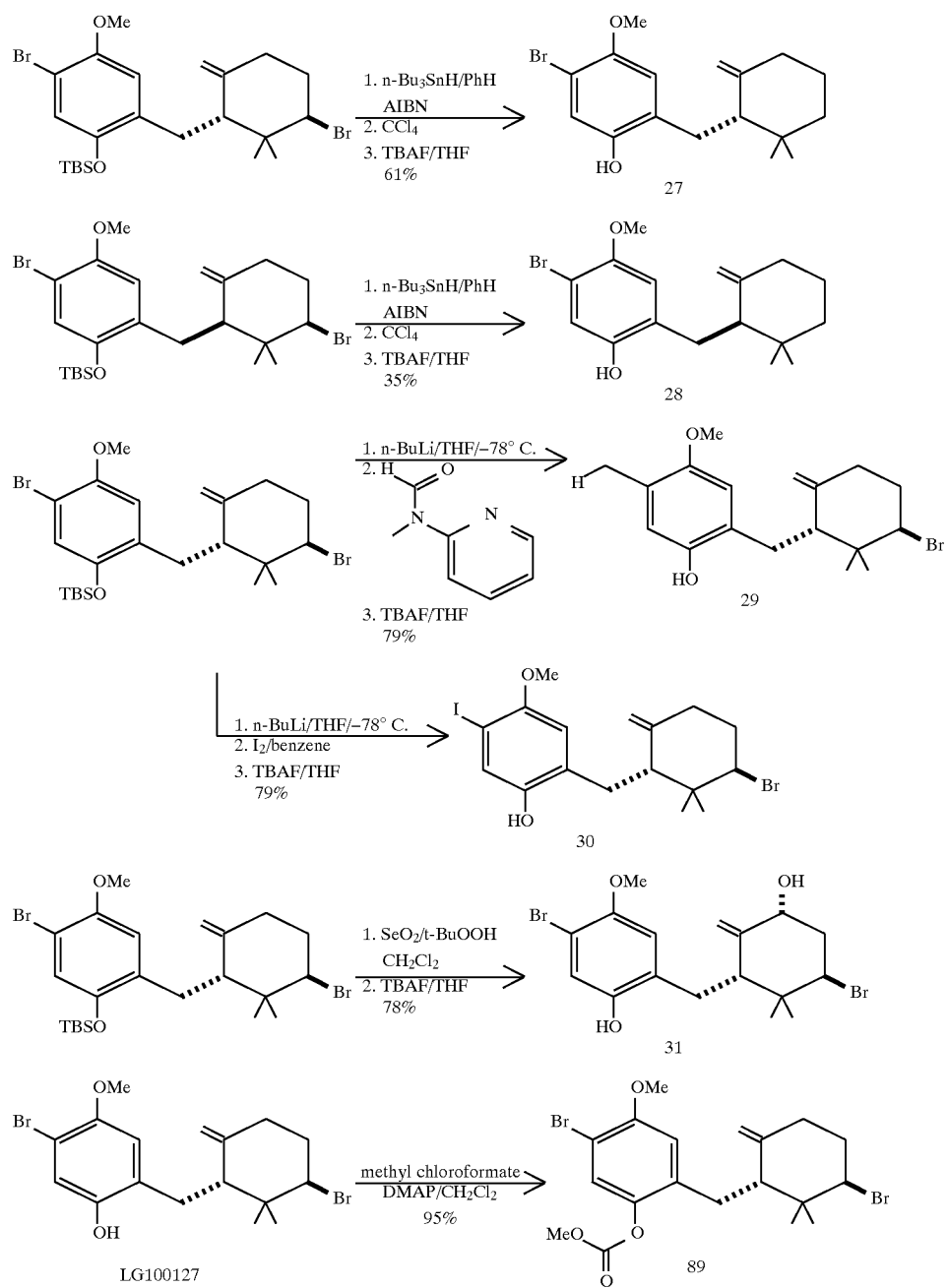

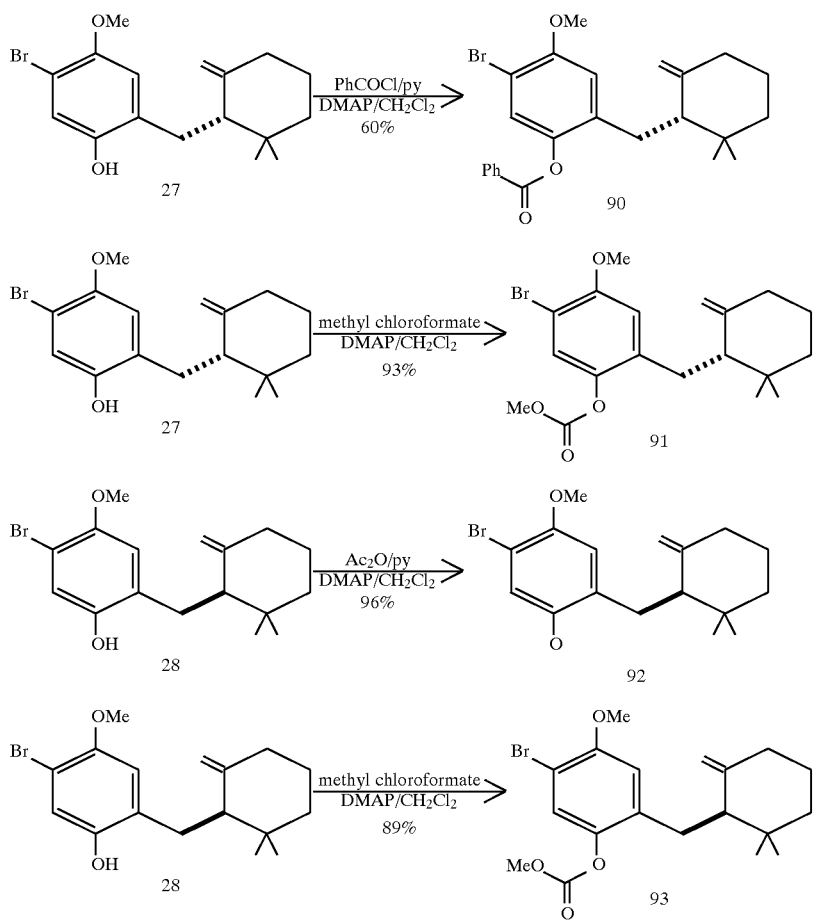

EXAMPLE 33

Synthesis of Second Aromatic Subunit trans-Methyl-2-(tert-butyl)dimethylsilyloxy-4-bromo-5-methoxycinnamate (41)

To a flame-dried 25 mL 3-necked round-bottomed flask equipped with a reflux condenser and an addition funnel at room temperature under nitrogen atmosphere was added sodium hydride (0.232 g of a 60% dispersion in mineral oil, 5.80 mmol, 1.00 equiv). Anhydrous benzene (2 mL) was added, and then trimethylphosphonoacetate (1.056 g, 5.80 mmol, 1.00 equiv) was added dropwise through the addition funnel over a period of 45 min as a solution in 1 mL benzene. The reaction mixture was vigorously stirred for an additional 90 min at room temperature before 2-(tert-butyl)dimethylsilyloxy-4-bromo-5-methoxybenzaldehyde (4) (2.00 g, 5.80 mmol) was added dropwise over 90 min as a solution in 5 mL benzene. The reaction mixture was allowed to stir an additional 90 min at room temperature before heating to 65° C. for 5 min. Upon cooling to room temperature, TLC analysis indicated complete consumption of starting material, and the formation of a slightly more polar product. The product was isolated by repetitive washing of the solid residue with benzene (6×25 mL) at 65° C., cooling, and decanting, until TLC analysis of the wash solution indicates the absence of any product. The combined organic washings were dried over $Na_2SO_4$, and concentrated under diminished pressure. Purification by flash column chromatography (silica gel, hexanes/ethyl acetate, 5:1) afforded 2.05 g (88%) of the desired trans-cinnamate as a white solid. $^1H$ NMR (400 MHz, $CDCl_3$) δ 0.21 [s, 6H, $Si(CH_3)_2$], 1.03 [s, 9H, $SiC(CH_3)_3$], 3.80 (s,3H, $ArOCH_3$), 3.87 (s, 3H, $CO_2CH_3$), 6.38 (d, 1H, J=16.2 Hz, CH=CHCO$_2$Me), 7.00 (s, 1H, 6'-H), 7.06 (s, 1H, 3'-H), 7.97 ppm (d, 1H, J=16.3 Hz, CH=CHCO$_2$Me).

3-[2'-(tert-Butyl)dimethylsilyloxy-4'-bromo-5'-methoxyphenyl]prop-2-en-1-ol (42)

To a flame-dried 200 mL round-bottomed flask containing trans-methyl-2-(tert-butyl)dimethylsilyloxy-4-bromo-5-methoxycinnamate (41) (2.00 g, 4.98 mmol) in 20 mL anhydrous ether under nitrogen atmosphere at −40° C. was added diisobutylaluminum hydride (17.4 mL of a 1.0M solution in hexanes, 17.4 mmol, 3.50 equiv), at a rate such that the reaction temperature did not rise above −30° C. After 20 min, TLC analysis indicated complete consumption of starting material, and the formation of a more polar product. The reaction mixture was then poured into a 250 mL erlynmeyer flask containing 50 mL ice-cold 1.0M aqueous $NaHSO_4$, and the resultant biphasic mixture was stirred 5 min before extraction with ethyl acetate (3×50 mL). The combined organic solutions were washed with 50 mL brine, dried over $Na_2SO_4$, and concentrated under diminished pressure. Purification by flash column chromatography (silica gel, hexanes/ethyl acetate, 5:1) afforded 1.57 g (85%) of the desired allylic alcohol as a white solid. $^1H$ NMR (400 MHz, $CDCl_3$) δ 0.18 [s, 6H, $Si(CH_3)_2$], 1.00 [s, 9H, $SiC(CH_3)_3$],3.77 (s, 3H, $OCH_3$), 4.32 (t, 2H, J=6.8 Hz, $CH_2OH$), 6.30 (dt, 1H, J=15.8, 7.0 Hz, ArCH=CHCH$_2$OH), 6.84 (dt, 1H, J=16.0, 1.1 Hz, ArCH=CHCH$_2$OH), 6.98 and 7.00 ppm (2s, 2×1H, 6',3'-H).

3-[2'-(tert-Butyl)dimethylsilyloxy-4'-bromo-5'-methoxyphenyl]prop-2-enyl bromide (43)

To a flame-dried 100 mL round-bottomed flask containing triphenylphosphine (1.17 g, 4.46 mmol, 1.10 equiv) in 25 mL anhydrous DMF at 0° C. under nitrogen atmosphere was added bromine (0.23 mL, 4.84 mL, 1.20 equiv) through an addition funnel over 30 min, causing a faint reddish tint to the solution. A solution of 3-[2'-(tert-butyl)dimethylsilyloxy-4'-bromo-5'-methoxyphenyl]prop-2-en-1-ol (42) (1.500 g, 4.04 mmol) in 10 mL anhydrous DMF was added through an addition funnel at a steady rate over 30 min. The reaction mixture was allowed to stir at 0° C. for 10 min, at which time TLC analysis indicated complete consumption of starting material, and the formation of a less polar product. Hexanes (100 mL) was then added, and the contents of the flask were transferred to a separatory funnel containing 50 mL of saturated aqueous NH$_4$C, rinsing with an additional 50 mL hexanes and 10 mL water. The layers were separated, and the organic phase was washed with 20 mL 10% Na$_2$S$_2$O$_3$, dried over Na$_2$SO$_4$, and concentrated under diminished pressure. Purification by trituration at 0° C. (2×30 mL hexanes) to remove residual triphenylphosphine oxide, followed by flash column chromatography (silica gel, hexanes/ethyl acetate, gradient elution) afforded 1.57 g (90%) of the desired allylic bromide as a colorless, viscous oil. $^1$H NMR (400 MHz, CDCl$_3$) δ 0.20 [s, 6H, Si(CH$_3$)$_2$], 1.01 [s, 9H, SiC(CH$_3$)$_3$], 3.86 (s, 3H, OCH$_3$), 4.14 (d,2H, J=7.0 Hz, CH$_2$Br), 6.33 (dt, 1H, J=15.8, 7.2 Hz, ArCH=CHCH$_2$Br), 6.88 (d, 1H, J=16.0 Hz, ArCH=CHCH$_2$Br), 6.94 and 7.00 ppm (2s, 2×1H, 6', 3'-H).

Benzofurazan-5-yl-methyl bromide (45)

A flame-dried 200 mL round-bottomed flask equipped with a reflux condenser was charged with 5-methylbenzofurazan (44) (1.036 g, 7.72 mmol), carbon tetrachloride (75 mL), and AIBN (10 mg, catalytic). N-Bromosuccinamide (1.44 g, 8.10 mmol, 1.05 equiv) was added, and the mixture was heated to reflux 4 h in the presence of an incandescent sunlamp. Upon cooling to room temperature, the solvent was removed under diminished pressure, and the resultant yellow residue was purified by flash column chromatography (silica gel, hexanes/ethyl acetate, 5:2), affording 0.92 g (56%) of the desired bromide (Rf 0.55, 2:1 hexanes/ethyl acetate) as a white solid. $^1$H NMR (400 MHz, CDCl$_3$) δ 4.51 (s, 2H, CH$_2$Br), 7.44 (d, 1H, J=10.4 Hz, 6-H), 7.80 (s, 1H, 4-H), 7.85 ppm (d, 1H, J=10.4 Hz, 7-H).

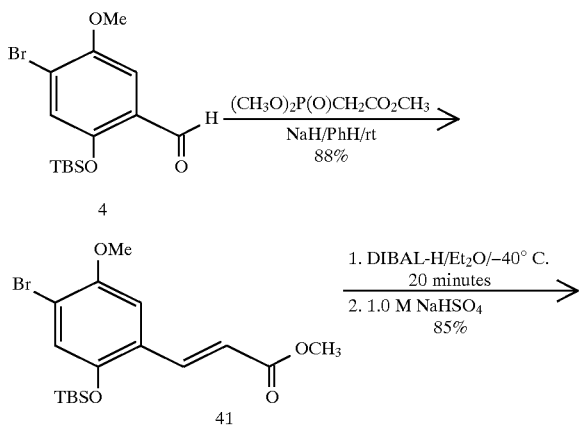

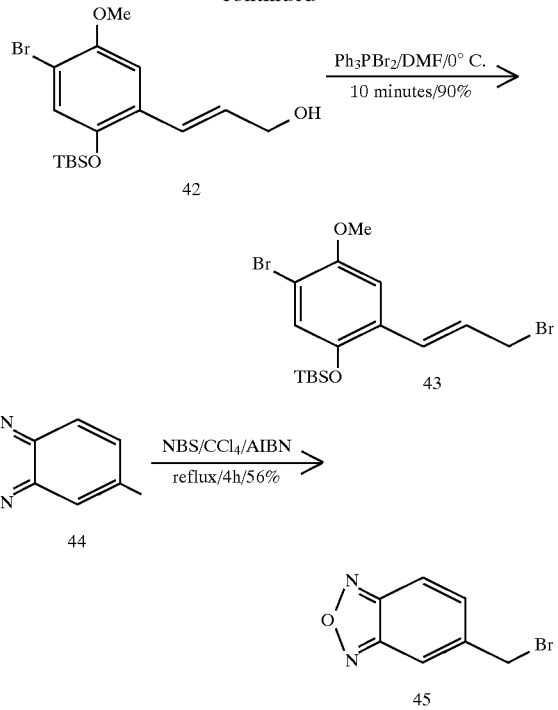

EXAMPLE 34

Synthesis of Second Aliphatic Subunit

3-Ethoxy-6-allyl-5,5-dimethylcyclohex-2-en-1-one (46)

To a flame-dried 200 mL round-bottomed flask containing diisopropylamine (4.58 mL, 32.7 mmol, 1.10 equiv) in 50 mL anhydrous THF at −78° C. under nitrogen atmosphere was added n-butyllithium (13.75 mL of a 2.27M solution in hexanes, 31.21 mmol, 1.05 equiv). After 20 min at −78° C., 3-ethoxy-5,5-dimethylcyclohex-2-en-1-one (5) (5.00 g, 29.72 mmol) was added as a solution in 5 mL THF, and the reaction mixture was allowed to stir at that temperature for 15 min before gradual warming to −60° C., and subsequent addition of allyl bromide (7.71 mL, 89.1 mmol, 3.00 equiv). The reaction mixture was then allowed to warm to −20° C. over 3 h, and was then quenched with 10 mL saturated aqueous NH$_4$Cl. The contents of the flask were then extracted with 200 mL ethyl acetate, and the organic phase was washed successively with water (100 mL) and brine (100 mL), dried over Na$_2$SO$_4$, and concentrated under diminished pressure. Purification by flash column chromatography (silica gel, hexanes/ethyl acetate, gradient elution) afforded 6.07 g (98%) of the allylated keto-enol ether as a colorless oil. $^1$H NMR (400 MHz, CDCl$_3$) δ 1.00 and 1.09 (2s, 2×3H, geminal-CH$_3$'s), 1.36 (t, 3H, OCH$_2$CH$_3$), 2.08 (dd, 1H), 3.88 (q, 2H, OCH$_2$CH$_3$), 4.99 (m, 2H, CH$_2$=CH), 5.28 (s, 1H, 2-H), 5.88 ppm (m, 1H, CH$_2$=CH).

4-Allyl-3,5,5-dimethylcyclohex-2-en-1-one (47)

To a flame-dried 200 mL round-bottomed flask containing 3-ethoxy-6-allyl-5,5-dimethylcyclohex-2-en-1-one (46) (3.10 g, 14.9 mmol) in 30 mL anhydrous ether at −78° C. under nitrogen atmosphere was added methyllithium (21.3 mL of a 1.40M solution in ether, 29.8 mmol, 2.00 equiv), slowly so that the temperature of the reaction mixture did not exceed −50° C. The mixture was allowed to stir, gradually warming to −40° C. over 3 h. The mixture was then poured into a 500 mL erlynmeyer flask containing 50 mL 1N HCl, and the resultant stirred biphasic mixture was allowed to warm to room temperature before extraction with three 50 mL portions of ethyl acetate. The combined organic solutions were washed successively with water, (50 mL) and brine (50 mL), dried over Na$_2$SO$_4$, and concentrated under diminished pressure. Purification by flash column chromatography (silica gel, hexanes/ethyl acetate, 6:1) afforded 2.26 g (85%) of the methylated enone as a colorless oil, along with the remainder of the mass balance as recovered starting material. $^1$H NMR (400 MHz, CDCl$_3$) δ 1.02 and 1.08 (2s, 2×3H, geminal-CH$_3$'s), 1.98 (s, 3H, 3-CH$_3$), 5.05 (dd, 2H, J=18.4, 10.3 Hz, CH=CH$_2$), 5.81 (dddd, 1H, J=16.5, 14.4, 8.4, 5.9 Hz, CH=CH$_2$), 5.87 ppm (s, 1H, 2-H).

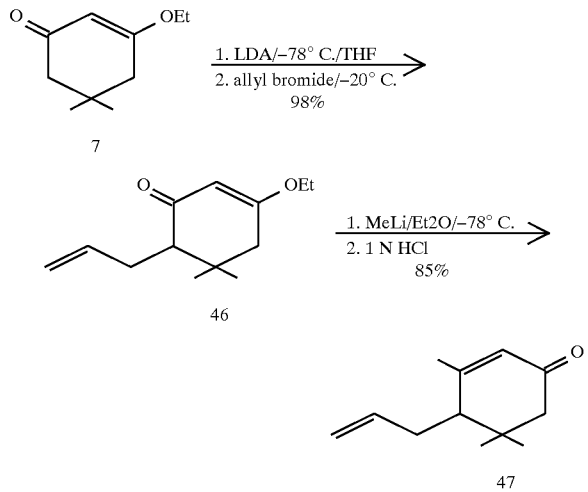

Synthesis of Additional Cyclogymopol Analogs

EXAMPLE 35

6-(4'-Nitrophenyl)methyl-3,5,5-trimethylcyclohex-2-en-1-one (48)

This compound was prepared from isophorone (2.065 g, 14.94 mmol) and p-nitrobenzyl bromide (4.06 g, 18.80 mmol, 1.25 equiv) in the manner previously described for the synthesis of enone (11), affording 1.891 g (46%), of the nitro-enone as a pale yellow oil. $^1$H NMR (400 MHz, CDCl$_3$) δ 0.98 and 1.13 (2s, 2×3H, geminal-CH$_3$'s), 1.92 (s, 3H, 3-CH$_3$), 2.17 and 231 (ABq, 2H, J$_{AB}$=18.5 Hz, 4-H), 2.38 (dd, 1H, J=9.0, 3.3 Hz, 6-H), 2.75 and 3.05 (d of ABq, 2H, J$_{AB}$=14.0 Hz, J$_A$=3.2 Hz, J$_B$=8.9 Hz, benzylic-CH$_2$), 5.84 (s, 1H, 2-H), 7.33 and 7.53 ppm (ABq, 2H, J$_{AB}$=8.2 Hz, Ar—H).

1-Methylidene-6-(4'-nitrophenyl)methyl-3,5,5-trimethylcyclohex-2-ene (49)

To a flame-dried 10 mL round-bottomed flask containing 6-(4'-Nitrophenyl)methyl-3,5,5-trimethylcyclohex-2-en-1-one (48) (114.1 mg, 0.417 mmol) in 2.0 mL anhydrous THF at 0° C. under nitrogen atmosphere was added Tebbe's reagent ({m-chloro-m-methylene[bis(cyclopentadienyl)titanium]dimethylaluminum}) (1.67 mL of a 0.5M solution in toluene, 0.835 mmol, 2.00 equiv), dropwise over a period of 5 min. The reaction mixture was then allowed to warm to room temperature, and stirred 45 min before cooling to 0° C., and the addition of 0.5 mL of 1N NaOH. The reaction mixture was then diluted with hexanes (50 mL), and filtered through a pad of celite and silica gel. The organic solution was dried over Na$_2$SO$_4$, and concentrated under diminished pressure. Purification by flash column chromatography (silica gel, hexanes/ethyl acetate, 95:5) afforded 16.1 mg (14%) of the desired diene as a colorless oil. $^1$H NMR (400 MHz, CDCl$_3$) δ 0.89 and 1.13 (2s, 2×3H, geminal-CH$_3$'s), 1.70 and 2.11 (ABq, 2H, J$_{AB}$=17.9 Hz, 4-H), 1.78 (s, 3H, 3-CH$_3$), 1.96 and 2.97 (ABq, 2H, J$_{AB}$=12.9 Hz, benzylic-CH$_2$), 2.30 (dd, 1H, J=12.0, 11.9 Hz, 6-H), 3.91 and 4.53 (2s, 2×1H, methylidene-CH$_2$), 5.81 (s, 1H, 2-H), 7.17 (d, 2H, J=8.5 Hz, 2', 6'-H), 8.08 ppm (d, 2H, J=8.5 Hz, 3',5'-H). [This compound is also referred to as Compound "I" or 120190]

EXAMPLE 36

1-Hydroxy-1-(4'-nitrophenyl)methyl-2-methylidene-4,6,6-trimethylcyclohex-3-ene (50)

To a flame-dried 10 mL round-bottomed flask containing 31.1 mg (0.115 mmol) 1-methylidene-6-(4'-nitrophenyl)methyl-3,5,5-trimethylcyclohex-2-ene (49) in 1.6 mL dichloromethane at room temperature was added selenium (IV) oxide (6.4 mg, 0.057 mmol, 0.50 equiv), followed by (tert-butyl)hydroperoxide (76.4 mL of a 3.0M solution in 2,2,4-trimethylpentane, 0.229 mmol, 2.00 equiv), and the reaction mixture was allowed to stir at room temperature for 42 h. The solvent was then removed under diminished pressure, and the residue was purified by flash column chromatography (silica gel, hexanes/ethyl acetate, 15:1), affording 4.2 mg (13%) of the desired tertiary alcohol as a pale yellow oil. $^1$H NMR (400 MHz, CDCl$_3$) δ 0.89 and 1.17 (2s, 2×3H, geminal-CH$_3$'s), 1.81 (s, 3H, 3-CH$_3$), 1.95 and 2.35 (ABq, 2H, J$_{AB}$=18.3 Hz, 4-H), 2.69 and 3.02 (ABq, 2H, J$_{AB}$=13.0 Hz, benzylic-CH$_2$), 4.23 and 4.61 (2s, 2×1H, methylidene-CH$_2$), 5.88 (s, 1H, 2-H), 7.22 (d, 2H,J=9.6Hz, 2',6'-H), 8.05 ppm (d, 2H, J=9.6 Hz, 3',5'-H). [This compound is also referred to as Compound "AA" or 120269]

EXAMPLE 37

1-Methylidene-6-(4'-nitrophenyl)thio-3,5,5-trimethylcyclohex-2-ene (52)

To a flame-dried 100 mL round-bottomed flask containing diisopropylamine (338 mL, 2.41 mmol, 1.1 equiv) in 10 mL anhydrous THF at −72° C. under nitrogen atmosphere was added n-butyllithium (1.00 mL of a 2.41M solution in hexanes, 2.41 mmol, 1.10 equiv). After 20 min at −78° C., isophorone (329 mL, 2.19 mmol) was added dropwise as a solution in 2 mL THF, and the reaction mixture was allowed to gradually warm to 0° C. over 90 min before the addition of 4-nitrophenyldisulfide (1.19 g, 3.29 mmol, 1.50 equiv) as a solution in 5 mL THF. The resultant dark-orange reaction solution was allowed to warm to room temperature, stirring 15 h before cooling to 0° C., and quenching with 10 mL saturated aqueous NH$_4$Cl. The reaction mixture was then extracted with 60 mL ethyl acetate, and the organic phase was washed with brine (40 mL), dried over Na$_2$SO$_4$, and concentrated under diminished pressure. Purification by flash column chromatography (silica gel, hexanes/ethyl acetate, 6:1) afforded 462 mg (72%) of the thiophenyl-substituted enone as an orange oil (Rf 0.52, 2:1 hexanes/ethyl acetate). This intermediate enone was then carried on to the next step without further purification. To a flame-dried 10 mL round-bottomed flask containing the thiophenyl-substituted isophorone (25.0 mg, 0.086 mmol) in 0.5 mL anhydrous THF at 0° C. under nitrogen atmosphere was added Tebbe's reagent ({m-chloro-m-methylene[bis (cyclopentadienyl)titanium]dimethylaluminum}) (345 mL of a 0.5M solution in toluene, 0.172 mmol, 2.00 equiv), dropwise over a period of 5 min. The reaction mixture was then allowed to warm to room temperature, and stirred 4 h before cooling to 0° C., and the addition of 0.5 mL of methanol. The reaction mixture was then diluted with 4:1 hexanes/ethyl acetate (50 mL), and filtered through a pad of celite and silica gel. The organic solution was dried over Na₂SO₄, and concentrated under diminished pressure. Purification by flash column chromatography (basic alumina, Brockman, hexanes/ethyl acetate, 10:1) afforded 2.8 mg (11%) of the desired diene as a colorless oil (Rf 0.67, 2:1 hexanes/ethyl acetate). $^1$H NMR (400 MHz, CDCl₃) δ 1.04 and 1.15 (2s, 2×3H, geminal-CH₃'s), 1.79 (s, 3H, 3-CH₃), 1.84 and 2.23 (ABq, 2H, $J_{AB}$=17.4 Hz, 4-H), 3.63 (s, 1H, 6-H), 4.62 and 4.74 (2s, 2×1H, methylidene-CH₂), 5.87 (s, 1H, 2-H), 7.46 (d, 2H, J=9.6 Hz, 2', 6'-H), 8.11 ppm (d, 2H, J=9.6 Hz, 3', 5'-H). [This compound is also referred to as Compound "CC" or 120280]

EXAMPLE 38
8-(2'-Acetoxy-4'-bromo-5'-methoxyphenyl)methyl-5,7,7-trimethylspiro[2.5]oct-4-ene (53)

To a flame-dried 10 mL round-bottomed flask containing 20.0 mg (0.051 mmol) 1-methylidene-6-(2'-acetoxy-4'-bromo-5'-methoxyphenyl)methyl-3,5,5-trimethylcyclohex-2-ene (17) in 1 mL 1,2-dichloroethane under nitrogen atmosphere at 0° C. was added diethylzinc (254 mL of a 1.0M solution in hexanes, 0.255 mmol, 5.0 equiv). Chloroiodomethane (37 mL, 0.510 mmol, 10.0 equiv) was added dropwise, and the mixture was allowed to warm to room temperature. After 9 h, the reaction mixture was quenched at 0° C. with saturated aqueous NH₄Cl, and the reaction mixture was extracted with ethyl acetate (50 mL). The organic phase was washed with brine (20 mL), dried over Na₂SO₄, and concentrated under diminished pressure. Purification by flash column chromatography (silica gel, hexanes/ethyl acetate, gradient elution) afforded 20 mg (96%) of the spirocyclopropane as a colorless, viscous oil. $^1$H NMR (400 MHz, CDCl₃) δ −0.07 (ddd, 1H, J=11.0, 9.3, 5.9 Hz, cyclopropyl-H), 0.16 (ddd, 1H, J=11.5, 9.4, 6.1 Hz, cyclopropyl-H), 0.32 (ddd, 1H, J=10.1, 5.8, 5.8 Hz, cyclopropyl-H), 0.43 (ddd, 1H, J=9.8, 6.1, 6.1 Hz, cyclopropyl-H), 1.03 and 1.06 (2s, 2×3H, geminal-CH₃'s), 1.60 and 1.98 (ABq, 2H, $J_{AB}$=17.8 Hz, 6H), 1.69 (s, 3H, 5-CH₃), 2.25 (s, 3H, acetate-CH₃), 2.39 and 2.65 (d of ABq, 2H, $J_{AB}$=13.6 Hz, $J_A$=10.0 Hz, $J_B$=3.4 Hz, benzylic-CH₂), 3.86 (s, 3H, OCH₃), 4.68 (s, 4-H), 6.69 (s, 1H, 6'-H), 7.18 ppm (s, 1H, 3'-H). [This compound is also referred to as Compound "DD" or 120299]

EXAMPLE 39
6-[2'-(tert-Butyl)dimethylsilyloxy-4'-bromo-5'-methoxyphenyl]methyl-3-ethoxy--5,5-dimethylcyclohex-2-en-1-one (54)

This compound was prepared from 3-ethoxy-5,5-dimethylcyclohex-2-en-1-one (7) (1.30 g, 7.73 mmol) and benzylic bromide (6) (1.53 g, 3.73) in the manner previously described for the synthesis of enone (11), affording 1.71 g (92%) of the desired b-ethoxy enone as a white solid. $^1$H NMR (400 MHz, CDCl₃) δ 0.20 and 0.22 [2s, 2×3H, Si(CH₃)₂], 9H, SiC(CH₃)₃], 1.01 and 1.04 (2s, 2×3H, geminal-CH₃'s), 1.37 (t, 3H, J=6.9 Hz, OCH₂CH₃), 3.82 (s, 3H, OCH₃), 3.90 (q, 2H, OCH₂CH₃), 5.32 (br s, 1H, 2-H), 6.77 (s, 1H, 6'-H), 6.93 ppm (s, 1H, 3'-H).

4-[2'-(tert-Butyl)dimethylsilyloxy-4'-bromo-5'-methoxyphenyl]methyl-3,5,5-trimethylcyclohex-2-en-1-one (55)

To a flame-dried 50 mL round-bottomed flask containing 6-[2'-(tert-butyl)dimethylsilyloxy-4'-bromo-5'-methoxyphenyl]methyl-3-ethoxy-5,5-dimethylcyclohex-2-en-1-one (54) (1.005 g, 2.02 mmol) in 10 mL anhydrous ether at −78° C. under nitrogen atmosphere was added methyllithium (4.33 mL of a 1.40M solution in ether, 6.06 mmol, 3.00 equiv). After 3 h at −78° C., 1.0M NaHSO₄ (5 mL) was added, and the reaction mixture was allowed to stir overnight, warming to room temperature. The biphasic reaction mixture was then extracted with ethyl acetate (100 mL), and the organic phase was washed with brine (50 mL), dried over Na₂SO₄, and concentrated under diminished pressure. Purification by flash column chromatography (silica gel, hexanes/ethyl acetate, gradient elution) afforded 0.850 g (90%) of the desired enone as a white solid. $^1$H NMR (400 MHz, CDCl₃) δ 0.24 and 0.26 [2s, 2×3H, Si(CH₃)₂],1.01 [s, 9H, SiC(CH₃)₃], 1.04 and 1.14 (2s, 2×3H, geminal-CH₃'s), 1.41 (s1 d, 3H, J=1.1 Hz, 3-CH₃), 2.11 and 2.50 (ABq, 2H, $J_{AB}$=17.7 Hz, benzylic-CH₂), 3.22 (br d, 1H, J_8.0 Hz, 4-H), 3.80 (s, 3H, OCH₃), 5.83 (br s, 1H, 2-H), 6.57 (s, 1H, 6'-H), 6.98 ppm (s, 1H, 3'-H).

1-Methylidene-4-(2'-hydroxy-4'-bromo-5'-methoxyphenyl) methyl-3,5,5-trimethylcyclohex-2-ene (56)

This compound was prepared from 4-[2'-(tert-butyl)dimethylsilyloxy-4'-bromo-5'-methoxyphenyl]methyl--3,5,5-trimethylcyclohex-2-en-1-one (55) (100 mg, 0.214 mmol) in the manner previously described for the synthesis of olefin (13), affording 43 mg (57%) of the desired diene as a colorless oil. $^1$H NMR (400 MHz, CDCl₃) δ 0.87 and 1.07 (2s, 2×3H, geminal-CH₃'s), 1.38 (s, 3H, 3-CH₃), 1.95 and 2.48 (ABq, 2H,$J_{AB}$=17.6 Hz, 6-H), 2.02 (dd, 1H, J=11.6, 4.5 Hz, 4-H), 2.46 and 2.94 (d of ABq, 2H, $J_{AB}$=17.0 Hz, $J_A$=13.1 Hz, $J_B$=4.0 Hz, benzylic-CH₂), 3.80 (s, 3H, OCH₃), 4.74 (br s, 2H, methylidene-CH and OH), 4.81 (s, 1H, methylidene-CH), 5.93 (s, 1H, 2-H), 6.67 (s, 1H, 6'-H), 7.00 ppm (s, 1H, 3'-H). [This compound is also referred to as Compound "EE" or 120303]

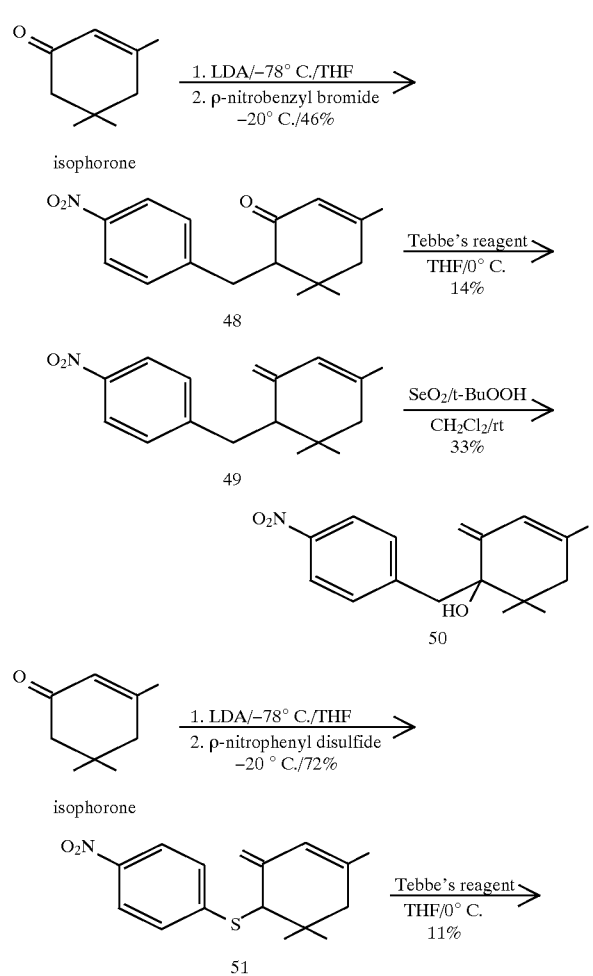

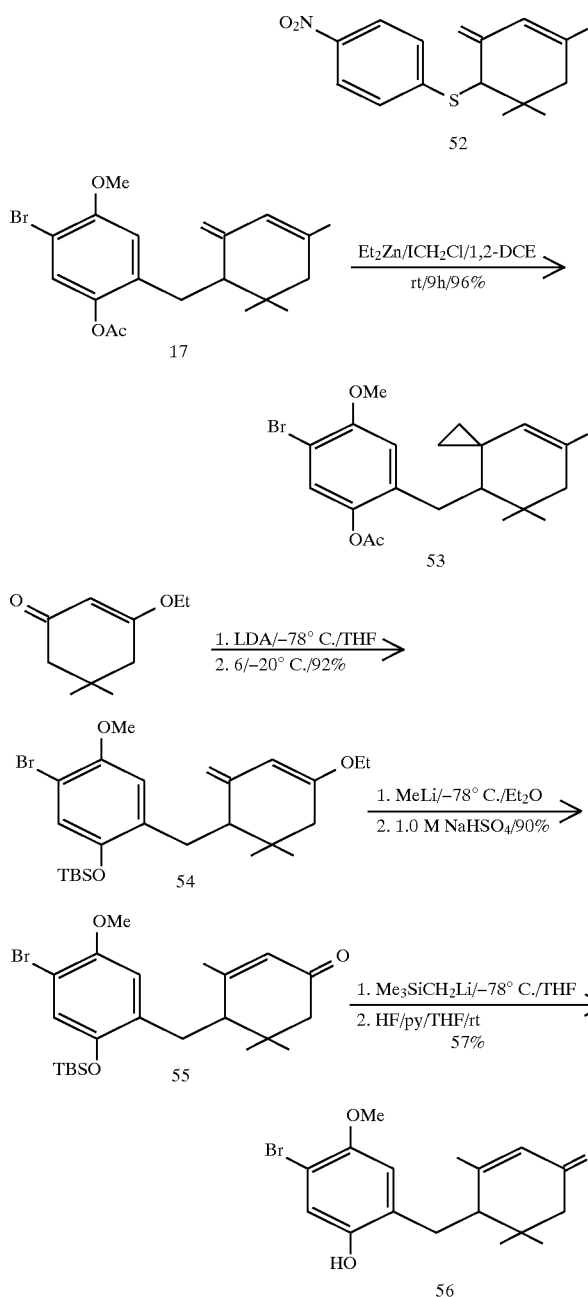

EXAMPLE 40
1-Methylidene-6-(benzofurazan-5'-yl)methyl-3,5,5-trimethylcyclohex-2-ene (58)

This compound was prepared from isophorone (1.475 mL, 9.83 mmol) and benzofurazan-5-yl-methyl bromide (45) (0.838 g, 3.93 mmol) in three steps in the manner previously described for the synthesis of olefin (13), affording the desired diene as a pale orange oil (Rf 0.41, 2:1 hexanes/ethyl acetate) in 33% overall yield. $^1$H NMR (400 MHz, CDCl$_3$) δ 0.90 and 1.15 (2s, 2×3H, geminal-CH$_3$'s), 1.78 (s, 3H, 3-CH$_3$), 1.72 and 2.13 (ABq, 2H, J$_{AB}$=18.3 Hz, 4-H), 2.02 and 2.95 (d of ABq, 2H, J$_{AB}$=13.0 Hz, J$_A$, J$_B$=3.2 Hz, benzylic-CH$_2$), 2.33 (dd, 1H, J=13.0, 13.0 Hz, 6-H), 4.02 and 4.54 (2s, 2×1H, methylidene-CH$_2$), 5.83 (s, 1H, 2-H), 7.16 (d, 1H, J=9.2 Hz, 6'-H), 7.37 (s, 1H, 2'-H), 7.67 ppm (d, 1H, J=9.3 Hz, 5'-H). [This compound is also referred to as Compound "FF" or 120321]

EXAMPLE 41
6-[trans-(2'-Hydroxy-4'-bromo-5'-methoxyphenyl)-1-propenyl]-3,5,5-trimethylcyclohex-2-en-1-one (59)

This compound was prepared from isophorone (0.40 g, 2.88 mmol) and 3-[2'-(tert-butyl)dimethylsilyloxy-4'-bromo-5'-methoxyphenyl]prop-2-enyl bromide (43) (0.50 g, 1.15 mmol) in the manner previously described for the synthesis of enone (11), affording 452 mg (80%) of the desired enone as a yellow oil. $^1$H NMR (400 MHz, CDCl$_3$) δ 0.16 an 0.17 [2s, 2×3H, Si(CH$_3$)$_2$], 0.97 and 1.09 (2s, 2×3H, geminal-CH$_3$'s), 1.00 [s, 9H, SiC(CH$_3$)$_3$], 1.92 (s, 3H, 3-CH$_3$), 3.85 (s, 3H, OCH$_3$), 5.85 (s, 1H,2-H), 6.21 (ddd, 1H, J=15.8, 7.1, 7.1 Hz, ArCHCH), 6.59 (d, 1H, J=16.0 Hz, ArCHCH), 6.93 and 6.94 ppm (2s, 2×1H, Ar—H).

1-Methylidene-6-[trans-(2'-Hydroxy-4'-bromo-5'-methoxyphenyl)-1-propenyl]-3,5,5-trimethylcyclohex-2-ene (60)

This compound was prepared from 6-[trans-(2'-hydroxy-4'-bromo-5'-methoxyphenyl)-1-propenyl]-3,5,5-trimethylcyclohex-2-en-1-one (59) (50 mg, 0.10 mmol) in the manner previously described for the synthesis of olefin (13), affording 23.0 mg (60%) of the desired triene as a colorless oil. $^1$H NMR (400 MHz, CDCl$_3$) δ 0.88 and 1.04 (2s, 2×3H, geminal-CH$_3$'s), 1.74 (s, 3H, 3-CH$_3$), 3.83 (s, 3H, OCH$_3$), 4.62 and 4.81 (2s, 2×1H, methylidene-CH$_2$), 5.13 (s, 1H, OH), 5.85 (s, 1H, 2-H), 6.07 (ddd, 1H, J=15.4, 6.9, 6.9 Hz, ArCHCH), 6.32 (d, 1H, J=16.2 Hz, ArCHCH), 6.76 (s, 1H, 6'-H), 7.03 ppm (s, 1H, 3'-H). [This compound is also referred to as Compound "GG" or 120331]

EXAMPLE 42
trans-4-Allyl-6-(2'-hydroxy-4'-bromo-5'-methoxyphenyl)methyl-3,5,5-trimethylcyelohex-2-en-1-one (61)

This compound was prepared from 4-allyl-3,5,5-dimethylcyclohex-2-en-1-one (47) (1.00 g, 5.61 mmol) and benzylic bromide (6) (0.921 g, 2.24 mmol) in the manner previously described for the synthesis of enone (11), affording 764 mg (67%) of the desired trans-enone as a yellow oil. $^1$H NMR (400 MHz, CDCl$_3$) δ 0.21 and 0.22 [2s, 2×3H, Si(CH$_3$)$_2$], 0.97 and 0.99 (2s, 2×3H, geminal-CH$_3$'s), 0.99 [s, 9H, SiC(CH$_3$)$_3$], 1.96 (s, 3H, 3-CH$_3$), 3.81 (s, 3H, OCH$_3$), 5.02 (dd, 2H, J=16.0, 10.0 Hz, CH═CH$_2$), 5.82 (m, 1H, CH═CH$_2$), 5.86 (s, 1H, 2-H), 6.77 (s, 1H, 6'-H), 6.94 ppm (s, 1H, 3'-H).

trans-4-(2-Hydroxy)ethyl-6-(2'-hydroxy-4'-bromo-5'-methoxyphenyl)methyl-3,5,5-trimethylcyclohex-2-en-1-one (62)

A stream of ozone was bubbled through a solution of trans-4-allyl-6- (2'-hydroxy-4'-bromo-5'-methoxyphenyl)methyl-3,5,5-trimethylcyclohex-2-en-1-one (61) (207 mg, 0.407 mmol) in 60 mL dichloromethane at −78° C. in a 100 mL round-bottomed flask with 0.5 mL of a 0.05% solution of Solvent Red #19 in absolute ethanol, until the color of the indicator just began to disappear. Methyl sulfide (2 mL, large excess) was then added, and the reaction mixture was allowed to warm to room temperature overnight, followed by removal of the solvent under diminished pressure. The crude aldehyde thus obtained was then dissolved in 20 mL THF, and cooled to −78° C. Lithium tris[(3-ethyl-3-pentyl)-oxy]aluminohydride (LiTEPA) (0.90 MnL of a 0.5M solution in THF, 0.45 mmol, 1.1 equiv) was then added at a steady rate over 40 min using a syringe pump. The reaction mixture was allowed to stir at −78° C. for an additional 2 h before the addition of 10 mL 1:1 methanol hexanes/ethyl water. Upon warming to room temperature, the mixture was extracted with ethyl acetate (3×30 mL), and the combined organic layers were dried over Na$_2$SO$_4$, and concentrated under diminished pressure. Purification by flash column chromatography (silica gel, hexanes/ethyl acetate, gradient elution) afforded 162 mg (78% for two steps) of the desired hydroxy-enone as a colorless, oily solid. $^1$H NMR (400 MHz, CDCl$_3$) δ 0.21 and 0.22 [2s, 2×3H, Si(CH$_3$)$_2$], 0.95 and 1.00 (2s, 2×3H, geminal-CH$_3$'s), 0.99 [s, 9H, SiC(CH$_3$)$_3$],1.99 (s, 3H, 3-CH$_3$), 3.65 (m, 1H, CHHOH), 3.72 (br s, 2H, CHHOH), 3.81 (s, 3H, OCH$_3$), 5.81 (s, 1H, 2-H), 6.82 (s, 1H, 6'-H), 6.94 ppm (s, 1H, 3'-H).

trans-1-Methylidene-4-(2-hydroxy)ethyl-6-(2'-hydroxy-4'-bromo-5'-methoxyphenyl)methyl-3,5,5-trimethylcyclohex-2-ene (63)

This compound was prepared from trans-4-(2-hydroxy)ethyl-6-(2'-hydroxy-4'-bromo-5'-methoxyphenyl)methyl-3,5,5-trimethylcyclohex-2-en-1-one (62) (50 mg, 0.098 mmol) in the manner previously described for the synthesis of olefin (13), using 5.0 equiv of the (trimethyl)silylmethyllithium reagent, affording 12 mg (26%) of the desired diene as a colorless, oily solid. $^1$H NMR (400 MHz, CDCl$_3$) δ 0.80 and 1.18 (2s, 2×3H, geminal-CH$_3$'s), 1.86 (s, 3H, 3-CH$_3$), 3.49 (m, 1H, CHHOH), 3.64 (m, 1H, CHHOH), 3.82 (s, 3H, OCH$_3$), 4.17 and 4.62 (2s, 2×1H, methylidene-CH$_2$), 4.52 (br s, 1H, ArOH), 4.78 (br s, 1H, CH$_2$OH), 5.90 (s, 1H, 2-H), 6.52 (s, 1H, 6'-H), 6.98 ppm (s, 1H, 3'-H). [This compound is also referred to as Compound "JJ" or 120382]

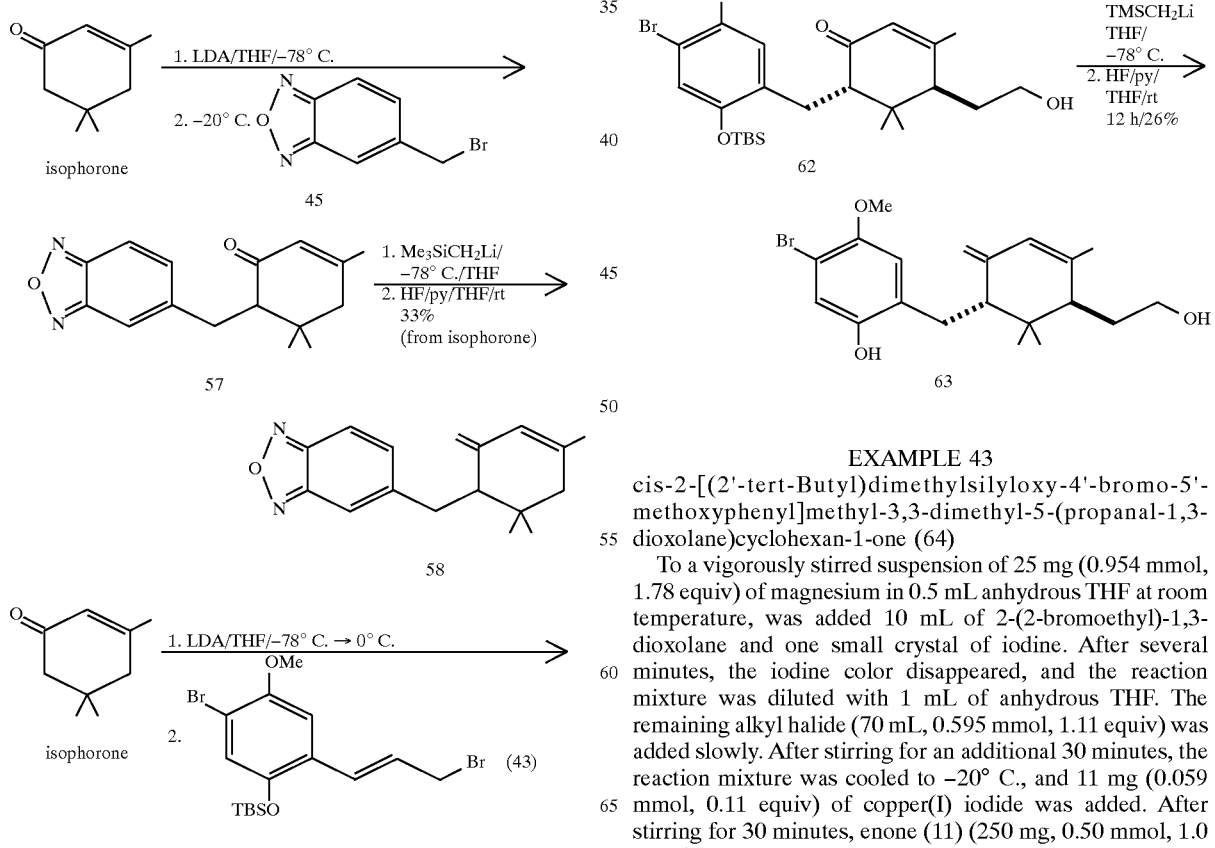

EXAMPLE 43 cis-2-[(2'-tert-Butyl)dimethylsilyloxy-4'-bromo-5'-methoxyphenyl]methyl-3,3-dimethyl-5-(propanal-1,3-dioxolane)cyclohexan-1-one (64)

To a vigorously stirred suspension of 25 mg (0.954 mmol, 1.78 equiv) of magnesium in 0.5 mL anhydrous THF at room temperature, was added 10 mL of 2-(2-bromoethyl)-1,3-dioxolane and one small crystal of iodine. After several minutes, the iodine color disappeared, and the reaction mixture was diluted with 1 mL of anhydrous THF. The remaining alkyl halide (70 mL, 0.595 mmol, 1.11 equiv) was added slowly. After stirring for an additional 30 minutes, the reaction mixture was cooled to −20° C., and 11 mg (0.059 mmol, 0.11 equiv) of copper(I) iodide was added. After stirring for 30 minutes, enone (11) (250 mg, 0.50 mmol, 1.0 equiv) in 0.5 mL of THF was added dropwise. After stirring for 30 minutes, the reaction was then allowed to warm to room temperature (turning black), and subsequently poured into a 4:1 mixture of saturated aqueous NH$_4$Cl/saturated aqueous NH$_4$OH solution (2 mL). The reaction mixture was extracted with ether, dried over Na$_2$SO$_4$ and evaporated under diminished pressure. Purification by flash column chromatography (silica gel, hexanes/ethyl acetate 85:15), afforded 20 mg (7%) of the desired ketone (64), 82 mg (30%) of the C-2 diastereoisomer (65), and 95.3 mg (38%) of unreacted starting material. $^1$H NMR (400 MHz, CDCl$_3$) δ 0.22 (s, 6H, Si(CH$_3$)$_2$), 1.02 (s, 9H, SiC(CH$_3$)$_3$),1.02 and 1.06 (2s, 2×3H, geminal-CH$_3$'s), 1.48 (m, 3H), 1.55 (m, 1H), 1.69 (m, 2), 1.92 (m, 1H), 2.17 (m, 2H, 5-H), 2.46 (apparent t, 1H, J=8.0, Hz, 2-H), 2.85 (d, 2H, J=8.1 Hz, benzylic-CH$_2$), 3.82 (s, 3H, OCH$_3$), 3.86 and 3.97 [2m, 2×2H, dioxolane-(CH$_2$)$_2$], 4.84 (m, 1H, dioxolane-CH), 6.65 (s, 1H, 6'-H), 6.95 ppm (s, 1H, 3'-H).

cis-1-Methylidene-2-(2'-hydroxy-4'-bromo-5'-methoxyphenyl)methyl-3,3-dimethyl-5-(propanal-1,3-dioxolane)cyclohexane (66)

To a solution of 2-[(2'-tert-butyl)dimethylsilyloxy-4'-bromo-5'-methoxyphenyl]methyl-3,3-dimethyl-5-(propanal-1,3-dioxolane)cyclohexan-1-one (64) (28 mg, 0.05 mmol, 1.00 equiv) in 2 mL of anhydrous THF at −78° C. was added (trimethyl)silylmethyllithium (74 mL of a 1.0M solution in pentane, 0.074 mmol, 1.50 equiv). After 10 minutes of stirring at −78° C., the reaction was quenched at −78° C. with 1 mL of saturated aqueous NH$_4$Cl. The reaction mixture was then extracted with ethyl acetate, dried over Na$_2$SO$_4$, and concentrated under diminished pressure. Purification by flash column chromatography (silica gel, hexanes/ethyl acetate 4:1) gave 27.3 mg (84%) of the desired tertiary alcohol intermediate. Twenty milligrams of this intermediate was placed in a 10 mL Nalgene vial containing 2 mL of dry THF; 0.214 mL of HF/pyridine complex was added, and the mixture was allowed to stir at room temperature for 32 h. The contents of the vial were transferred to a separatory funnel containing 5 mL of ethyl acetate and 3 mL of 1M aqueous NaHSO$_4$. The layers were separated, and the organic phase was washed with 2 mL of brine, dried over Na$_2$SO$_4$, and concentrated under diminished pressure. Purification by flash column chromatography (silica gel, hexanes/ethyl acetate, 9:1) gave 11 mg (83%) of the intermediate phenol as a colorless oil. $^1$H NMR (400 MHz, CDCl$_3$) δ 0.79 and 1.07 (2s, 2×3H, geminal-CH$_3$'s), 1.14 (m, 1H), 1.31 and 1.66 [2 m, 2×2H, propanal-(CH$_2$)$_2$], 1.55 (m, 3H), 2.24 (dd, 1H, J=7.5 Hz, 2-H), 2.72 (m, 2H, benzylic-CH$_2$), 3.78 (s, 3H, OCH$_3$), 3.84 and 3.98 [2m, 2×2H, dioxolane-(CH$_2$)$_2$], 4.63 and 4.86 (2s, 2×1H, methylidene-CH$_2$), 4.68 (s, 1H, OH), 4.84 (dd, 1H, J=4.8, 4.8 Hz, dioxolane-CH), 6.80 (s, 1H, 6'-H), 6.93 ppm (s, 1H, 3'-H). [This compound is also referred to as Compound "W" or 120241]

EXAMPLE 44 cis-1-Methylidene-2-(2'-hydroxy-4'-bromo-5'-methoxyphenyl)methyl-3,3-dimethyl-5-(3-hydroxypropyl)cyclohexane (67)

To a 5 mL round-bottomed flask containing 4.0 mg (0.009 mmol) of cis-1-methylidene-2-(2'-hydroxy-4'-bromo-5'-methoxyphenyl)methyl-3,3-dimethyl-5-(propanal-1,3-dioxolane)cyclohexane (66) in 100 mL of pyridine at 0° C. was added 2 mL of acetic anhydride, and the reaction mixture was allowed to warm to room temperature and stirred for 1.5 h. The reaction mixture was then diluted with 2 mL of ethyl acetate, and the organic phase was washed successively with 10% aqueous HCl (3×1 mL), saturated aqueous NaHCO$_3$ solution (2×1 mL), and brine, dried over Na$_2$SO$_4$, and concentrated under diminished pressure to give 4.3 mg (100%) of acetate that was used directly in the next step without further purification. To a solution of this intermediate (4.3 mg) in 1 mL of THF with 0.4 mL of water was added 0.2 mL of 1 M HCl, and the reaction mixture was stirred at room temperature for 16 h, then diluted with ethyl acetate. The organic solution was then washed with brine, dried over Na$_2$SO$_4$, and concentrated under diminished pressure. Purification by flash column chromatography (silica gel, hexanes/ethyl acetate, 4:1) to give 2.5 mg (64%) of pure aldehyde as a colorless oil. The aldehyde thus obtained (2.5 mg, 0.006 mmol) was dissolved in 1 mL of methanol, and cooled to 0° C. Sodium borohydride (1.0 mg, 0.017 mmol, 3 mol equiv) was added, and after 1 h of stirring, 2 mL water was added, and the reaction mixture was extracted with 30 mL ethyl acetate. The organic phase was dried over Na$_2$SO$_4$, and concentrated under diminished pressure. Purification by flash column chromatography (silica gel, hexanes/ethyl acetate 4:1) afforded 2.3 mg (91%) of the desired alcohol as a colorless oil. $^1$H NMR (400 MHz, CDCl$_3$) δ 0.86 and 1.09 (2s, 2×3H, geminal-CH$_3$'s), 1.12 (m, 1H), 1.25 (m,4H), 1.56 (m, 3H), 2.25 (dd, 1H, J=7.0 Hz, 2.48 (dd, 1H, J=2.5 and 8.3 Hz, 2-H), 2.73 (d, 1H, J=3.0 Hz) and 2.75 (s, 1H) [benzylic-CH$_2$],3.65 (apparent t, 2H, J=6.6 Hz, CH$_2$OH), 3.80 (s, 3H, OCH$_3$), 4.64 (s, 1H, OR), 4.70 and 4.87 (2s, 2×1H, methylidene-CH$_2$), 6.69 (s, 1H, 6'-H), 6.94 ppm (s, 1H, 3'-H). [This compound is also referred to as Compound "X" or 120257]

EXAMPLE 45

(5R, 6)-6-[2'-(tert-Butyl)dimethylsilyloxy-4'-bromo-5'-methoxyphenyl)methyl-5methylcyclohex-2-en-1-one (69)

To a solution of lithium diisopropylamide (4.65 mL of a 2.0M solution in THF, 9.30 mmol, 2.20 equiv) in 15 mL of anhydrous THF and 4.4 mL of dry HMPA at −35° C. was added dropwise ketosulfoxide (68) (prepared from (R)-(+)-pulegone according to the method of Oppolzer and Petrzika; Helv. Chim. Acta 1978, 61, 2755) in 5 mL of dry THF. The reaction mixture was stirred at −35° C. for 3 h, after which 2-(tert-butyl)dimethylsilyloxy-4-bromo-5-methoxybenzyl bromide (6) was added dropwise as a solution in 10 mL of anhydrous THF. The reaction mixture was allowed to stir for an additional 2 h at −35° C., quenched with 1M aqueous NaHSO$_4$ (15 mL) and extracted with ether (50 mL). The organic layer was washed with water (3×15 mL) and brine (1×15 mL), then dried over Na$_2$SO$_4$ and concentrated under diminished pressure to afford 2.37g of the intermediate ketosulfoxide as a pale yellow oil, which was used directly in the next step without purification. A solution of the intermediate ketosulfoxide (2.37 g, 4.20 mmol) and CaCO$_3$ (0.40 g, 3.90 mmol) in 90 mL of carbon tetrachloride was brought to reflux for 3 h. Upon cooling to room temperature, the reaction mixture was filtered and the solvent was removed under diminished pressure. Purification by flash column chromatography (silica gel, hexanes/ethyl acetate, 95:5) afforded 550 mg (30%) of the desired enone. $^1$H NMR (400 MHz, CDCl$_3$) δ 0.18 and 0.22 [2s, 2×3H, Si(CH$_3$)$_2$], 1.03 [s, 9H, SiC(CH$_3$)$_3$], 1.05 (d, 3H, J=8.0 Hz, 5-CH$_3$), 2.07 (m, 2H), 2.50 (m, 1H,6-H), 2.65 (m, 1H), 2.91 (m, 2H, benzylic-CH$_2$), 3.80 (s, 3H, OCH$_3$), 6.02 (d, 1H, J=9.4 Hz, 2-H), 6.70 (s, 1H, 6'-H), 6.85 (ddd, 1H, J=9.6, 4.1, 3.2 Hz, 3-H), 6.98 ppm (s, 1H, 3'-H).

(5R,6S)-6 [2'-(tert-Butyl)dimethylsilyloxy-4'-bromo-5'-methoxyphenyl)methyl-3,5-dimethylcyclohex-2-en-1-one (70)

To a suspension of copper(I) iodide (1.36 mg) in 0.5 mL of anhydrous ether at 0° C. was added methylmagnesium bromide (222 mL of a 3.0 M solution in ether, 0.665 mmol, 1.00 equiv), causing the solution to turn dark. A solution of enone (69) (310 mg, 0.665 mmol) in 1 mL of anhydrous ether was the added over a period of 2 minutes keeping the temperature below 5° C. After the addition was complete, the mixture was stirred at 0° C. for an additional 30 minutes, at which time phenylselenenyl bromide (157 mg, 0.665 mmol) in 0.5 mL of anhydrous THF was added, keeping the temperature below 10° C. The resulting mixture was stirred for 10 minutes, poured into water (2 mL) and extracted with ether (5 mL). The organic phase was washed twice with water (2 mL), dried over $Na_2SO_4$ and concentrated under diminished pressure. The resultant oil was dissolved in 2 mL of dry dichloromethane and 162 mL of pyridine, and to this a solution of hydrogen peroxide 35% (181 mL) in 162 mL of water was added dropwise, keeping the temperature between 30°–35° C. and warming if necessary to initiate the reaction. The mixture was stirred at room temperature for 30 minutes, and then poured into a separatory funnel containing dichloromethane-saturated aqueous $NaHCO_3$. After extraction of the mixture with dichloromethane, the organic solution was washed successively with 10% aqueous HCl and brine, and dried over $Na_2SO_4$. The solvent was removed under diminished pressure, and the residue was purified by flash column chromatography (silica gel, hexanes/ethyl acetate, 9:1), affording 157 mg (60%) of the desired enone as a colorless oil. $^1$H NMR (400 MHz, $CDCl_3$) δ 0.15 and 0.20 [2s, 2×3H, $Si(CH_3)_2$], 0.97 [s, 9H, $SiC(CH_3)_3$], 0.95 (d, 3H, J=8.0 Hz, 5-$CH_3$), 1.90 (s, 3H, 3-$CH_3$), 1.95 (m, 2H), 2.38 (m, 1H), 2.59 (m, 1H, 6-H), 2.87 (m, 2H, benzylic-$CH_2$), 3.79 (s, 3H, $OCH_3$), 5.86 (s, 1H, 2-H), 6.69 (s, 1H, 6'-H), 6.96 ppm (s, 1H, 3'-H).

(5R,6S)-1-Methylidene-6-(2'-acetoxy-4'-bromo-5'-methoxyphenyl)methyl-5-methylcyclohex-2-ene (71)

To a solution of (5R,6S)-6-[(2'-tert-butyl) dimethylsilyloxy-4'-bromo-5'-methoxyphenyl)methyl-5-methylcyclohex-2-en-1-one (69) (63 mg, 0.139 mmol, 1.00 equiv) in 2 mL of anhydrous THF at −78° C. was added (trimethyl)silylmethyllithium (222 mL of a 1.0M solution in pentane, 0.222 mmol, 1.60 equiv). After 10 minutes of stirring at −78° C., the reaction was quenched at −78° C. with 1 mL of saturated aqueous $NH_4Cl$. The reaction mixture was extracted with ethyl acetate, dried over $Na_2SO_4$ and concentrated under diminished pressure. Purification by flash column chromatography (silica gel, hexanes/ethyl acetate, 95:5) afforded 40.5 mg (60%) of the desired tertiary alcohol intermediate, along with 14 mg (22%) of unreacted starting material. This intermediate alcohol (14 mg, 0.028 mmol) was dissolved in 1 mL of anhydrous THF containing 60 mL (0.56 mmol, 20.0 equiv) of acetic anhydride, and cooled to 0° C. Tetra-n-butylammonium fluoride (33 mL of a 1.0M solution in THF, 0.033 mmol, 1.20 equiv) was added, and the mixture was allowed to warm to room temperature. The contents of the flask were then poured into a separatory funnel containing 5 mL of ethyl acetate and 2 mL of aqueous 1M $NaHSO_4$. The layers were separated, the organic phase was dried over $Na_2SO_4$, and the solvent was removed under diminished pressure. The crude intermediate (12.4 mg) was placed in a 10 mL Nalgene vial containing 2 mL of dry THF, 0.175 mL of premade HF/pyridine complex was added, and the mixture was allowed to stir at room temperature for 18 h. The contents of the vial were then transferred into a separatory fimel containing 5 mL of ethyl acetate and 3 mL of aqueous 1M $NaHSO_4$. The layers were separated, and the organic phase was washed with 2 mL of brine, dried over $Na_2SO_4$, and concentrated under diminished pressure. Purification by flash column chromatography (silica gel, hexanes/ethyl acetate, 85:15) afforded 6.4 mg (60% for the 2 steps) of the desired acetylated phenol. $^1$H NMR (400 MHz, $CDCl_3$) δ 0.85 (d, 3H, 5-$CH_3$), 1.67 (m, 2H), 1.76 (s, 3H, 3-$CH_3$), 2.20 (dd, 1H), 2.27 (s, 3H, acetate-$CH_3$), 2.49 (m, 3H), 3.86 (s, 3H, $OCH_3$), 4.40 and 4.71 (2s, 2×1H, methylidene-$CH_2$),586 (s, 1H, 3-H), 6.64 (s, 1H, 6'-H), 7.21 ppm (s, 1H, 3'-H). [This compound is also referred to as Compound "Y" or 120260]

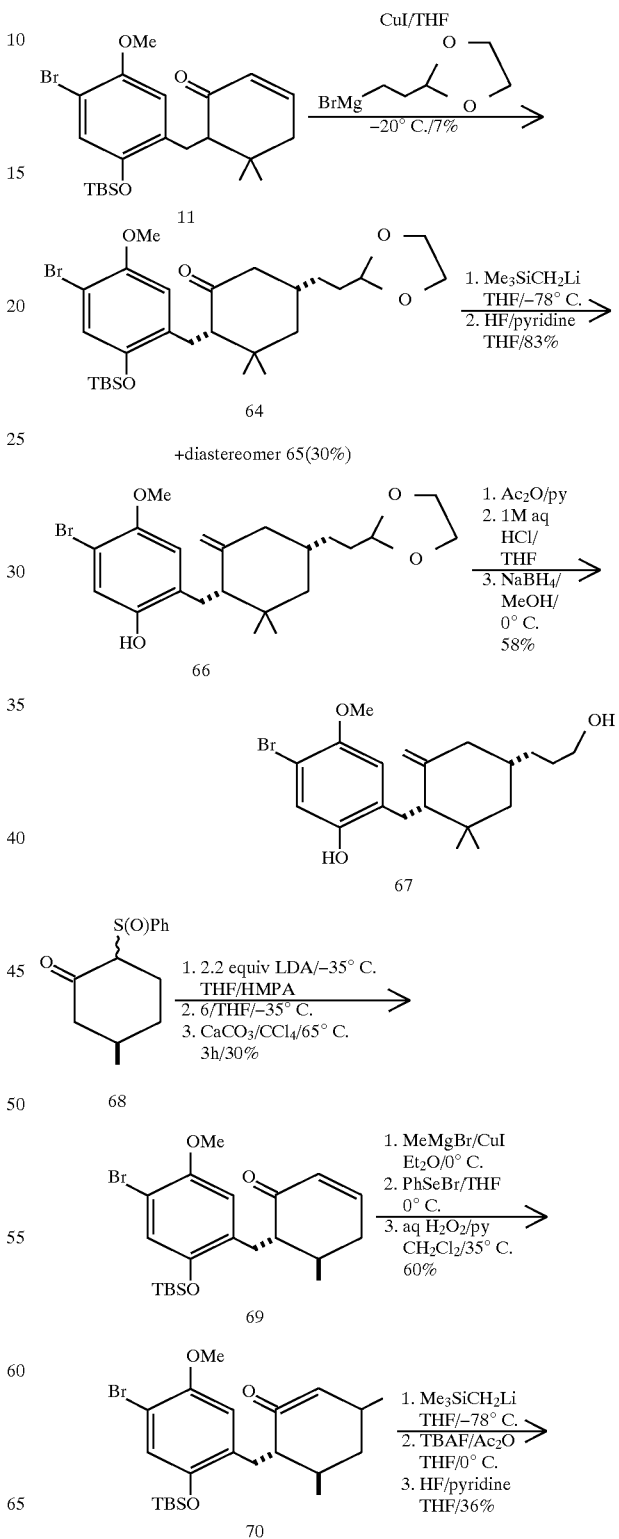

-continued

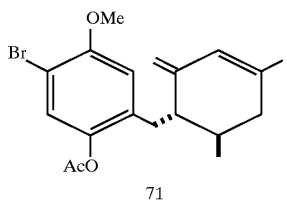

71

EXAMPLE 46
cis-2-[(2'-tert-Butyl)dimethylsilyloxy-4'-bromo-5'-methoxyphenyl]methyl-3,3,5-trimethylcyclohexan-1-one (72)

To a suspension of copper(I) iodide (2 mg) in 1 mL of anhydrous ether at 0° C. was added methylmagnesium bromide (0.106 mL of a 3.0M solution in ether, 0.319 mmol, 1.00 equiv). Then enone (11) (149 mg, 0.319 mmol) in 2 mL of anhydrous ether was added slowly to the stirring cuprate mixture at a temperature maintained below 5° C., and upon completion of the addition, the reaction mixture was stirred at 0° C. for 3 h before quenching with a 4:1 mixture of saturated aqueous $NH_4Cl/NH_4OH$. The resultant biphasic mixture was extracted with ether, dried over $Na_2SO_4$, and concentrated under diminished pressure. Purification by flash column chromatography (silica gel, hexanes/ethyl acetate, 9:1) afforded 36 mg (30%) of the desired conjugate addition product as a white solid. $^1H$ NMR (400 MHz, $CDCl_3$) δ 0.22 (s, 6H, $Si(CH_3)_2$), 1.00 [m, 18H, 3,3,5-$CH_3$ and $SiC(CH_3)_3$], 1.50 (dd, 2H, J=15.1. 6.5 Hz, 4-H), 2.02 (m, 1H, 5-H), 2.14 and 2.23 (ABq, 2H, $J_{AB}$=12.0 Hz, 6-H), 2.42 (dd, 1H, J=10.4, 6.4 Hz, 2-H), 2.88 and 2.89 (d of ABq, 2H, $J_A$=12.0 Hz, $J_A$=10.4 Hz, $J_B$=6.3 Hz, benzylic-$CH_2$), 3.82 (s, 3H, $OCH_3$), 6.65 (s, 1H, 6'-H), 6.92 ppm (s, 1H, 3'-H).

cis-1-Methylidene-2-(2'-hydroxy-4'-bromo-5'-methoxyphenyl)methyl-3,3,5-trimethyleyclohexane (73)

To a solution of cis-2-[(2'-tert-butyl)dimethylsilyloxy-4'-bromo-5'-methoxyphenyl]methyl-3,3,5-trimethylcyclohexan-1-one (72) (7.5 mg, 0.016 mmol, 1.0 equiv) in 1 mL of anhydrous THF at −78° C. was added (trimethyl)silylmethyllithium (66 mL of a 1.0M solution in pentane, 0.066 mmol, 4.0 equiv) and the mixture was stirred for 20 min, at which time tlc analysis indicated complete consumption of starting material, and the reaction was quenched at −78° C. with 1 mL of saturated aqueous $NH_4Cl$. The resulting biphasic mixture was allowed to warm to room temperature and was extracted with ethyl acetate (30 mL), and the organic layer was dried over $Na_2SO_4$, and concentrated under diminished pressure. Purification by flash column chromatography (silica gel, hexanes/ethyl acetate, 4:1) afforded 7.3 mg (86%) of the desired tertiary alcohol intermediate as a colorless oil. Five milligrams of this intermediate were placed in a 10 mL Nalgene vial containing 1 mL of dry THF, 68 mL of HF/pyridine complex were added, and the mixture was allowed to stir at room temperature for 32 h, after which time the contents of the vial were transferred into a separatory fimel containing 3 mL of ethyl acetate and 1 mL of 1M aqueous $NaHSO_4$. The layers were separated, and the organic phase was washed with 1 mL of brine, dried over $Na_2SO_4$, and concentrated under diminished pressure. Purification by flash column chromatography (silica gel, hexanes/ethyl acetate, 9:1) afforded 2.7 mg (81%) of the desired phenol as a colorless, viscous oil. $^1H$ NMR (400 MHz, $CDCl_3$) δ 0.92 and 1.06 (2s, 2×3H, geminal-$CH_3$'s), 0.95 (d, 3H, J=8.0 Hz, 5-$CH_3$), 1.70 (m, 1H), 1.84 (m, 2H), 2.09 (m, 1H), 2.10 (dd, 1H, J=13.3, 4.2 Hz, 2-H), 2.58 and 2.81 (d of ABq, 2H, $J_{AB}$=13.6 Hz, $J_A$=11.2 Hz, $J_B$=3.7 Hz, benzylic-$CH_2$), 3.81 (s, 3H, $OCH_3$), 4.27 and 4.58 (2s, 2×1H, methylidene-$CH_2$), 4.42 (s, 1H, OH), 6.53 (s, 1H, 6'-H), 6.94 ppm (s, 1H, 3'-H). [This compound is also referred to as Compound "BB" or 120275]

EXAMPLE 47
2-[(2'-tert-Butyl-dimethylsilyloxy-4'-bromo-5'-methoxyphenyl]methyl-3,3,5-trimethyl-5-ethenylcyclohexan-1-one (74)

To a flame-dried 50 mL round-bottomed flask containing a solution of 27 mg (0.132 mmol) of copper bromide-dimethylsulfide complex in 1 mL of anhydrous dimethylsulfide and 5 mL of anhydrous THF at −55° C. was added a solution of 6-[2'-(tert-butyl)dimethylsilyloxy-4'-bromo-5'-methoxy-phenyl]methyl-3,5,5-trimethylcyclohex-2-en-1-one (16) (127 mg, 0.264 mmol) in 2 mL of anhydrous THF, and the reaction temperature was maintained at below −50° C. while vinylmagnesium bromide (1.32 mL of a 1.0M solution in THF, 1.32 mmol, 5.0 equiv) was added dropwise over 30 minutes. During this process it was important to immerse the entire reaction flask in the cooling bath so that any vinyl cuprate reagent splashed on the wall of the flask did not undergo thermal decomposition. The reaction mixture was stirred at −50° C. for an additional 30 minutes, and then siphoned into cold, vigorously stirred aqueous 2N HCl. In this procedure it was important to keep the reaction temperature below −40° C. The resulting mixture was extracted with ether, and the organic extract was washed with saturated aqueous $NaHCO_3$, dried over $Na_2SO_4$, and concentrated under diminished pressure. Purification by flash column chromatography (silica gel, hexanes/ethyl acetate 9:1) gave 115 mg (86%) of the desired ketone as a pale yellow oil. $^1H$ NMR (400 MHz, $CDCl_3$) δ 0.21 and 0.25 [2s, 2×3H, $Si(CH_3)_2$], 0.85 and 1.07 (2s, 2×3H, geminal-CH3's), 0.97 [s, 9H, $SiC(CH_3)_3$], 112 (s, 3H), 1.75 (ABq, 2H, 4-H), 2.62 (m, 2H), 2.82 (dd, 2H, J=12.0, 8.8 Hz, benzylic-$CH_2$), 3.82 (s, 3H, $OCH_3$), 4.95 (d, 1H, J=9.6 Hz, CH=CHH), 5.08 (d, 1H, J=16 Hz, CH=CHH), 5.76 (dd, 1H, J=16, 9.6 Hz, CH=CHH), 6.85 (s, 1H, 6'-H), 6.92 ppm (s, 1H, 3'-H).

2-[(2'-tert-Butyl)dimethylsilyloxy-4'-bromo-5'-methoxyphenyl]methy-3,3,5-trimethyl-5-formylcyclohexan-1-one (75)

A 25 mL round-bottomed flask, equipped with a magnetic stirrer, was charged with 4 mL of tert-butyl alcohol, 6 mL of water and 1.13 g of AD-MIX b. The mixture was cooled to 0° C., and olefin (74) in 2 mL of tert-butyl alcohol was added all at once and the heterogeneous slurry was stirred vigourously at room temperature for 84 h. While at 0° C., $Na_2SO_3$ (1.45 g) was added slowly, and the reaction mixture allowed to warm to room temperature, stirring for an additional 45 min. Ethyl acetate (58 mL) was added to the reaction mixture, and after separation of the layers, the aqueous phase was further extracted with ethyl acetate, and the combined organic solutions were dried over $Na_2SO_4$ and concentrated under diminished pressure to give the crude diol as a diastereomeric mixture (422 mg, 96%) that was carried on to the next step without further purification. To a cold (0° C.) solution of the crude diol (30 mg, 0.056 mmol, 1.00 equiv) in absolute ethanol (0.354 mL) was added a solution of $NaIO_4$ (36 mg, 0.167 mmol, 3.00 equiv), and NaOH (1 mg, 0.02 mmol, 0.38 equiv) in 20 mL of water. The reaction mixture was stirred at 0° C. for 30 minutes (during which time a white precipitate formed), and was then partitioned between water (2 mL) and chloroform (2 mL). The layers were separated, and the aqueous phase was extracted with chloroform (2×2 mL). The combined organic fractions were washed with water (3 mL), and dried over Na$_2$SO$_4$. Filtration and removal of the solvent under diminished pressure gave 20 mg of the desired aldehyde that was used directly in the next step. $^1$H NMR (400 MHz, CDCl$_3$) δ 0.22 and 0.26 [2s, 2×3H, Si(CH$_3$)$_2$], 0.69 and 1.16 (2s, 2×3H, geminal-CH$_3$'s), 0.97 [s, 9H, SiC(CH$_3$)$_3$], 2.63 (dd, 1H, 2-H), 2.84 and 2.90 (d of ABq, 2H benzylic-CH$_2$), 3.82 (s, 3H, OCH$_3$), 6.86 (s, 1H, 6'-H), 6.92 (s, 1H, 3'-H), 9.5 ppm (s, 1H, CHO).

2-[(2'-tert-Butyl)dimethylsilyloxy-4'-bromo-5'-methoxyphenol]methyl-3,3,5-trimethyl-5-(hydroxymethyl)cyclohexan-1-one (76)

To a solution of aldehyde (75) (20 mg, 0.041 mmol)in 0.5 mL of anhydrous THF at −78° C. was slowly added lithium [tris[(3-ethyl-3-pentyl)-oxy]aluminohydride (LiTEPA) (82 mL of a 0.5M solution in THF, 0.041 mmol, 1.00 equiv). The reaction was monitored by TLC, and upon completion 0.05 mL of methanol was added, and the reaction mixture was poured into water (1 mL).

The aqueous phase was extracted with ether (3 mL), and the organic layer was washed with water and brine, dried over Na$_2$SO$_4$, and concentrated under diminished pressure. Purification by flash column chromatography (silica gel, hexanes/ethyl acetate 7:3) gave 19 mg (98%) of the desired alcohol as a colorless oil. $^1$H NMR (400 MHz, CDCl$_3$) δ 0.23 and 0.25 [2s, 2×3H, Si(CH$_3$)$_2$], 0.94 and 1.05 (2s, 2×3H, geminal-CH3's), 0.95 [s, 9H, SiC(CH$_3$)$_3$], 1.16 (s, 3H, 5-CH$_3$), 1.36 (t, 1H, OH), 2.70 and 2.86 (d of ABq, 2H, benzylic-CH$_2$), 2.70 (dd, 1H, 2-H), 3.40 (d, 2H, CH$_2$OH), 3.83 (s, 3H, OCH$_3$), 6.80 (s, 1H, 6'-H), 6.92 ppm (s, 1H, 3'-H).

trans-1-Methylidene-2-(2'-hydroxy-4'-bromo-5'-methoxyphenyl)methyl-3,3,5-trimethyl-5-(hydroxymethyl)cyclohexane (77)

To a flame-dried 10 mL round-bottomed flask containing 14.6 mg (0.029 mmol) of 2-[(2'-tert-butyl)dimethylsilyloxy-4'-bromo-5'-methoxyphenyl]methyl-3,3,5-trimethyl-5-(hydroxymethyl)cyclohexan-1-one (76) in 1 mL of dry dichloromethane at room temperature was added imidazole (5.4 mg, 0.08 mmol, 2.80 equiv), tert-butyldimethylchlorosilane (6.4 mg, 0.04 mmol, 1.50 equiv) and DMAP (0.5 mg, catalytic). The mixture was allowed to stir at room temperature for 18 h, at which time TLC analysis indicated complete consumption of starting material, and the formation of a less polar product. The reaction mixture was then poured into a separatory funnel containing 5 mL of dichloromethane and 5 mL saturated aqueous NH$_4$Cl. The layers were separated, and the organic phase was washed with 5 mL of brine, dried over Na$_2$SO$_4$, and concentrated under diminished pressure. To a solution of the silylated alcohol thus obtained (13.5 mg, 0.022 mmol, 1.00 equiv) in 2 mL of anhydrous THF at −78° C. was added (trimethyl)silylmethyllithium (43 mL of a 1.0M solution in pentane, 0.044 mmol, 2.00 equiv). After 20 minutes of stirring at −78° C., the reaction was quenched at −78° C. with 1 mL of saturated aqueous NH$_4$Cl, and extracted with ethyl acetate. The organic phase was dried over Na$_2$SO$_4$ and concentrated under diminished pressure. Purification by flash column chromatography (silica gel, hexanes/ethyl acetate 4:1) gave 14.6 mg (94%) of the desired tertiary alcohol. Fourteen milligrams of this intermediate was placed in a 10 mL Nalgene vial containing 2 mL of dry THF, 0.200 mL of a HF/pyridine complex was added, and the mixture was allowed to stir at room temperature for 36 h. The contents of the vial were transferred into a separatory funnel containing 5 mL of ethyl acetate and 3 mL of 1M aqueous NaHSO$_4$. The layers were separated, and the organic phase was washed with 2 mL of brine, dried over Na$_2$SO$_4$, and concentrated under diminished pressure. Purification by flash column chromatography (silica gel, hexanes/ethyl acetate 9:1) gave 6.67 mg (83%) of the desired olefin as a colorless oil. 1H NMR (400 MHz, CDCl$_3$) δ 0.95, 1.02 and 1.07 (3s, 3×3H, CH$_3$'s), 1.43 (t, 1H, J=4.0 Hz, OH), 2.18 (dd, 1H, J=11.1, 3.6 Hz, 2-H), 2.78 (dd, 1H, J=14.3, 3.9 Hz, benzylic-CH$_2$), 2.64 (dd, 1H, J=14.2, 11.2 Hz, benzylic-CH$_2$), 3.34 (d, 2H, J=4.2 Hz, CH$_2$OH), 3.80 (s, 3H, OCH$_3$), 4.56 and 4.49 (2s, 2×1H, methylidene-CH$_2$), 6.61 (s, 1H, 6'-H), 6.94 ppm (s, 1H, 3'-H). [This compound is also referred to as Compound "HH" or 120345]

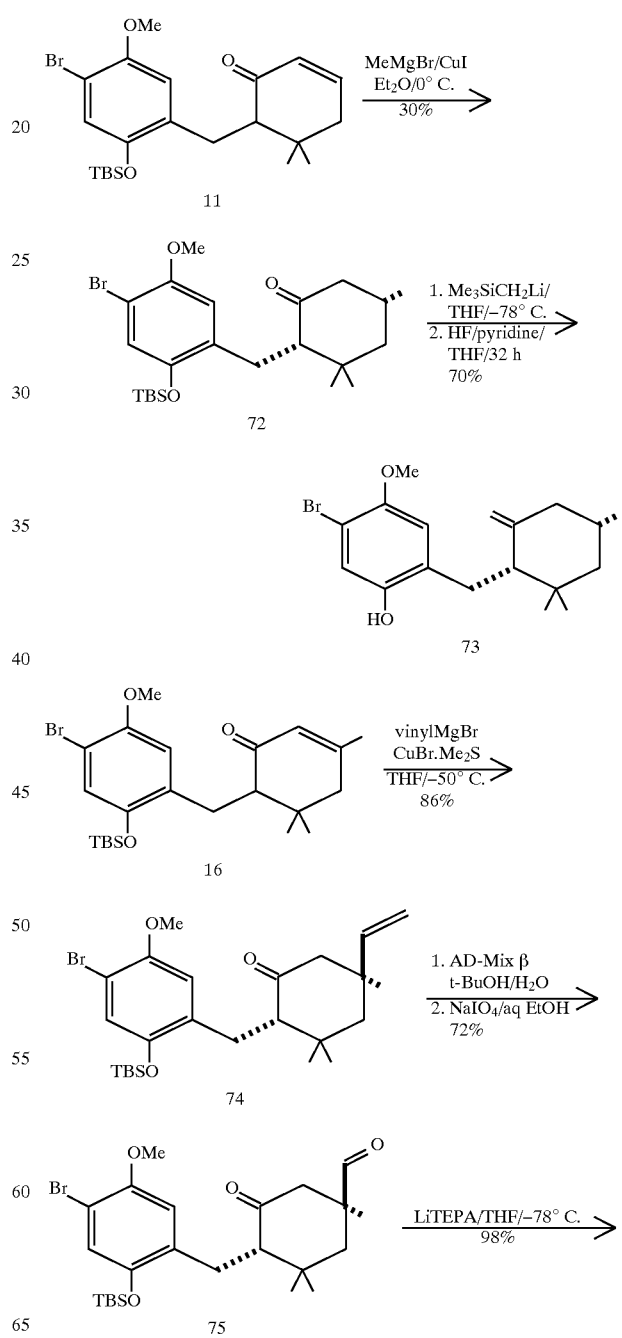

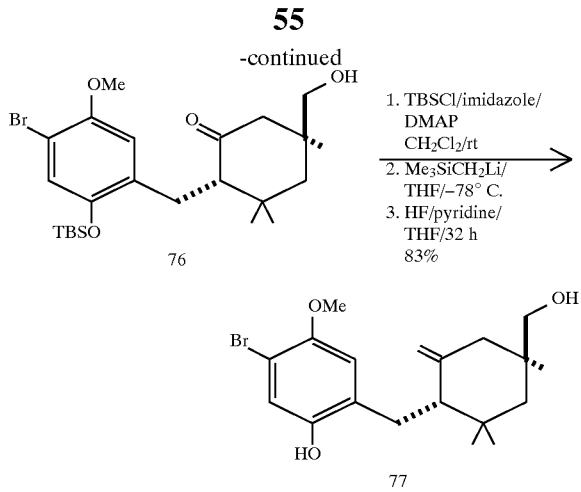

Additional Semisynthetic Derivatives of Natural Cyclocymopols

EXAMPLE 48
(3R)-5-Oxo-1-debromocyclocymopol monomethyl ether, (tert-butyl)dimethylsilyl ether (80)

This exo-enone was prepared in two steps from (3R)-1-debromocyclocymopol monomethyl ether, (tert-butyl)dimethylsilyl ether (78) (0.750 g, 1.66 mmol). The first step (oxidation with selenium (IV) oxide) was carried out in the manner previously described for the synthesis of hydroxycyclocymopol (31), affording 741 mg (95%) of an inseparable 1:1 mixture of diastereomeric allylic alcohols as white solids. The pair of allylic alcohols were carried on to the next step without further purification. To a flame dried 50 mL round-bottomed flask containing a 1:1 mixture of silyl-protected phenols (79) (345 mg, 0.736 mmol) in 25 mL dichloromethane with 2% pyridine at room temperature was added Dess-Martin periodinane reagent (330 mg, 0.772 mmol, 1.05 equiv), and the mixture was stirred for 5 min. The reaction mixture was then transferred to a 125 mL erlynmeyer flask containing 50 mL 1:1 saturated aqueous NaHCO$_3$/10% Na$_2$S$_2$O$_3$, and the mixture was stirred for an additional 90 min. The mixture was then extracted with dichloromethane (2×40 mL), and the organic phase was washed with brine, dried over Na$_2$SO$_4$, and concentrated under diminished pressure. Purification by flash column chromatography (silica gel, hexanes/ethyl acetate, 9:1) afforded 289 mg (85%) of the desired enone as a white solid. $^1$H NMR (400 MHz, CDCl$_3$) δ 0.23 [(s, 6H, Si(CH$_3$)$_2$], 1.00 [s, 9H, SiC(CH$_3$)$_3$], 1.12 and 1.15 (2s, 2×3H, geminal-CH$_3$'s), 1.62 (dddd, 1H, J=9.9, 6.6, 5.4, 1.3 Hz, 1-H$_{eq}$), 2.01 (dddd, 1H, J=14.0, 13.8, 8.9, 2.3 Hz, 1-H$_{ax}$), 2.24 and 2.50 (d of ABq, 2H, J$_{AB}$=11.9 Hz, J$_A$=11.9 Hz, J$_B$=2.8 Hz, benzylic-CH$_2$), 2.46 and 2.48 (ABq, 2H, J$_{AB}$=5.4 Hz, 6-H), 3.07 (dd, 1H, J=13.3, 3.6 Hz, 3-H), 3.80 (s, 3H, OCH$_3$), 4.46 (d, 1H, J=1.6 Hz) and 5.54 (d, 1H, J=1.8 Hz) [methylidene-CH$_2$], 6.41 (s, 1H, 6'-H), 6.93 ppm (s, 1H, 3'-H).

(3R,5S-5-Hydroxy-5-methyl-1-debromocyclocymopol monomethyl ether (81) and (3R,5R)-5-Hydroxy-5-methyl-1-debromocyclocymopol monomethyl ether (82)

To a flame-dried 25 mL round-bottomed flask containing a solution of (3R)-5-oxo-1-debromocyclocymopol monomethyl ether, (tert-butyl)dimethylsilyl ether (80) (28.0 mg, 0.060 mmol) in 6 mL THF at −70° C. under nitrogen atmosphere was added methyllithium (120 mL of a 1.40M solution in ether, 0.168 mmol, 2.80 equiv), and the mixture was allowed to stir for 5 min before quenching with saturated aqueous NH$_4$Cl. Upon warming to room temperature, the reaction mixture was extracted with ethyl acetate, and the organic phase was washed with brine, dried over Na$_2$SO$_4$, and concentrated under diminished pressure gave a 3:1 (3R,5S:3R,5R) mixture of the diastereomeric tertiary hydroxyls. Purification by flash column chromatography (silica gel, hexanes/ethyl acetate, gradient elution) afforded 6.9 mg (24%) of the less polar, minor 3R,5R isomer (82), along with 20.6 mg (71%) of the more polar, major 3R,5S isomer (81). Data for 81 $^1$H NMR (400 MHz, CDCl$_3$) δ 0.21 and 0.23 (s, 6H, Si(CH$_3$)$_2$], 0.84 [s, 9H, SiC(CH$_3$)$_3$], 0.84 and 1.04 (2s, 2×CH$_3$'s), 1.39 (s, 3H, 5-CH$_3$), 2.43 (br dd, 1H, J__11.3, 2.9 Hz, 3-H), 2.72 and 2.85 (d of ABq, 2H, J$_{AB}$=16.1 Hz, J$_A$=3.1 Hz, J$_B$=11.5 Hz, benzylic-CH$_2$) 3.77 (s, 3H, OCH$_3$), 4.57 and 5.16 (2s, 2×1H, methylidene-CH$_2$), 6.63 (s, 1H, 6'-H), 6.93 ppm (s, 1H, 3'-H); Data for 82 $^1$H NMR (400 MHz, CDCl$_3$) δ 0.19 and 0.24 (s, 6H, Si(CH$_3$)$_2$], 0.77 and 1.08 (2s, 2×3H, geminal-CH$_3$'s), 1.0 [s,9H, SiC(CH$_3$)$_3$], 1.36 (s, 3H, 5-CH$_3$), 2.65 and 2.82 (d of ABq, 2H, J$_{AB}$=16.0 Hz, J$_A$=3.0 Hz, J$_B$=11.8 Hz, benzylic-CH$_2$), 2.97 (br dd, 1H, J__11.7, 2.5 Hz, 3-H), 3.79 (s, 3H, OCH$_3$), 4.64 and 4.96 (2s, 2×1H, methylidene-CH$_2$), 6.73 (s, 1H, 6'-H), 6.92 ppm (s, 1H, 3'-H).

(3R)-5-Methyl-5,6-dehydro-1-debromocyclocymopol monomethyl ether, acetate (83)

To a flame-dried 10 mL round-bottomed flask containing the 3:1 diastereomeric mixture of tertiary alcohols (81) and (82) (3.0 mg, 0.006 mmol) in 1 mL anhydrous benzene at room temperature was added Burgess reagent [(methoxycarbonylsulfamoyl)triethylammonium hydroxide, inner salt] (4.2 mg, 0.018 mmol, 2.5 equiv), and the mixture was allowed to stir for 12 h. Removal of the solvent under diminished pressure gave the crude diene, which was subjected to the standard conditions for deprotection of the silyl ether, trapping the intermediate phenoxide as the acetate (TBAF, THF, Ac$_2$O, 0° C.). Purification by flash column chromatography (silica gel, hexanes/ethyl acetate, gradient elution) afforded 4.8 mg (74%) of the desired diene as a colorless oil. $^1$H NMR (400 MHz, CDCl$_3$) δ 0.87 and 1.09 (2s, 2×3H, gerninal-CH$_3$'s), 1.81 (s, 3H, 5-CH$_3$), 2.26 (s, 3H, acetate-CH$_3$), 2.77 (dd, 1H, J=12.8, 3.1 Hz, benzylic-H), 3.83 (s, 3H, OCH$_3$), 4.13 and 4.75 (2s, 2×1H, methylidene-CH$_2$), 5.53 (br s, 1H, 3-H), 6.45 (s, 1H, 6'-H), 7.18 ppm (s, 1H, 3'-H). [This compound is also referred to as Compound "Z" or 120262]

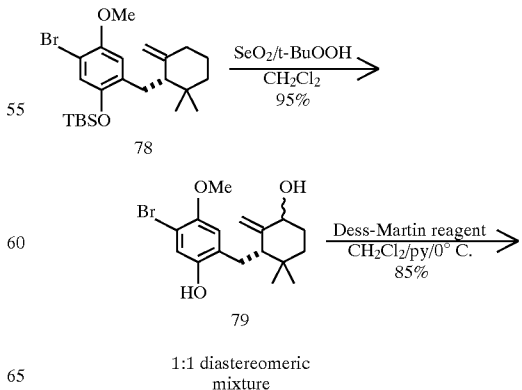

1:1 diastereomeric mixture

-continued

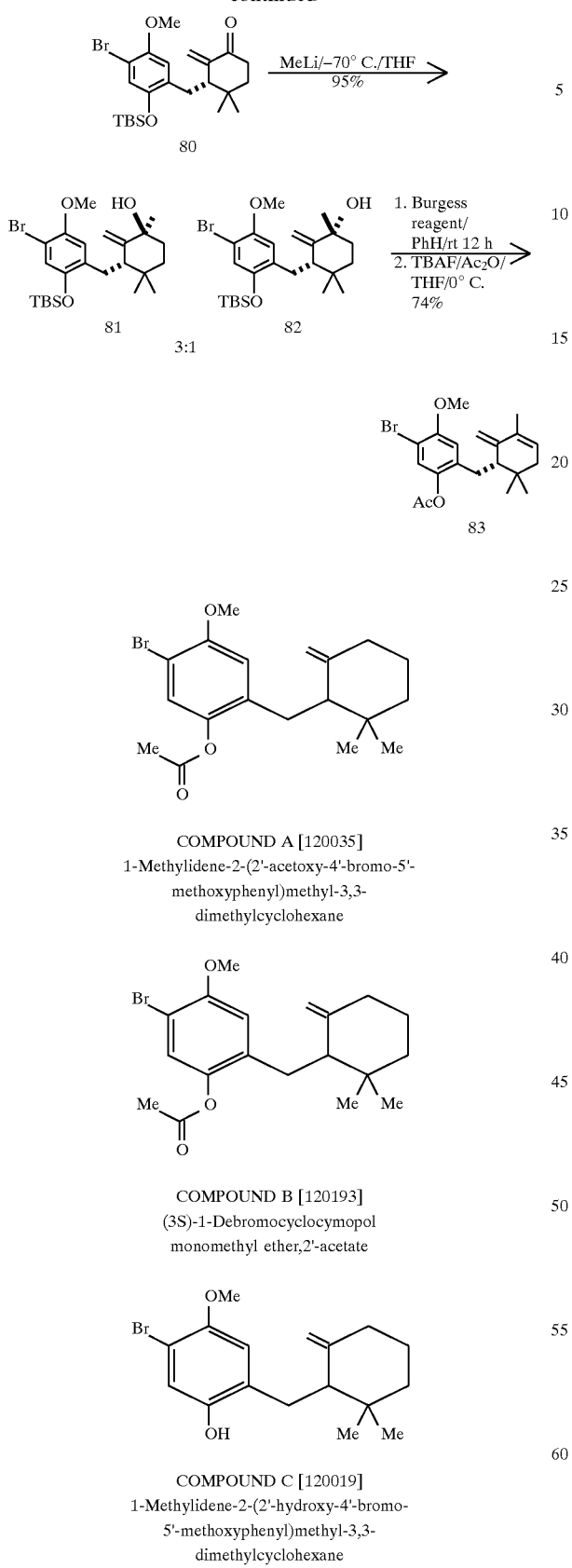

COMPOUND A [120035]
1-Methylidene-2-(2'-acetoxy-4'-bromo-5'-methoxyphenyl)methyl-3,3-dimethylcyclohexane COMPOUND B [120193]
(3S)-1-Debromocyclocymopol monomethyl ether,2'-acetate COMPOUND C [120019]
1-Methylidene-2-(2'-hydroxy-4'-bromo-5'-methoxyphenyl)methyl-3,3-dimethylcyclohexane -continued

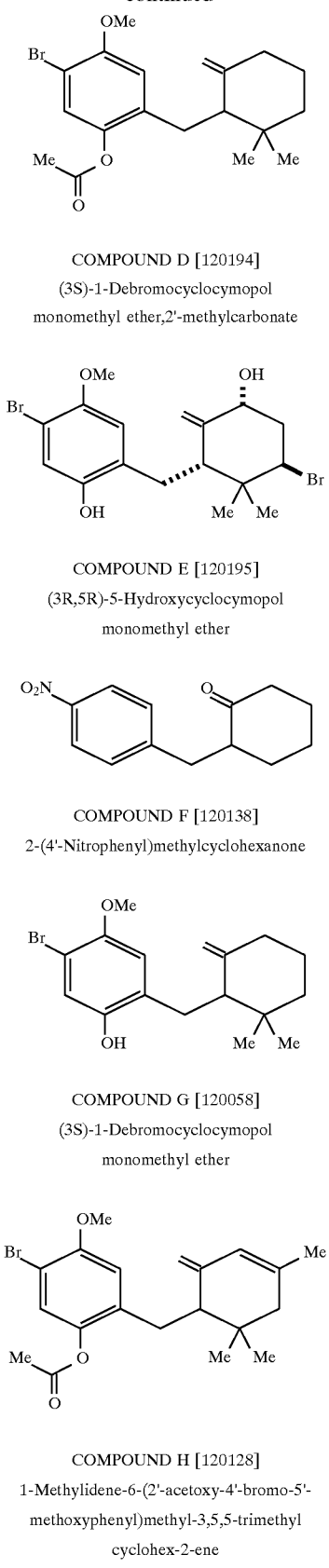

COMPOUND D [120194]
(3S)-1-Debromocyclocymopol monomethyl ether,2'-methylcarbonate COMPOUND E [120195]
(3R,5R)-5-Hydroxycyclocymopol monomethyl ether COMPOUND F [120138]
2-(4'-Nitrophenyl)methylcyclohexanone COMPOUND G [120058]
(3S)-1-Debromocyclocymopol monomethyl ether COMPOUND H [120128]
1-Methylidene-6-(2'-acetoxy-4'-bromo-5'-methoxyphenyl)methyl-3,5,5-trimethyl cyclohex-2-ene -continued

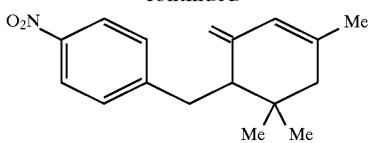

COMPOUND I [120190]
1-Methylidene-6-(4'-nitrophenyl)methyl-
3,5,5-trimethylcyclohex-2-ene

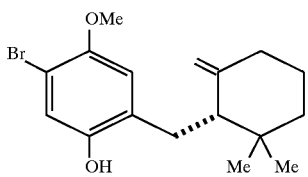

COMPOUND J [120037]
(3R)-1-Debromocyclocymopol
monomethyl ether

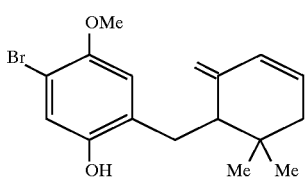

COMPOUND K [120033]
1-Methylidene-6-(2'-hydroxy-4'-bromo-
5'-methoxyphenyl)methyl-5,5-
dimethylcyclohex-2-ene

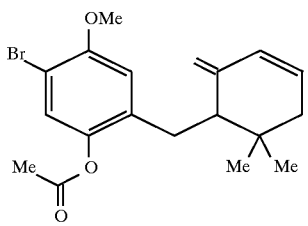

COMPOUND L [120032]
1-Methylidene-6-(2'-acetoxy-4'-bromo-5'-
methoxyphenyl)methyl-5,5-
dimethylcyclohex-2-ene

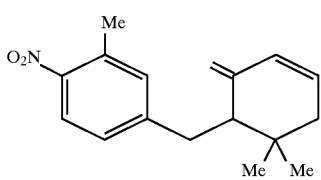

COMPOUND M [120120]
1-Methylidene-6-(3'-methyl-4'-
nitrophenyl)methyl-5,5-
dimethylcyclohex-2-ene -continued

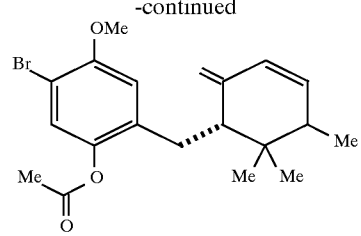

COMPOUND N [120049]
trans-1-Methylidene-6-(2'-acetoxy-4'-
bromo-5'-methoxyphenyl)methyl-4,5,5-
trimethylcyclohex-2-ene

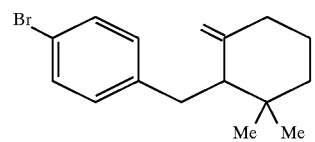

COMPOUND O [120130]
1-Methylidene-2-(4'-bromophenyl)
methyl-3,3-dimethylcyclohexane

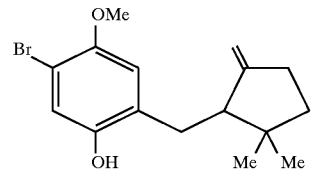

COMPOUND P [120192]
1-Methylidene-2-(2'-hydroxy-4'-bromo-
5'-methoxyphenyl)methyl-3,3-dimethyl
cyclopentane

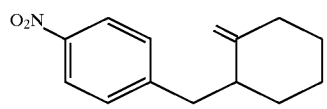

COMPOUND Q [120194]
1-Methylidene-2-(4'-nitrophenyl)
methylcyclohexane

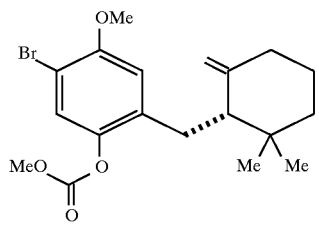

COMPOUND R [120057]
(3R)-1-Debromocyclocymopol
monomethyl ether,2'-methylcarbonate

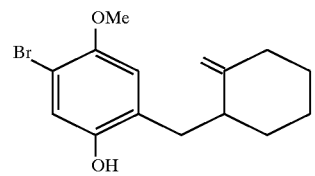

COMPOUND S [120089]
1-Methylidene-2-(2'-hydroxy-4'-bromo-
5'-methoxyphenyl)methylcyclohexane

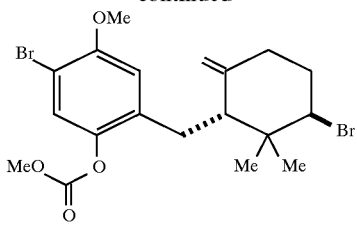

COMPOUND T [120011]
(3R)-Cyclocymopol monomethyl ether,2'-methylcarbonate

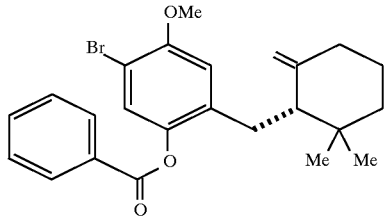

COMPOUND U [120198]
(3R)-1-Debromocyclocymopol monomethyl ether,2'-benzoate

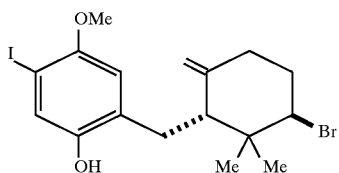

COMPOUND V [120111]
(3R)-4'-Iodocyclocymopol monomethyl ether

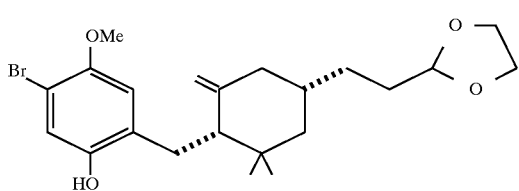

COMPOUND W [120241]
cis-1-Methylidene-2-(2'-hydroxy-4'-bromo-5'-methoxyphenyl)methyl-3,3-dimethyl-5-(propanal-1,3-dioxolane)cyclohexane

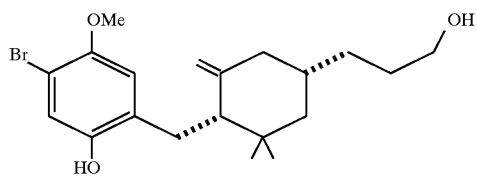

COMPOUND X [120257]
cis-1-Methylidene-2-(2'-hydroxy-4'-bromo-5'-methoxyphenyl)methyl-3,3-dimethyl-5-(3-hydroxypropyl)cyclohexane

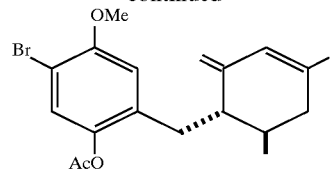

COMPOUND Y [120260]
(5R,6S)-1-Methylidene-6-(2'-acetoxy-4'-bromo-5'-methoxyphenyl)methyl-5-methyl-cyclohex-2-ene

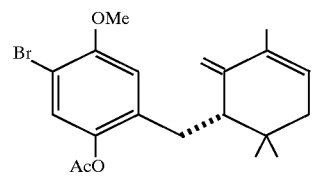

COMPOUND Z [120262]
(3R)-5-Methyl-5,6-dehydro-1-debromocyclocymopol monomethyl ether,acetate

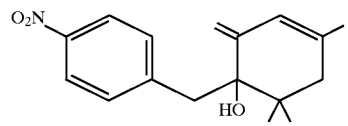

COMPOUND AA [120269]
1-Hydroxy-1-(4'-nitrophenyl)methyl-2-methylidene-4,6,6-trimethylcyclohex-3-ene

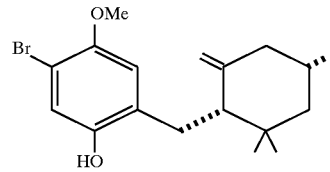

COMPOUND BB [120275]
cis-1-Methylidene-2-(2'-hydroxy-4'-bromo-5'-methoxyphenyl)methyl-3,3,5-trimethyl-cclohexane

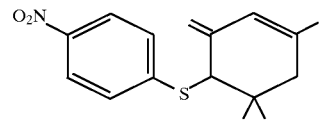

COMPOUND CC [120280]
1-Methylidene-6-(4'-nitrophenyl)thio-3,5,5-trimethylcyclohex-2-ene

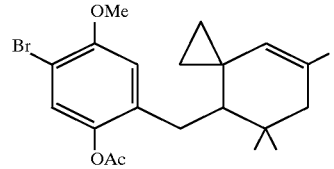

COMPOUND DD [120299]
8-(2'-Acetoxy-4'-bromo-5'-methoxyphenyl)methyl-5,7,7-trimethyl spiro[2.5]oct-4-ene -continued

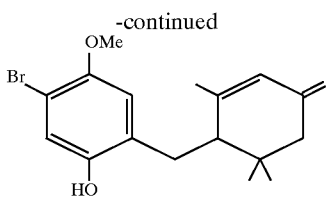

COMPOUND EE [120303]
1-Methylidene-4-(2'-hydroxy-4'-bromo-
5'-methoxyphenyl)methyl-3,5,5-trimethyl
cyclohex-2-ene

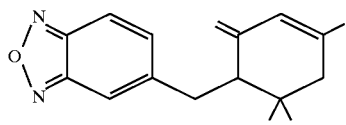

COMPOUND FF [120321]
1-Methylidene-6-(benzofurazan-5'-yl)
methyl-3,5,5-trimethylcyclohex-2-ene

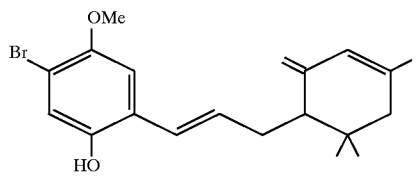

COMPOUND GG [120331]
1-Methylidene-6-[trans-(2'-Hydroxy-4'-
bromo-5'-methoxyphenyl)-1-propenyl]-
3,5,5-trimethylcyclohex-2-ene

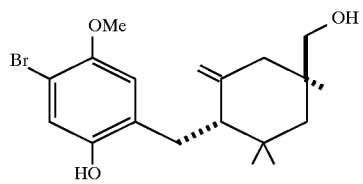

COMPOUND HH [120345]
trans-1-Methylidene-2-(2'-hydroxy-4'
bromo-5'-methoxyphenyl)methyl-3,3,5-
trimethyl-5-(hydroxymethyl)cyclohexane

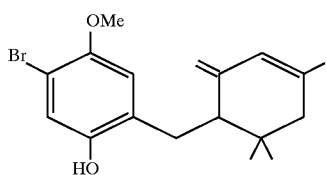

COMPOUND II [120048]
1-Methylidene-6-(2'-hydroxy-4'-bromo-
5'-methoxyphenyl)methyl-3,5,5-
trimethylcyclohex-2-ene

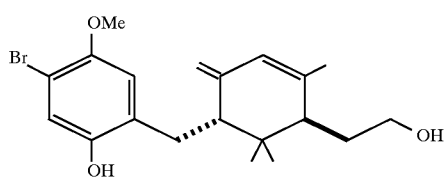

COMPOUND JJ [120382]
trans-1-Methylidene-4-(2'-hydroxy)ethyl-
6-(2"-hydroxy-4"-bromo-5"-methoxy
phenyl)methyl-3,5,5-trimethylcyclohex-2-ene -continued

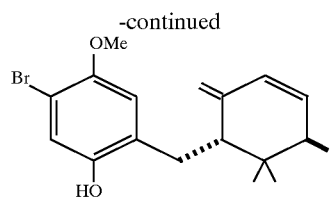

COMPOUND KK [120050]
trans-1-Methylidene-6-(2'-hydroxy-4'-
bromo-5'-methoxyphenyl)methyl-4,5,5-
trimethylcyclohex-2-ene

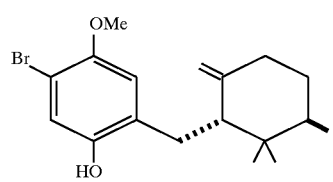

COMPOUND LL [120034]
trans-1-Methylidene-2-(2'-hydroxy-4'-
bromo-5'-methoxyphenyl)methyl-3,3,4-
trimethyl cyclohexane

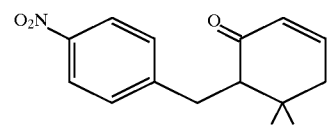

COMPOUND MM [120025]
6-(4'-Nitrophenyl)methyl-5,5-
dimethylcyclohex-2-en-1-one

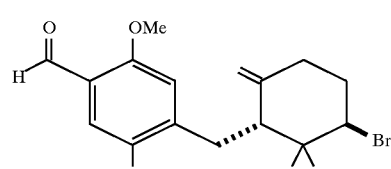

COMPOUND NN [120063]
(3R)-4'-Formylcyclocymopol monomethyl
ether

Utilizing the "co-transfection" assay described above, representative synthetic and semisynthetic cyclocymopol derivatives have been tested and found to be antagonists specifically for the intracellular receptor for progesterone. Cultured monkey kidney cells (CV-1's) were transfected with the human receptor cDNA for the progesterone receptor altered at the Tau-1 location and utilized in the co-transfection assay. The assay was also run using T47D (human breast cancer) cells. The antagonist activity assay results are shown below in Table 1. Table 2 presents comparable results for the antagonists RU-486 and (3R)-cyclocymopol monomethyl ether, and for the agonist (3S)-cyclocymopol monomethyl ether. Efficacy is reported as the % maximal response observed for each compound relative to RU-486, a compound known to exhibit progesterone receptor antagonist activity. Also reported in Tables 1 and 2 for each compound is its potency or $IC_{50}$ (which is the concentration (nM), required to reduce the maximal response by 50%), and its binding activity for the progesterone receptor.

TABLE 1

| Compound | CV-1 Cells Efficacy % | CV-1 Cells Potency nM | T47D Cells Efficacy % | T47D Cells Potency nM | Binding Kd, nM |
|---|---|---|---|---|---|
| A | 55 | 225 | 70 | 200 | 100 |
| B | 45 | 400 | 65 | 85 | 35 |
| C | 55 | 400 | 70 | 200 | 85 |
| D | 45 | 450 | 55 | 150 | 50 |
| E | 85 | 450 | 85 | 475 | 925 |
| F | 100 | 550 | 80 | 200 | 925 |
| G | 45 | 600 | 50 | 300 | 30 |
| H | 40 | 700 | 60 | 775 | 60 |
| I | 95 | 700 | 75 | 125 | 55 |
| J | 95 | 750 | 85 | 175 | 255 |
| K | 70 | 775 | 70 | 275 | 155 |
| L | 55 | 825 | 75 | 200 | 90 |
| M | 90 | 875 | 80 | 350 | 75 |
| N | 90 | 1000 | 70 | 325 | 195 |
| O | 90 | 1000 | 85 | 850 | 445 |
| P | 100 | 1200 | 60 | 275 | 440 |
| Q | 95 | 1200 | 65 | 225 | 245 |
| R | 95 | 1225 | 85 | 250 | 230 |
| S | 90 | 1500 | 85 | 400 | 345 |
| T | 90 | 1575 | 90 | 300 | 185 |
| U | 95 | 1600 | 80 | 300 | 190 |
| V | 95 | 1800 | 85 | 325 | 95 |
| W | 85 | 2900 | 85 | 380 | 362 |
| X | 99 | 1100 | 84 | 210 | 384 |
| Y | 95 | 960 | 77 | 230 | 338 |
| Z | 83 | 660 | 81 | 210 | 455 |
| AA | 87 | 260 | 81 | 94 | 243 |
| BB | 38 | 5140 | 41 | 7190 | 28 |
| CC | 44 | 1350 | 89 | 420 | 119 |
| DD | 26 | 160 | 68 | 440 | 104 |
| EE | 66 | 580 | 75 | 1300 | 109 |
| FF | 72 | 1950 | 71 | 775 | 88 |
| GG | 61 | 3300 | 65 | 1600 | 84 |
| HH | 85 | 3000 | 81 | 1100 | 2310 |
| II | 37 | 3568 | 26 | 1200 | 31 |
| JJ | 48 | 30 | 74 | 3600 | 625 |
| KK | 75 | 1600 | 76 | 1300 | 346 |
| LL | 91 | 1600 | 74 | 500 | 269 |
| MM | 74 | 1767 | 90 | 390 | 10000 |
| NN | 31 | 2100 | 83 | 1800 | 409 |

TABLE 2

| Compound | CV-1 Cells Efficacy % | CV-1 Cells Potency nM | T47D Cells Efficacy % | T47D Cells Potency nM | Binding Kd, nM |
|---|---|---|---|---|---|
| RU-486 | 100 | 0.1 | — | — | 0.6 |
| (3)-cyclocymopol monomethyl ether | 85 | 965 | 85 | 385 | 450 |
| (3)-cyclocympol monomethyl ether | <20 | >10,000 | — | — | 325 |

The synthetic cyclocymopol compounds were also individually tested for cross-reactivity with the other known intracellular receptor classes. This testing showed the compounds not to have activity with the glucocorticoid receptor, in contrast to RU-486 which shows significant activity for that receptor. Some derivative compounds were found to exhibit slight activity for the androgen receptor.

EXAMPLE 49
Decidualization Assay

A successful pregnancy requires not only the effective collision and fusion of egg and spermatozoon, but also the provision of a receptive and supportive uterus. The preparation of the endometrium of the uterus for implantation (i.e. decidualization) starts well before the blastocyst arrives in the uterus. Since decidualization of the rodent uterus is a classic response to progesterone action, a progesterone antagonist should inhibit or interrupt this process when given in vivo.

Psuedopregnant mice (i.e. mated with vasectomized males) were used to establish the assay system. In this regard, the key element of this assay model targets the manipulation of the endocrine status of the mice during the early days of pseudopregnancy by perturbing the action of endogenous progesterone, and thereby blocking the deciduasl cell response. This was achieved by intraluminal administration of various known progesterone antagonists and compounds of the present invention between Day 2 and Day 4 of pseudopregnancy. At 16 hours of Day 4, a small volume of sesame oil (10 $\mu$l) was introduced to the lumen of the right uterine horn to serve as a decidual stimulus. The left horn was left undisturbed to serve as an internal control. Autopsies were performed on Day 7 to assess uterine wet weight gains in the stimulated versus non-stimulated uterine horns.

In addition to control mice, in which no progesterone antagonist was administered, two commercially available anti-progestins, RU-486 (Roussel) and ZK299 (Schering), along with Compound "J" [120037] and Compound "I" [120190] were tested in the assay system. Each of these compounds was intraluminally administered in an appropriate dosage on Day 4 along with the sesame oil administration. The results of the decidualization assay are shown in Table 3 below.

TABLE 3

Effects of anti-progesterone treatment on oil-induced uterine weight gain (mg).

| Compound | Dose | No. of Mice | Net Uterine Weight Gain |
|---|---|---|---|
| "I" | 5 mg | 6 | 63.9 +/− 20.9 |
| "J" | 5 mg | 5 | 30.7 +/− 16.2 |
| ZK299 | 0.1 mg | 6 | 41.1 +/− 21.0 |
| RU-486 | 0.1 mg | 6 | 9.53 +/− 3.51 |
| Oil Alone (Control) | — | 10 | 334.7 +/− 41.0 |

During Day 3 and Day 4 of early pregnancy/psuedopregnancy, there is a steep increase in progesterone concentrations in mice. The level of progesterone continues to rise until it peaks at Day 6. In this regard, as can be seen above, the oil-stimulated (Control) uterine horns display a dramatic increase in net wet weight gain relative to the non-stimulated uterine horns. Treatment with the anti-progestin RU-486 completely blocked this decidualization weight gain, whereas ZK299 treatment gave approximately 88% inhibition. Further, Compounds "I" and "J" of the present invention gave approximately 81% and 91% inhibition respectively.

Pharmacological and Other Applications

It has been recognized that the co-transfection assay provides a functional assessment of the ligand being tested as either an agonist or antagonist of the specific genetic process sought to be affected, and mimics an Ln vivo system in the laboratory. Ligands which do not react with other intracellular receptors, as determined by the co-transfection assay, can be expected to result in fewer pharmacological side effects. Because the co-transfection assay is conducted in living cells, the evaluation of a ligand provides an early indicator of the potential toxicity of the candidate ligand at concentrations where a therapeutic benefit would be expected.

As will be discernible to those skilled in the art, the non-steroid progesterone receptor antagonist and agonist compounds disclosed can be readily utilized in pharmacological applications where progesterone receptor antagonist or agonist activity is desired, and where it is desired to minimize cross reactivities with other related intracellular receptors. In vivo applications of the invention include administration of the disclosed compounds to mammalian subjects, and in particular to humans.

The compounds of the present invention are small molecules which are relatively fat soluble or lipophilic and enter the cell by passive diffusion across the plasma membrane. Consequently, these ligands are well suited for administration orally as well as by injection. Upon administration, these ligands can selectively activate progesterone receptors and thereby modulate processes mediated by these receptors.

The pharmaceutical compositions of this invention are prepared in conventional dosage unit forms by incorporating an active compound of the invention, or a mixture of such compounds, with a nontoxic pharmaceutical carrier according to accepted procedures in a nontoxic amount sufficient to produce the desired pharmacodynamic activity in a mammalian and in particular a human subject. Preferably, the composition contains the active ingredient in an active, but nontoxic, amount selected from about 5 mg to about 500 mg of active ingredient per dosage unit. This quantity depends on the specific biological activity desired and the condition of the patient.

The pharmaceutical carrier or vehicle employed may be, for example, a solid or liquid. A variety of pharmaceutical forms can be employed. Thus, when using a solid carrier, the preparation can be plain milled micronized in oil, tableted, placed in a hard gelatin or enteric-coated capsule in micronized powder or pellet form, or in the form of a troche, lozenge, or suppository. When using a liquid carrier, the preparation can be in the form of a liquid, such as an ampule, or as an aqueous or nonaqueous liquid suspension. The following examples provide illustrative pharmacological composition formulations:

EXAMPLE 50

Hard gelatin capsules are prepared using the following ingredients:

|  | Quantity (mg/capsule) |
| --- | --- |
| (3R)-cyclocymopol monomethyl ether | 140 |
| Starch, dried | 100 |
| Magnesium stearate | 10 |
| Total | 250 mg |

The above ingredients are mixed and filled into hard gelatin capsules in 250 mg quantities.

EXAMPLE 51

|  | Quantity (mg/tablet) |
| --- | --- |
| (3R)-cyclocymopol monomethyl ether | 140 |
| Cellulose, microcrystalline | 200 |
| Silicon dioxide, fumed | 10 |
| Stearic acid | 10 |
| Total | 360 mg |

The components are blended and compressed to form tablets each weighing 665 mg.

EXAMPLE 52

Tablets, each containing 60 mg of active ingredient, are made as follows:

|  | Quantity (mg/tablet) |
| --- | --- |
| (3R)-cyclocymopol monomethyl ether | 60 |
| Starch | 45 |
| Cellulose, microcrystalline | 35 |
| Polyvinylpyrrolidone (PVP) (as 10% solution in water) | 4 |
| Sodium carboxymethyl starch (SCMS) | 4.5 |
| Magnesium stearate | 0.5 |
| Talc | 1.0 |
| Total | 150 mg |

The active ingredient, starch, and cellulose are passed through a No. 45 mesh U.S. sieve and mixed thoroughly. The solution of PVP is mixed with the resultant powders, which are then passed through a No. 14 mesh U.S. sieve. The granules so produced are dried at 50° C. and passed through a No. 18 mesh U.S. sieve. The SCMS, magnesium stearate, and talc, previously passed through a No. 60 mesh U.S. sieve, and then added to the granules which, after mixing, are compressed on a tablet machine to yield tablets each weighing 150 mg.

EXAMPLE 53

Suppositories, each containing 225 mg of active ingredient, may be made as follows:

| (3R)-cyclocymopol monomethyl ether | 225 mg |
| --- | --- |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of normal 2 g capacity and allowed to cool.

EXAMPLE 54

An intravenous formulation may be prepared as follows:

| (3R)-cyclocymopol monomethyl ether | 100 mg |
| --- | --- |
| Isotonic saline | 1,000 ml |
| Glycerol | 100 ml |

The compound is dissolved in the glycerol and then the solution is slowly diluted with isotonic saline. The solution of the above ingredients is then administered intravenously at a rate of 1 ml per minute to a patient.

The compounds of this invention also have utility when labeled as ligands for use in assays to determine the presence of progesterone receptors. They are particularly useful due to their ability to selectively activate progesterone receptors, and can therefore be used to determine the presence of such receptors in the presence of other related receptors.

Due to the selective specificity of the compounds of this invention for progesterone receptors, these compounds can be used to purify samples of progesterone receptors in vitro. Such purification can be carried out by mixing samples containing progesterone receptors with one or more of the cyclocymopol and derivative compounds disclosed so that the compound (ligand) binds to the receptor, and then separating out the bound ligand/receptor combination by separation techniques which are known to those of skill in the art. These techniques include column separation, filtration, centrifugation, tagging and physical separation, and antibody complexing, among others.

While the preferred embodiments have been described and illustrated, various substitutions and modifications may be made thereto without departing from the scope of the invention. Accordingly, it is to be understood that the present invention has been described by way of illustration and not limitation.

We claim:

1. A compound having the formulae:

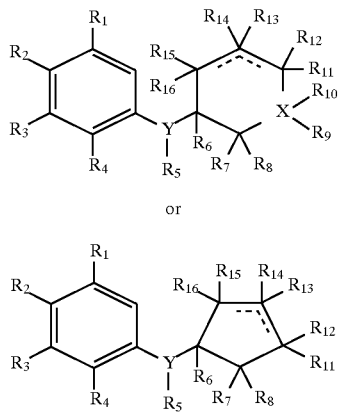

or wherein:
the dotted lines in the structure depict optional double bonds;
X is carbon, oxygen, or nitrogen;
Y is oxygen, nitrogen, sulfur or a saturated or unsaturated $C_1$–$C_4$ alkyl, optionally substituted with oxygen, nitrogen or sulfur;
$R_1$ is $R_{17}$, —$OR_{17}$, —$N(R_{17})(R_{17'})$, —$SR_{17}$, fluorine, chlorine, bromine, or —$NO_2$;
$R_{17}$ and $(R_{17'})$, each independently, are hydrogen, saturated or unsaturated $C_1$–$C_6$ alkyl, $C_3$–$C_7$ cycloalkyl, $C_5$–$C_7$ aryl, or $C_7$ aralkyl, said alkyl groups being branched or straight-chain;
$R_2$ is —$NO_2$, —$N(OH)R_{17}$, fluorine, chlorine, bromine, iodine, $R_{17}$, —$N(R_{17})(R_{17'})$, —$SR_{17}$, —$S(O)$—$R_{17}$, —$S(O)_2$—$R_{17}$, —$CH_2OH$, —$C(O)$—$H$, —$C(O)CH_3$, —$C(O)$—$OCH_3$, —$CH$=$CH_2$, —$C$=$CHC(O)CH_3$, or $R_{18}$;
$R_{18}$ and $(R_{18'})$, each independently, are hydrogen, a saturated or unsaturated $C_1$–$C_6$ alkyl, $C_3$–$C_7$ cycloalkyl, $C_5$–$C_7$ aryl, or $C_7$ aralkyl, said alkyl groups being branched or straight-chain which optionally may contain hydroxyl, aldehyde, ketone, nitrile, or ester groups;
$R_3$ is $R_{17}$ or —$OR_{17}$, or $R_2$ and $R_3$ taken together can form a saturated or unsaturated heterocyclic 3–8 member ring substituted with one or more heteroatoms selected from the group consisting of oxygen, nitrogen, and sulfur, provided, however, that when $R_2$ and $R_3$ form such a saturated or unsaturated heterocyclic 3–8 member ring, then the bond between the carbon atoms carrying the $R_2$ and $R_3$ substituents can be either a single bond or a double bond;

$R_4$ is hydrogen, —$OR_{17}$, —$OC(O)R_{17}$, —$OC(O)OR_{17}$, —$OC(O)N(R_{17})(R_{17'})$, —$OS(O)_2R_{17}$, or —$OS(O)$—$R_{17}$, except that $R_1$, $R_2$, $R_3$, and $R_4$ cannot all be hydrogen, and $R_1$ cannot be $OCH_3$ when $R_2$, $R_3$, and $R_4$ are each hydrogen;

$R_5$ is hydrogen or $OR_{17}$;

$R_6$ is $R_{17}$, or $OR_{17}$;

$R_7$ and $R_8$, each independently, are hydrogen, $R_{18}$, or $R_7$ and $R_8$ together are a carbocyclic 3–8 member ring, but $R_7$ and $R_8$ cannot both be hydrogen in the second of the two above structures;

$R_9$ and $R_{10}$, each independently, are chlorine, bromine, $R_{17}$, or $R_{18}$, or $R_9$ and $R_{10}$ combined are =O, except when X=O, then $R_9$ and $R_{10}$ are not present, and when X is N, then $R_{10}$ is not present, or $R_9$ and $R_{10}$ together are joined in a carbocyclic 3–8 member ring;

$R_{11}$ and $R_{12}$, each independently, are —$OR_{17}$, $R_{18}$, are =O, or are =$CH_2$, except when $R_{11}$ is attached to an $sp^2$ carbon atom in the ring, then $R_{12}$ is not present and $R_{11}$ is $R_{18}$, and when $R_{11}$ and $R_{12}$ combined are =O, then Y cannot be a $C_2$ alkyl;

or $R_{11}$ and $R_{13}$ together are joined in a carbocyclic 3–8 member ring or are —O— to form an epoxide;

$R_{13}$ and $R_{14}$, each independently, are —$OR_{17}$ or $R_{18}$, except when $R_{13}$ is attached to an $sp^2$ carbon atom in the ring, then $R_{14}$ is not present and $R_{13}$ is —$OR_{17}$ or $R_{18}$;

$R_{15}$ and $R_{16}$, each independently, are $R_{18}$ except that $R_{15}$ and $R_{16}$ cannot both be hydrogen, or $R_{15}$ and $R_{16}$ together are joined in a carbocyclic 3–8 member ring, or $R_{15}$ and $R_{16}$ together are —$CH_2$—O— forming an epoxide, or $R_{15}$ and $R_{16}$ combined are =O or =$C(R_{18})(R_{18'})$, except when $R_{15}$ is attached to an $sp^2$ carbon atom in the ring, then $R_{16}$ is not present, and when $R_{15}$ and $R_{16}$ combined are =O, then $R_1$, $R_2$, $R_3$, and $R_4$ cannot all be hydrogen and $R_7$ and $R_8$ cannot both be hydrogen nor can $R_8$ be $OCH_3$ when $R_1$, $R_2$, and $R_4$ are all hydrogen;

but excluding cyclocymopol, cyclocymopol monomethyl ether, cyclocymopol dimethyl ether, and cyclocymonol monomethyl ether acetate.

2. A compound as set forth in claim 1 wherein said compound exhibits activity as a progesterone receptor antagonist.

3. A compound as set forth in claim 1 wherein said compound is a diastereomerically pure 3R diastereomer.

4. A compound as set forth in claim 1 wherein said compound is a diastereomerically pure 3S diastereomer.

5. A compound selected from the group consisting of 1-methylidene-2-(2'-acetoxy-4'-bromo-5'-methoxyphenyl) methyl-3,3-dimethylcyclohexane; (3S)-1-debromocyclocymopol monomethyl ether,2'-acetate; 1-methylidene-2-(2'-hydroxy-4'-bromo-5'-methoxyphenyl) methyl-3,3-dimethylcyclohexane; (3S)-1-debromocyclocymopol monomethyl ether,2'-methylcarbonate; (3R,5R)-5-hydroxycyclocymopol monomethyl ether; 2-(4'-nitrophenyl)methylcyclohexanone; (3S)-1-debromocyclocymopol monomethyl ether; 1-methylidene-6-(2'-acetoxy-4'-bromo-5'-methoxyphenyl) methyl-3,5,5-trimethylcyclohex-2-ene; 1-methylidene-6-(4'-nitrophenyl)methyl-3,5,5-trimethylcyclohex-2-ene; (3R)-1-debromocyclocymopol monomethyl ether; 1-methylidene-6-(2'-hydroxy-4'-bromo-5'-methoxyphenyl) methyl-5,5-dimethylcyclohex-2-ene; 1-methylidene-6-(2'- acetoxy-4'-bromo-5'-methoxyphenyl)methyl-5,5-dimethylcyclohex-2-ene; 1-methylidene-6-(3'-methyl-4'-nitrophenyl)methyl-5,5-dimethylcyclohex-2-ene; trans-1-methylidene-6-(2'-acetoxy-4'-bromo-5'-methoxyphenyl)methyl-4,5,5-trimethylcyclohex-2-ene; 1-methylidene-2-(4'-bromophenyl)methyl-3,3-dimethylcyclohexane; 1-methylidene-2-(2'-hydroxy-4'-bromo-5'-methoxyphenyl)methyl-3,3-dimethylcyclopentane; 1-methylidene-2-(4'-nitrophenyl)methylcyclohexane; (3R)-1-debromocyclocymopol monomethyl ether,2'-methylcarbonate; 1-methylidene-2-(2'-hydroxy-4'-bromo-5'-methoxyphenyl)methylcyclohexane; (3R)-cyclocymopol monomethyl ether,2'-methylcarbonate; (3R)-1-debromocyclocymopol monomethyl ether,2'-benzoate; (3R)-4'-iodocyclocymopol monomethyl ether, cis-1-Methylidene-2-(2'-hydroxy-4'-bromo-5'-methoxyphenyl)methyl-3,3-dimethyl-5-(propanal-1,3-dioxolane)cyclohexane; cis-1-Methylidene-2-(2'-hydroxy-4'-bromo-5'-methoxyphenyl)methyl-3,3-dimethyl-5-(3-hydroxypropyl)cyclohexane; (5R,6S)-1-Methylidene-6-(2'-acetoxy-4'-bromo-5'-methoxyphenyl)methyl-5-methyl-cyclohex-2-ene; (3R)-5-Methyl-5,6-dehydro-1-debromocyclocymopol monomethyl ether, acetate; 1-Hydroxy-1-(4'-nitrophenyl)methyl-2-methylidene-4,6,6-trimethylcyclohex-3-ene; cis-1-Methylidene-2-(2'-hydroxy-4'-bromo-5'-methoxyphenyl)methyl-3,3,5-trimethyl-cyclohexane; 1-Methylidene-6-(4'-nitrophenyl)thio-3,5,5-trimethylcyclohex-2-ene; 8-(2'-Acetoxy-4'-bromo-5'-methoxyphenyl)methyl-5,7,7-trimethylspiro[2.5]oct-4-ene; 1-Methylidene-4-(2'-hydroxy-4'-bromo-5'-methoxyphenyl)methyl-3,5,5-trimethylcyclohex-2-ene; 1-Methylidene-6-(benzofurazan-5'-yl)methyl-3,5,5-trimethylcyclohex-2-ene; 1-Methylidene-6-[trans-(2'-Hydroxy-4'-bromo-5'-methoxyphenyl)-1-propenyl]-3,5,5-trimethylcyclohex-2-ene; trans-1-Methylidene-2-(2'-hydroxy-4'-bromo-5'-methoxyphenyl)methyl-3,3,5-trimethyl-5-(hydroxymethyl)cyclohexane; trans-1-Methylidene-4-allyl-6-(2'-hydroxy-4'-bromo-5'-methoxyphenyl)methyl-5,5-dimethylcyclohex-2-ene; trans-1-Methylidene-4-(2'-hydroxy)ethyl-6-(2"-hydroxy-4"-bromo-5"-methoxyphenyl)methyl-3,5,5-trimethylcyclohex-2-ene; 1-Methylidene-6-(2'-hydroxy-4'-bromo-5'-methoxyphenyl)methyl-3,5,5-trimethylcyclohex-2-ene; trans-1-Methylidene-6-(2'-hydroxy-4'-bromo-5'-methoxyphenyl)methyl-4,5,5-trimethylcyclohex-2-ene; trans-1-Methylidene-2-(2'-hydroxy-4'-bromo-5'-methoxyphenyl)methyl-3,3,4-trimethylcyclohexane; 6-(4'-Nitrophenyl)methyl-5,5-dimethylcyclohex-2-en-1-one; and (3R)-4'-Formylcyclocymopol monomethyl ether.

6. (3S)-1-Debromocyclocymopol monomethyl ether,2'-acetate.

7. 1-Methylidene-6-(4'-nitrophenyl)methyl-3,5,5-trimethylcyclohex-2-ene.

8. (3R)1-Debromocyclocymopol monomethyl ether.

9. (3R)-1-Debromocyclocymopol monomethyl ether,2'-benzoate.

10. A ligand-receptor complex formed by binding of a compound of claim 1 to a progesterone receptor.

11. A ligand-receptor complex formed by binding a compound of claim 5 to a progesterone receptor.

12. A diastereomerically pure 3R diastereomer of cyclocymopol monomethyl ether.

13. A diastereomerically purified 3R diastereomer of cyclocymopol monomethyl ether having a purity such that said purified (3R)-cyclocymopol monomethyl ether exhibits activity as a progesterone receptor antagonist despite the presence of any remaining 3S diastereomer of cyclocymopol monomethyl ether.

14. A pharmacological composition comprising a pharmaceutically acceptable vehicle and one or more compounds from the group consisting of the compounds of claim 1.

15. A pharmacological composition comprising a pharmaceutically acceptable vehicle and one or more compounds of claim 5.

16. A method of purifying a diastereomer of a compound of claim 1, cyclocymopol, or cyclocymopol monomethyl ether, comprising converting said diastereomer to an acetate and separating the diastereomeric acetate.

17. The method of claim 16 wherein the separation is carried out using HPLC.

18. A method of affecting progesterone activity comprising the in vivo administration of a compound from the group consisting of the compounds of claim 1, cyclocymopol, and cyclocymopol monomethyl ether.

19. A method for treating a mammalian subject requiring progesterone receptor antagonist therapy comprising administering to such subject a pharmaceutically effective amount of a compound of claim 1.

20. A method for treating a mammalian subject requiring progesterone receptor antagonist therapy comprising administering to such subject a pharmaceutically effective amount of the 3R diastereomer of cyclocymopol monomethyl ether or of cyclocymopol.

21. A method for treating a mammalian subject requiring progesterone receptor agonist therapy comprising administering to such subject a pharmaceutically effective amount of the 3S diastereomer of cyclocymopol monomethyl ether or of cyclocymopol.

22. A method for modulating a process mediated by progesterone receptors comprising causing said process to be conducted in the presence of at least one compound as set forth in claim 1.

23. A method for modulating a process mediated by progesterone receptors comprising causing said process to be conducted in the presence of at least one compound from the group consisting of cyclocymopol and cyclocymopol monomethyl ether.

24. A method for modulating a process mediated by progesterone receptors comprising administering to a mammalian subject an amount, effective to moderate said process mediated by said progesterone receptors, of a compound of claim 1.

25. A method for modulating a process mediated by progestrone receptors comprising administering to a mammalian subject an amount, effective to moderate said process mediated by said progesterone receptors, of at least one compound from the group consisting of cyclocymopol and cyclocymopol monomethyl ether.

26. A method for determining the presence of one or more progesterone receptors comprising combining at least one compound from the group consisting of the compounds of claim 1, cyclocymopol, and cyclocymopol monomethyl ether with a sample containing one or more unknown receptors and determining whether said compound binds to any receptor in said sample.

27. A method of purifying progesterone receptors comprising combining at least one compound from the group consisting of the compounds of claim 1, cyclocymopol, and cyclocymopol monomethyl ether with a sample containing progesterone receptors, allowing said compound to bind said progesterone receptors, and separating out the bound combination of said compound and said progesterone receptors.

* * * * *

UNITED STATES PATENT AND TRADEMARK OFFICE
CERTIFICATE OF CORRECTION

PATENT NO. : 5,808,139
DATED : September 15, 1998
INVENTOR(S): Pathirana et al.

It is certified that error appears in the above-identified patent and that said Letters Patent is hereby corrected as shown below:

Column 2, line 10, change "MRNA" to --mRNA--.

Column 2, line 12, change "MRNA" to --mRNA--.

Column 6, line 57, change "SP$^2$" to -- sp$^2$ --.

Column 16, line 20, change "386" to --3.86 --.

Column 16, line 20, change "692" to --6.92 --.

Column 16, line 46, change "387" to --3.87 --.

Column 18, line 59, add sub-title --<u>Aliphatic Subunit Synthesis</u>--.

Column 19, line 56, change "2.25 2.32" to --2.25 and 2.32 --.

Column 20, line 62, change "1methylidene" to --1-methylidene --.

Column 24, line 33, change "5-trimethylcyclohex-2-en-1one" to --5-trimethylcyclohex-2-en-1-one --.

Column 24, line 37, change "geminal-CH$_3$,S" to -- geminal-CH$_3$'s --.

UNITED STATES PATENT AND TRADEMARK OFFICE
CERTIFICATE OF CORRECTION

PATENT NO. : 5,808,139
DATED : September 15, 1998
INVENTOR(S): Pathirana et al.

It is certified that error appears in the above-identified patent and that said Letters Patent is hereby corrected as shown below:

Column 25, line 27, change "2. TBAF/THF AcO" to -- 2. TBAF/THF $Ac_2O$ --.

Column 26, line 40, change "C=CH2" to -- $C=CH_2$ --.

Column 28, line 15, change "1H NMR" to -- $^1H$ NMR --.

Column 31, line 28, change "hexaneslethyl" to -- hexanes/ethyl --.

Column 32, line 12, change "JB" to -- $J_B$ --.

Column 37, line 19, change "$NH_4C$" to -- $H_4Cl$ --.

Column 38, line 44, change "warn" to --warm--.

Column 39, line 45, change "231" to --2.31--.

Column 41, line 41, change "1202991" to --120299]--.

Column 41, line 53, change "9H" to --0.99[s,9H,--.

Column 42, line 4, change "$Na_2so_4$" to --$Na_2SO_4$,--.

Column 42, line 49, change "33%" to --13%--.

UNITED STATES PATENT AND TRADEMARK OFFICE
CERTIFICATE OF CORRECTION

PATENT NO. : 5,808,139
DATED : September 15, 1998
INVENTOR(S) : Pathirana et al.

It is certified that error appears in the above-identified patent and that said Letters Patent is hereby corrected as shown below:

Column 44, line 64, change "MnL" to -- mL --.

Column 44, line 67, change "methanol hexanes/ethyl water" to -- methanol/water --.

Column 47, line 12, change "(m, 2)" to -- (m, 2H) --.

Column 48, line 22, change "(dd, 1H, J=7.0 Hz," to -- (dd, 1H, J=7.0 Hz,6-H), --.

Column 48, line 24, change "(s, 1H, OR)" to -- (s, 1H, OH) --.

Column 49, line 62, change "fimel" to -- funnel --.

Column 51, line 34, change "$J_A$=12.0" to -- $J_{AB}$=12.0 --.

Column 51, line 59, change "fimel" to -- funnel --.

Column 52, line 36, change "112" to -- 1.12 --.

Column 53, line 12, change "methoxyphenol" to -- methoxyphenyl --.

Column 55, line 57, change "(3R,5S-5" to -- (3R,5S)-5 --.

UNITED STATES PATENT AND TRADEMARK OFFICE
CERTIFICATE OF CORRECTION

PATENT NO. : 5,808,139
DATED : September 15, 1998
INVENTOR(S) : Pathirana et al.

It is certified that error appears in the above-identified patent and that said Letters Patent is hereby corrected as shown below:

Column 56, line 44, change "(2s, 2X3H, gerninal-CH$_3$'s)" to --(2s, 2X3H, geminal-CH$_3$'s) --.

Column 57, line 24, add --Representative derivative compounds include:--.

Column 66, line 57, change "Ln" to --in--.

Column 67, line 57, add --A tablet is prepared using the ingredients below:--.

Column 70, line 43, change "cyclocymonol" to --cyclocymopol--.

Signed and Sealed this

Twentieth Day of June, 2000

Attest:

Q. TODD DICKINSON

*Attesting Officer*   *Director of Patents and Trademarks*